(12) United States Patent
Fujie et al.

(10) Patent No.: US 12,387,829 B2
(45) Date of Patent: Aug. 12, 2025

(54) MEDICATION SUPPORT APPARATUS

(71) Applicants: Hiroshi Fujie, Aichi (JP); Hirotaka Hayashi, Aichi (JP); Akira Kojima, Kanagawa (JP); Takuya Morinaga, Tokyo (JP); Wataru Nozaki, Kanagawa (JP)

(72) Inventors: Hiroshi Fujie, Aichi (JP); Hirotaka Hayashi, Aichi (JP); Akira Kojima, Kanagawa (JP); Takuya Morinaga, Tokyo (JP); Wataru Nozaki, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 925 days.

(21) Appl. No.: 17/518,813

(22) Filed: Nov. 4, 2021

(65) Prior Publication Data
US 2022/0157426 A1    May 19, 2022

(30) Foreign Application Priority Data

Nov. 16, 2020  (JP) ................. 2020-190568
Nov. 30, 2020  (JP) ................. 2020-198593

(51) Int. Cl.
*A61J 7/00* (2006.01)
*G16H 20/13* (2018.01)
(Continued)

(52) U.S. Cl.
CPC .......... *G16H 20/13* (2018.01); *G16H 40/60* (2018.01); *A61J 1/00* (2013.01); *A61J 7/0076* (2013.01)

(58) Field of Classification Search
CPC ....................................................... G16H 20/13
(Continued)

(56) References Cited

U.S. PATENT DOCUMENTS 8,082,957 B2 *  12/2011  Yuyama ............... G07F 13/10
                                                        198/596
2002/0173875 A1  11/2002  Wallace et al.
(Continued)

FOREIGN PATENT DOCUMENTS

CN    104097858 A    10/2014
JP    H04-095040 U   8/1992
(Continued)

OTHER PUBLICATIONS

U.S. Appl. No. 17/326,753, filed May 21, 2021.
(Continued)

*Primary Examiner* — Gene O Crawford
*Assistant Examiner* — Ayodeji T Ojofeitimi
(74) *Attorney, Agent, or Firm* — Harness, Dickey & Pierce, P.L.C.

(57) ABSTRACT

A medication support apparatus includes a storage unit, an extracting unit, a transfer unit, and a medicine distributing unit. The storage unit is configured to store, in a stacked manner, one-dose packages in each of which medicines are packed. The extracting unit is configured to extract a specific one-dose package from the storage unit. The transfer unit is configured to transfer the one-dose package extracted by the extracting unit. One-dose package transferred by the transfer unit is configured to be arranged on the medicine distributing unit. The extracting unit is configured to be located under the storage unit when the one-dose package is extracted from the storage unit.

20 Claims, 31 Drawing Sheets

(51) Int. Cl.
   *G16H 40/60* (2018.01)
   *A61J 1/00* (2023.01)

(58) Field of Classification Search
   USPC .......................................................... 700/242
   See application file for complete search history.

(56) References Cited

U.S. PATENT DOCUMENTS

| | | |
|---|---|---|
| 2005/0049747 A1 | 3/2005 | Willoughby et al. |
| 2008/0061071 A1 | 3/2008 | Omura et al. |
| 2009/0014461 A1 | 1/2009 | Omura et al. |
| 2021/0361532 A1 | 11/2021 | Hayashi et al. |

FOREIGN PATENT DOCUMENTS

| | | |
|---|---|---|
| JP | 200024085 A | 1/2000 |
| JP | 2016-182185 A | 10/2016 |
| JP | 2017-153646 | 9/2017 |
| JP | 2017-192455 | 10/2017 |
| JP | 2018-050936 A | 4/2018 |
| JP | 6429334 | 11/2018 |
| JP | 2020-083498 A | 6/2020 |
| JP | 2020-151017 A | 9/2020 |

OTHER PUBLICATIONS

Japanese Office Action dated Jan. 30, 2024 issued in corresponding Japanese Appln. No. 2020-198593 (with English translation).
Japanese Office Action dated Feb. 13, 2024 issued in corresponding Japanese Appln. No. 2020-190568 (with English translation).
Chinese Office Action for Chinese Application No. 202111347023.6 and English translation thereof dated Mar. 19, 2024.

\* cited by examiner

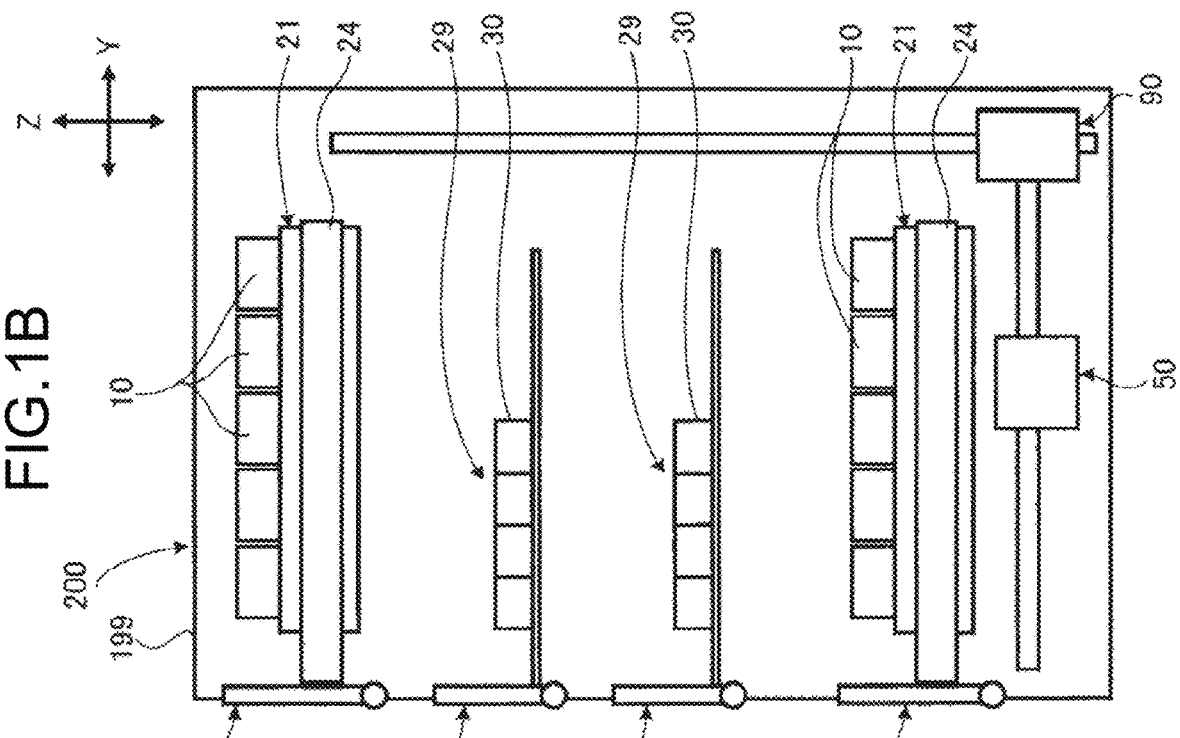
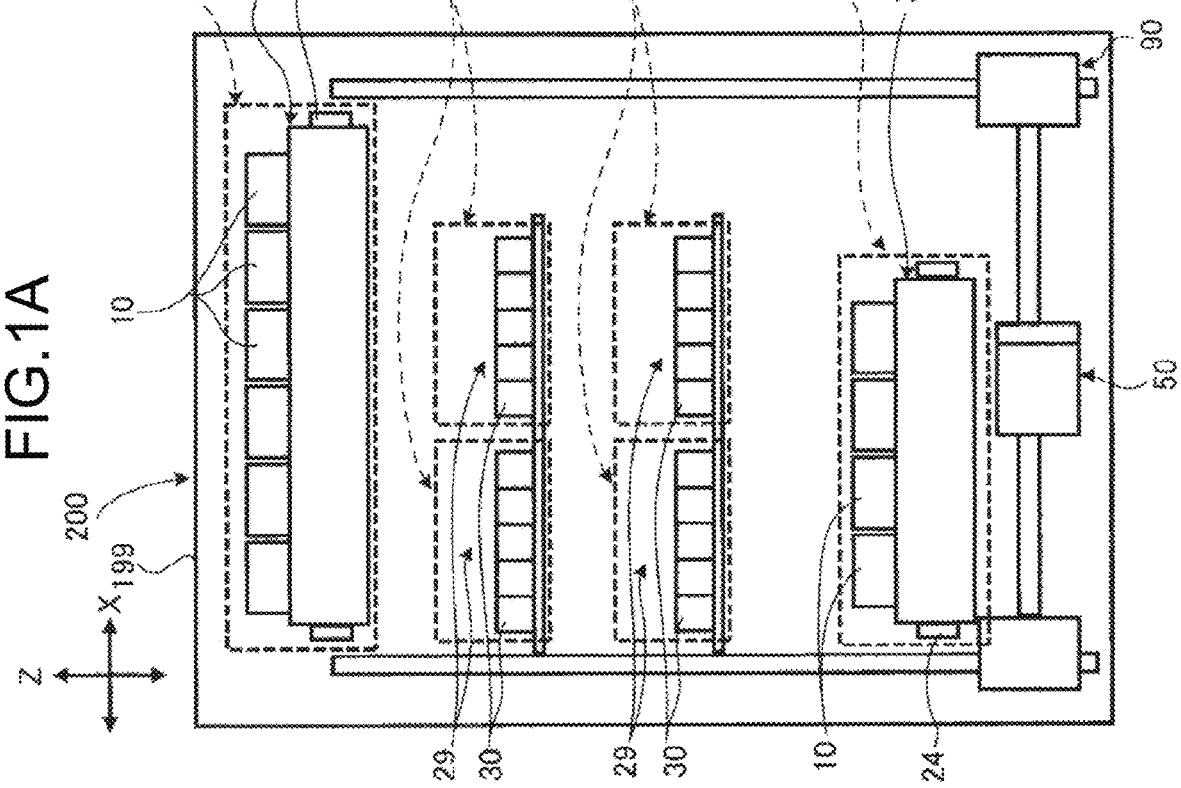

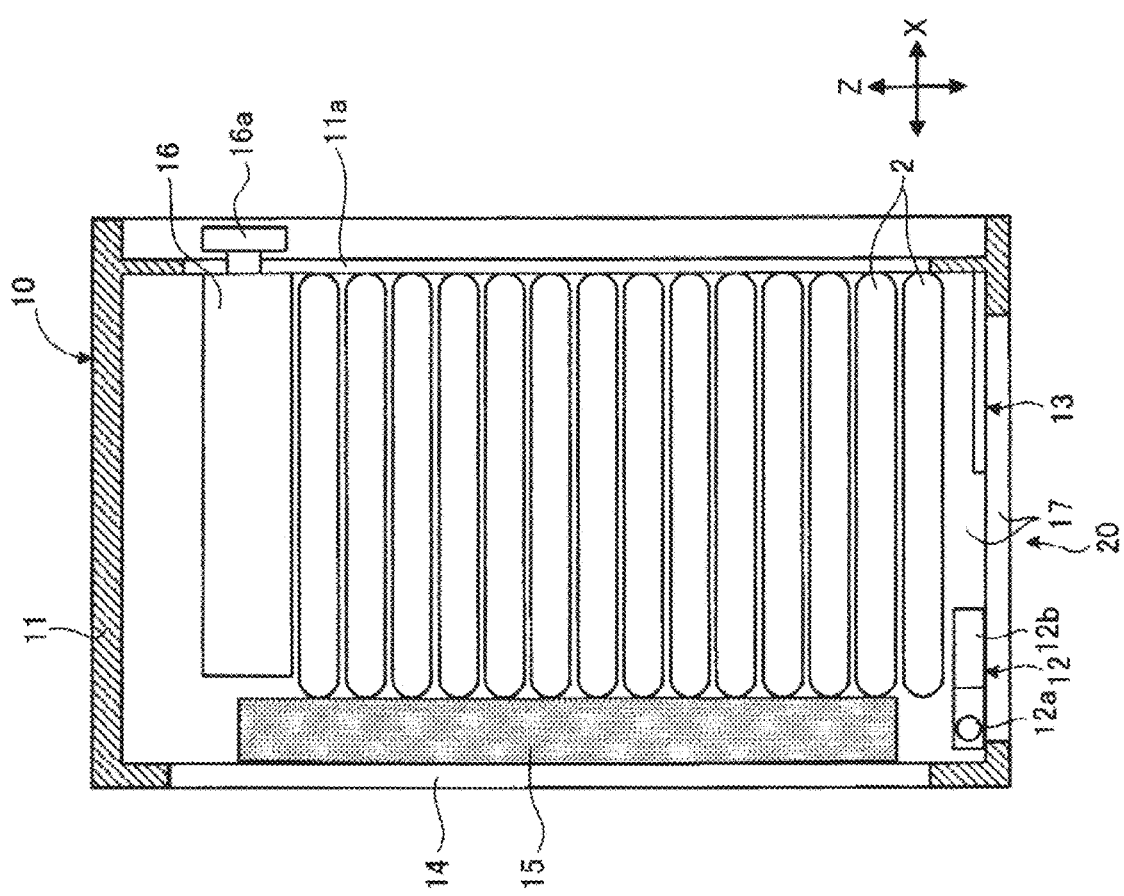
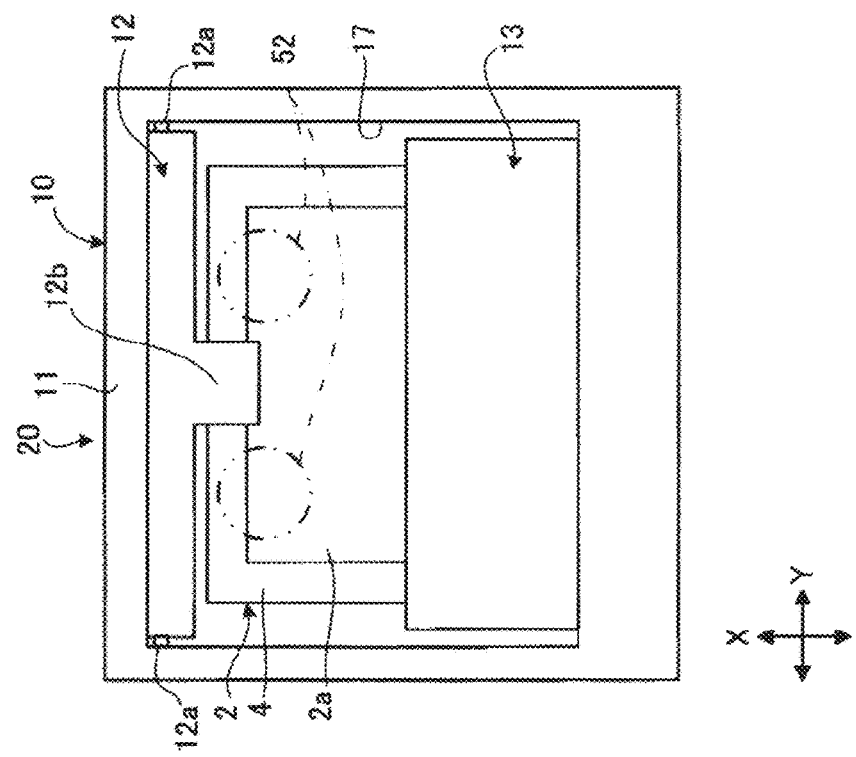

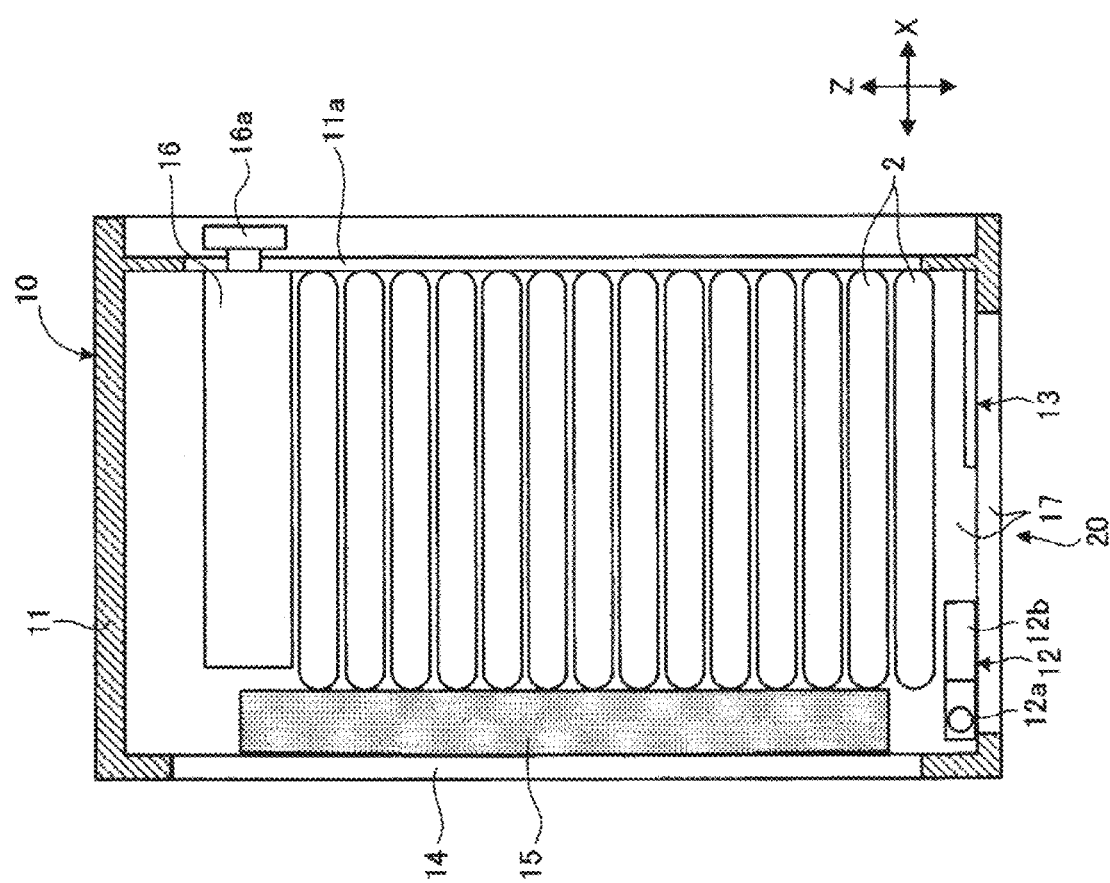
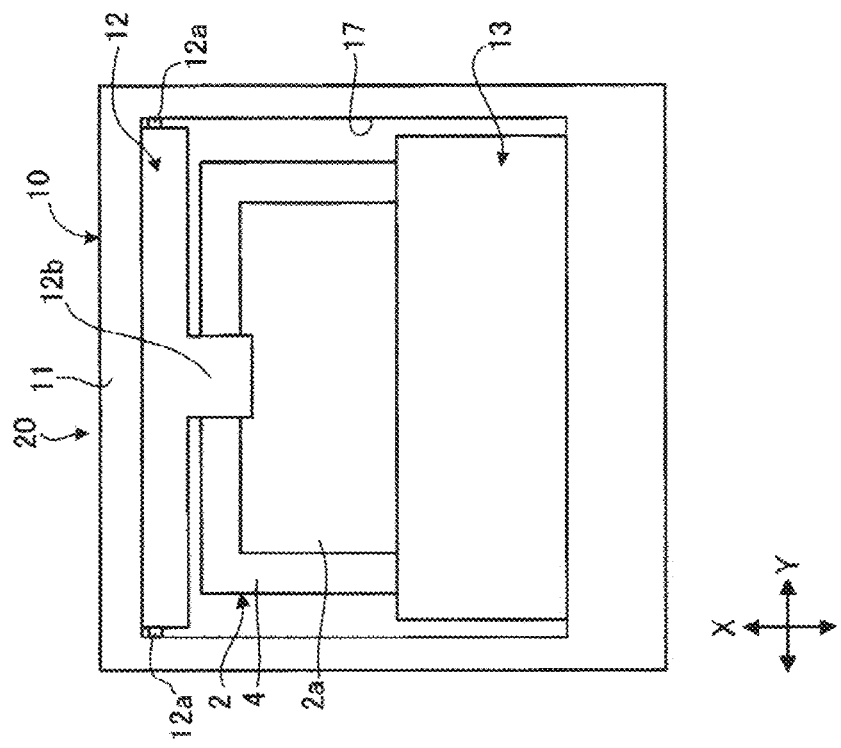

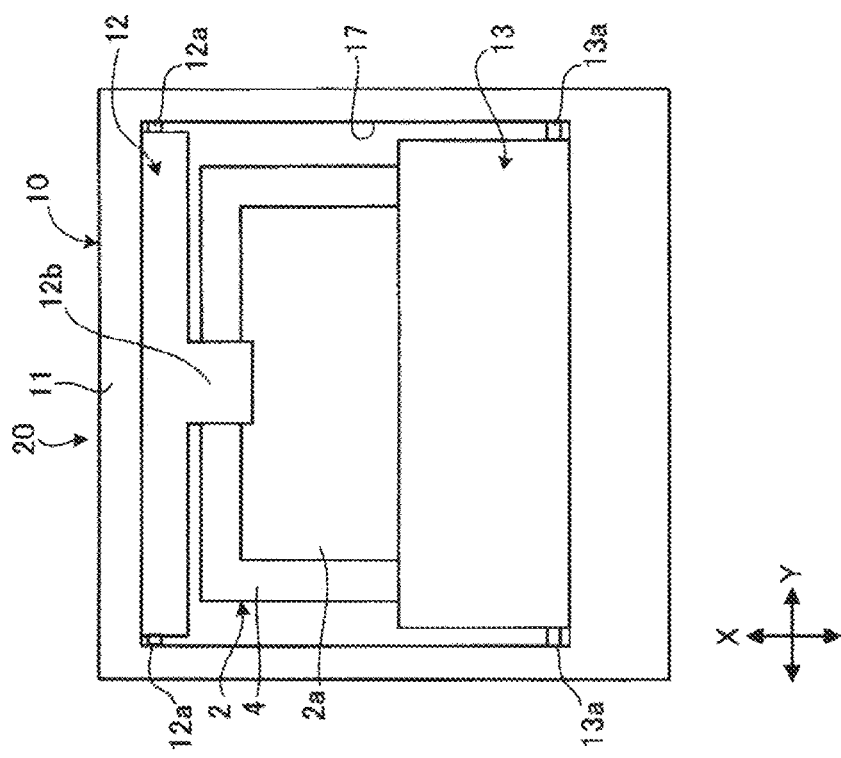
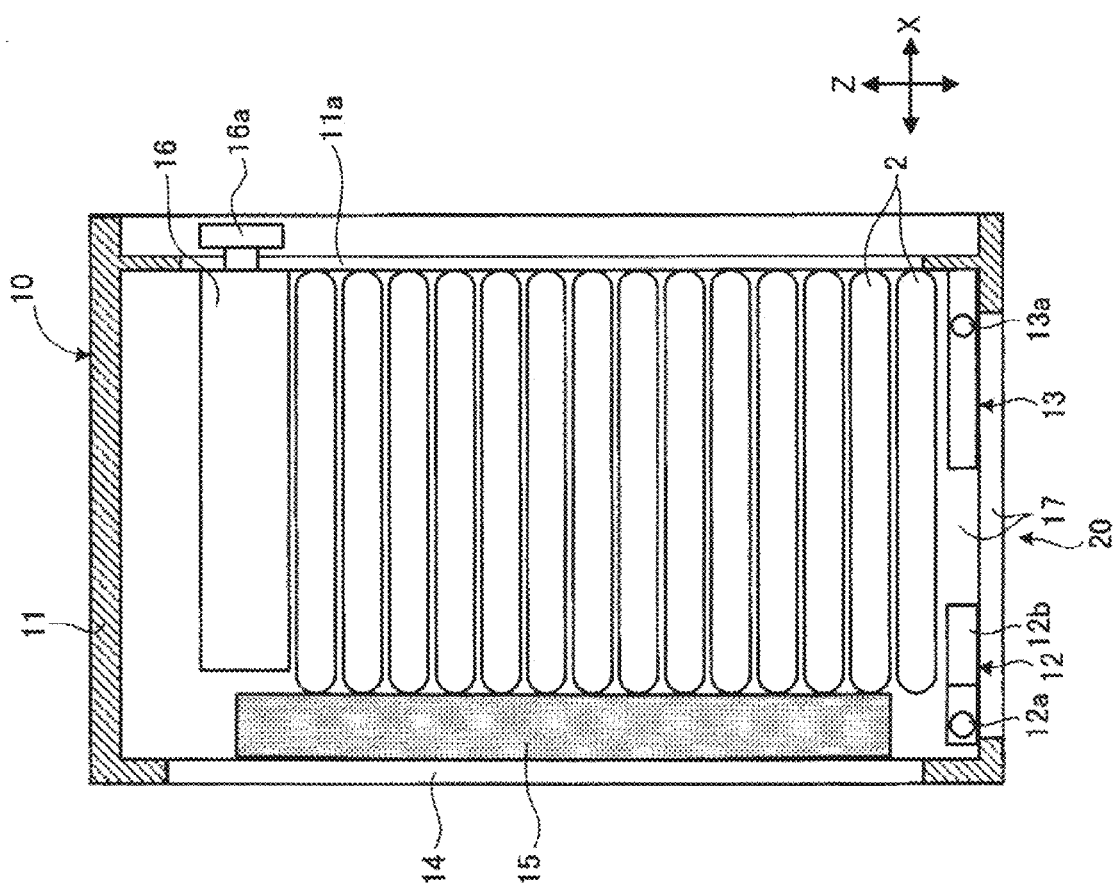

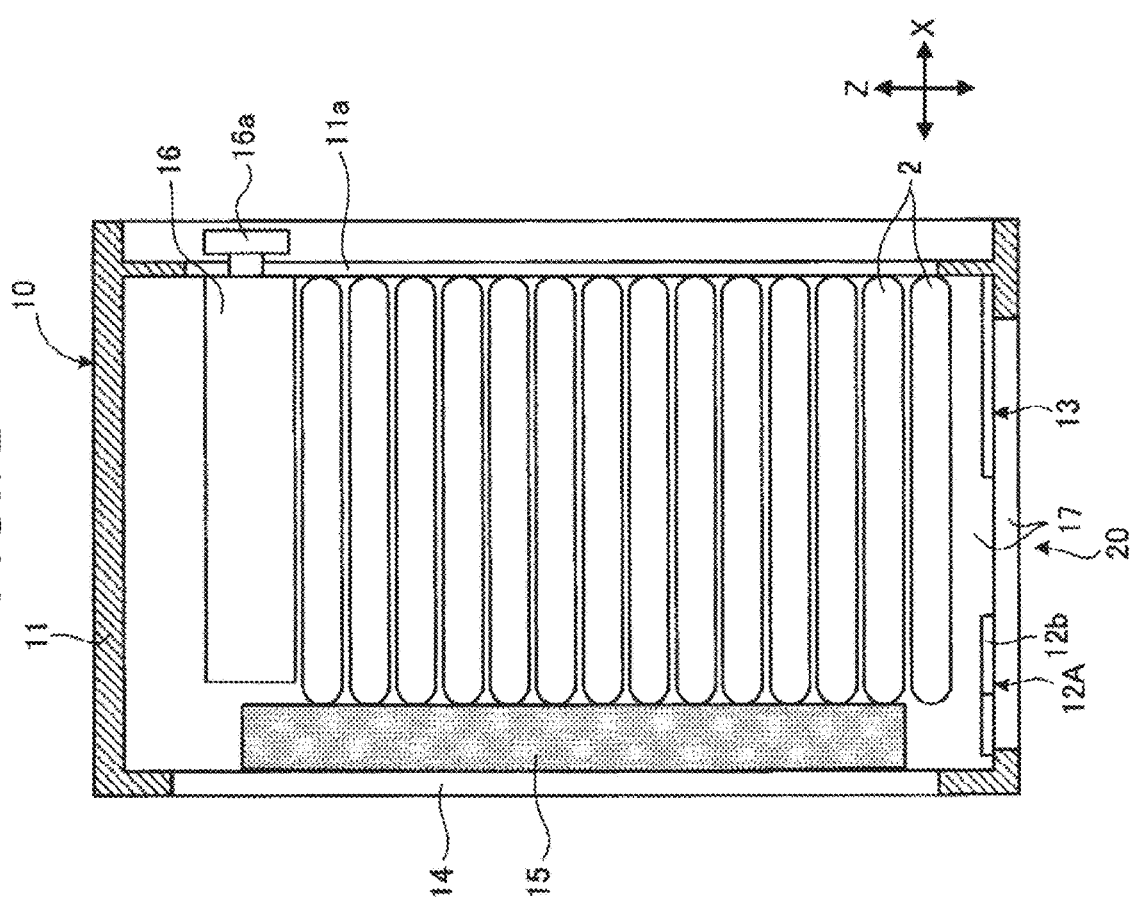
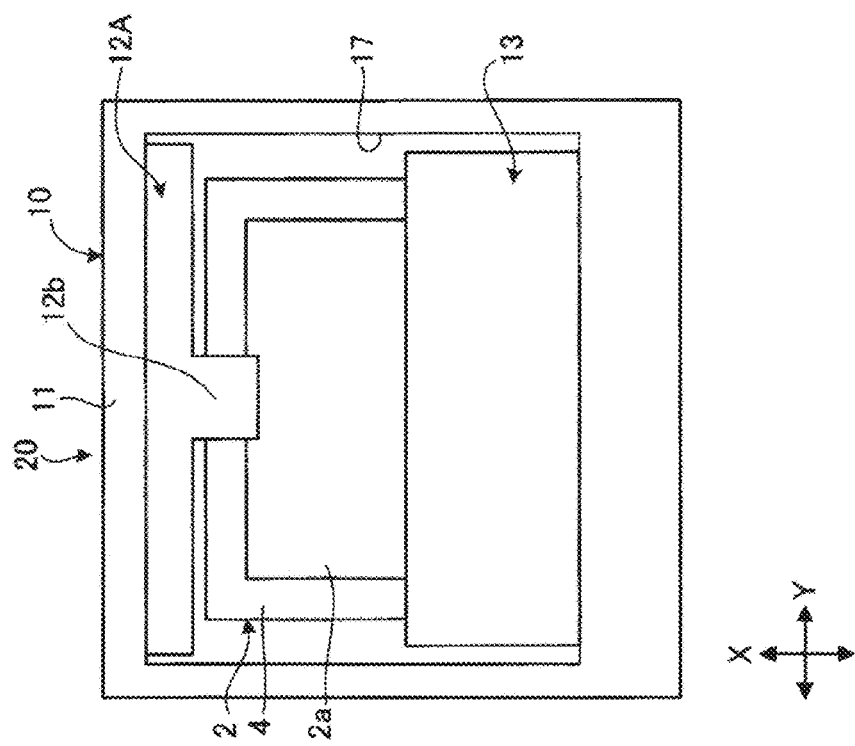

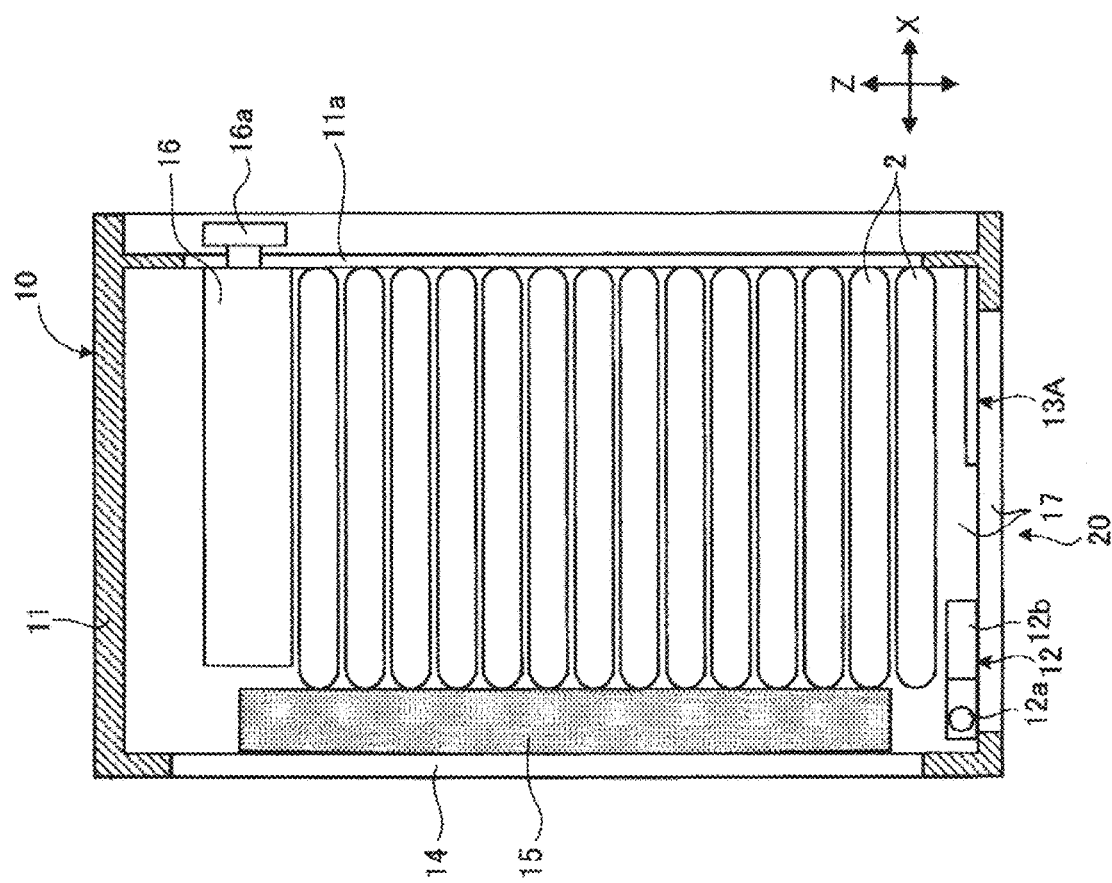
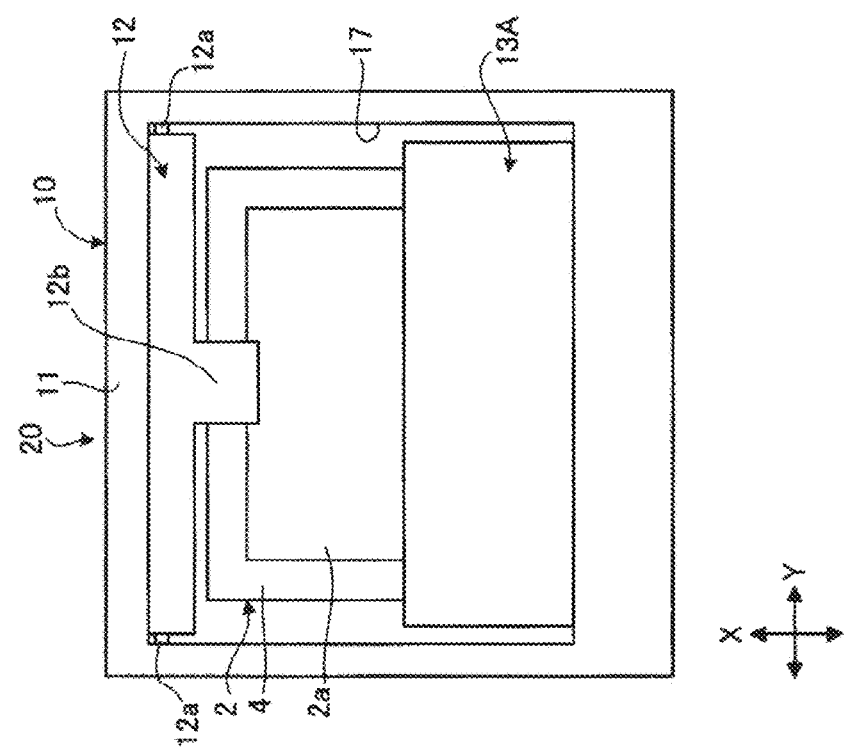

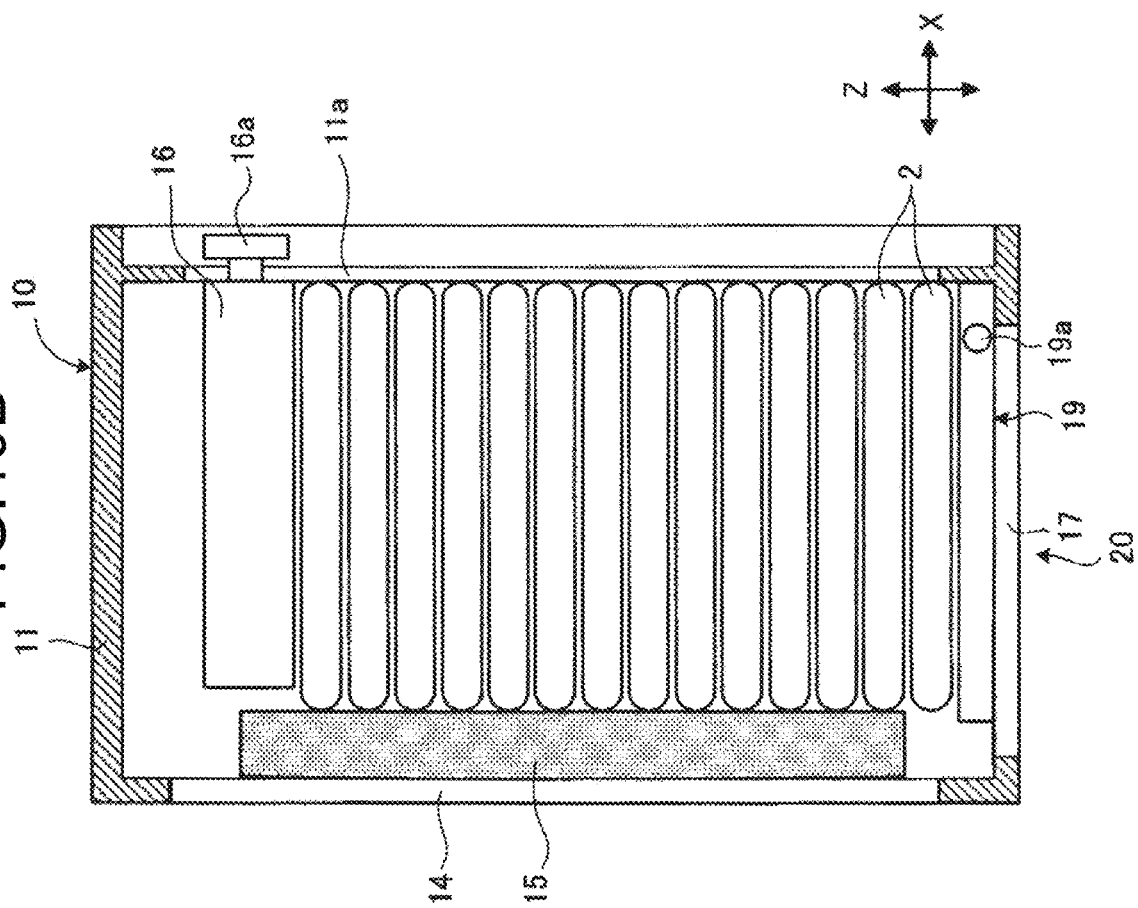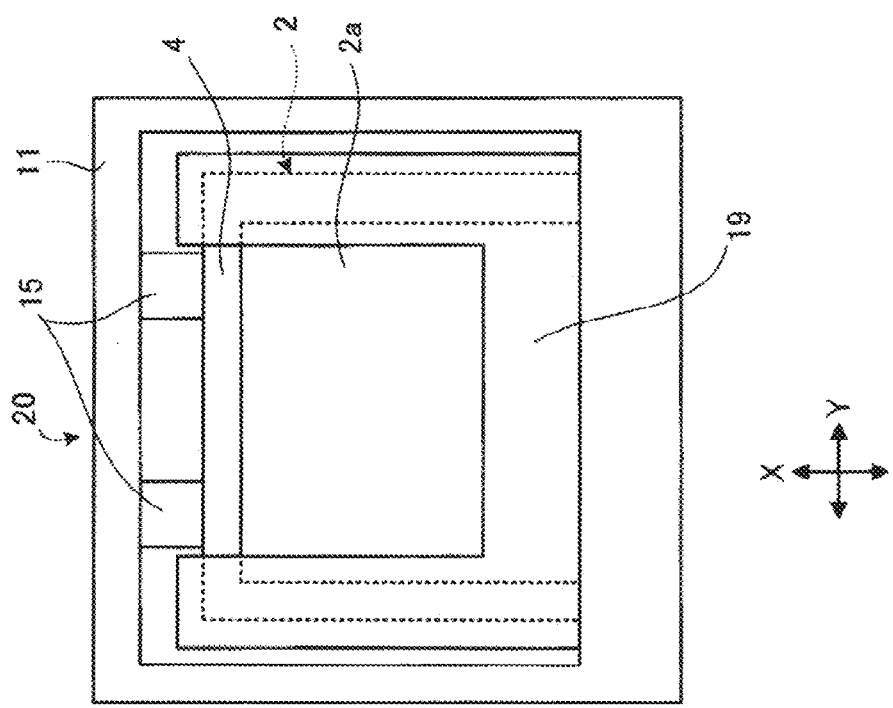

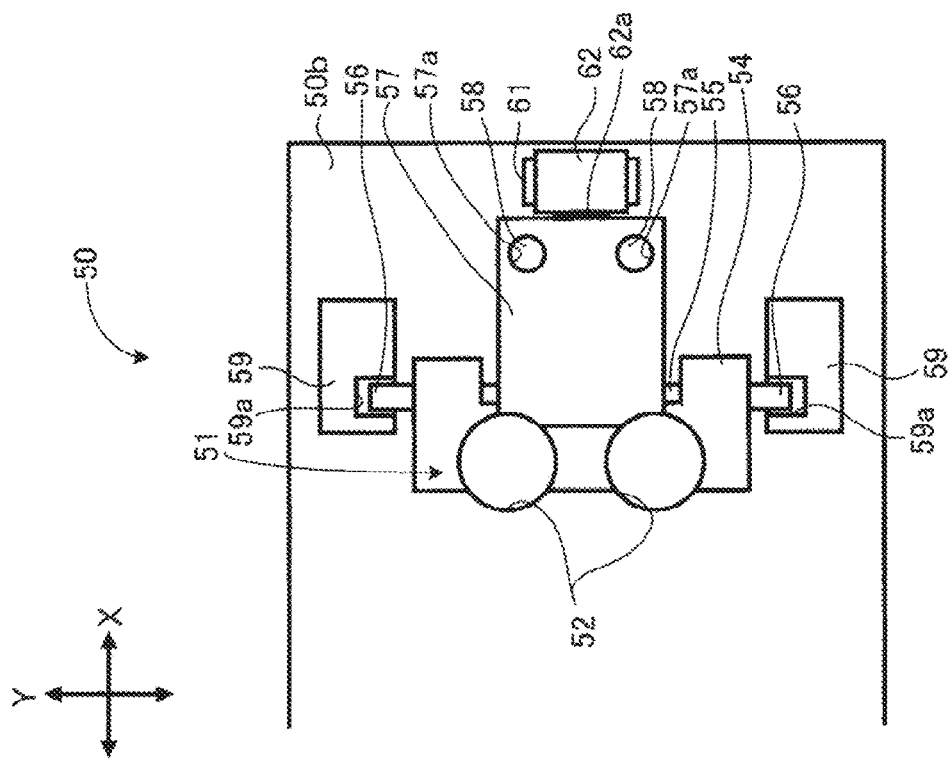
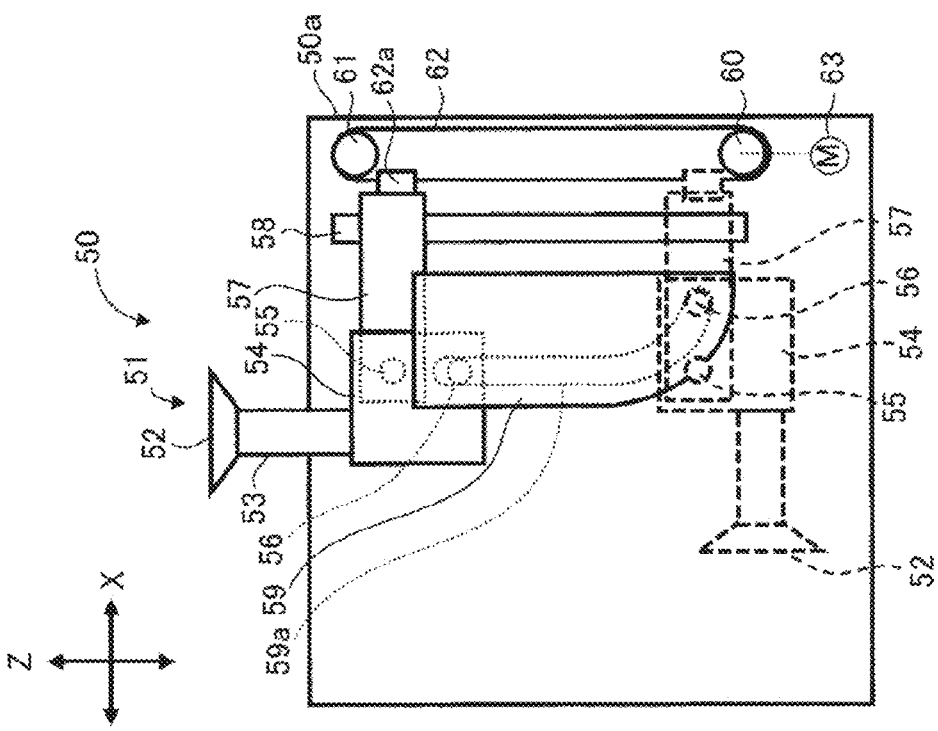

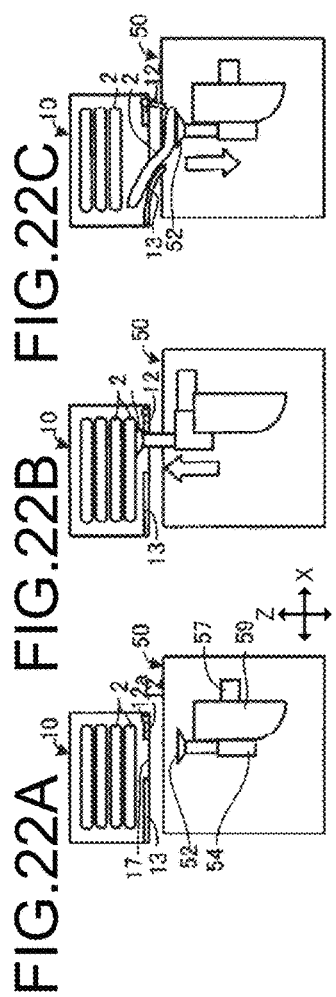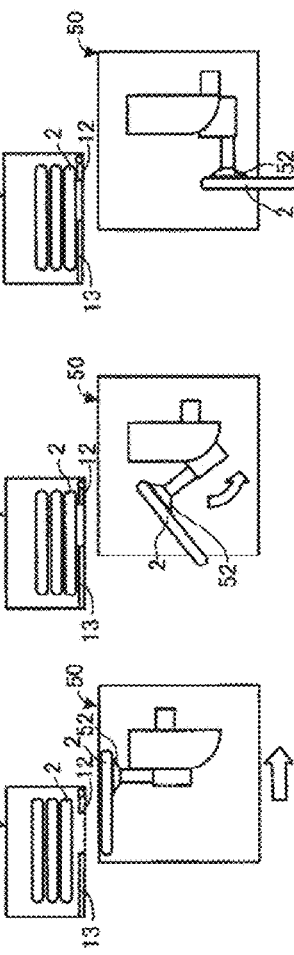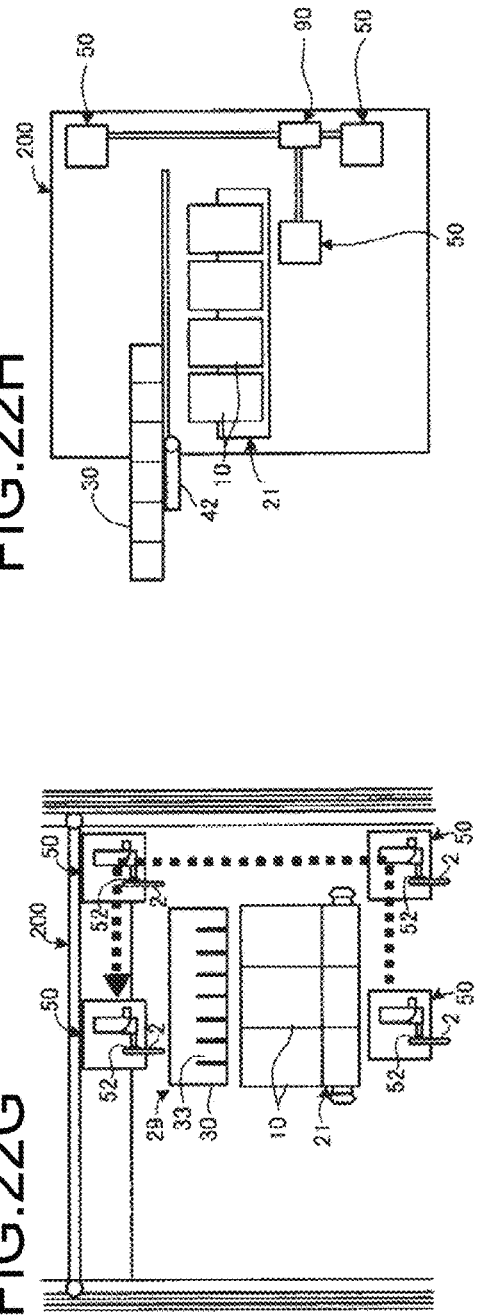

FIG.24A
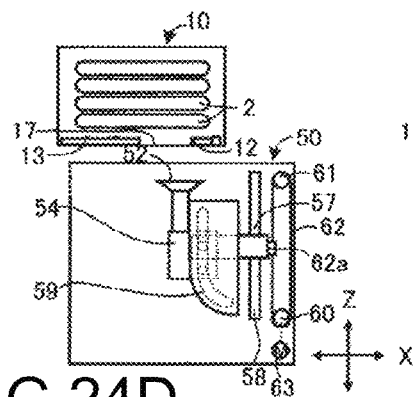
FIG.24B
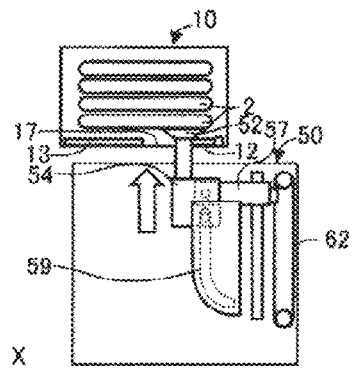
FIG.24C
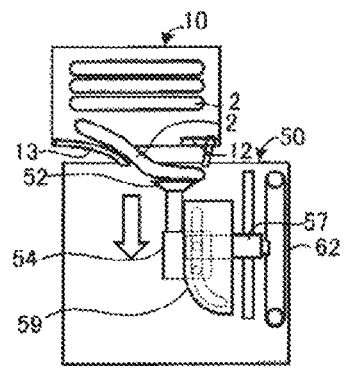
FIG.24D
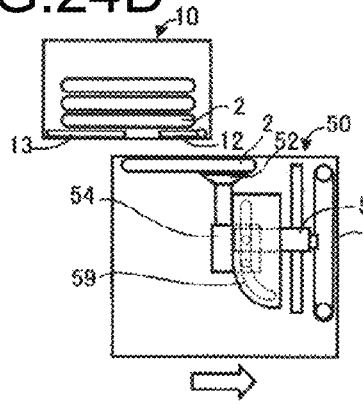
TRANSFER EXTRACTING UNIT 50 TO MEDICINE DISTRIBUTION TRAY 30 BY TRANSFER UNIT 90
FIG.24E
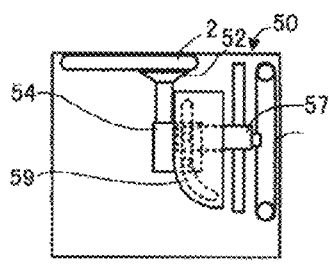
FIG.24F
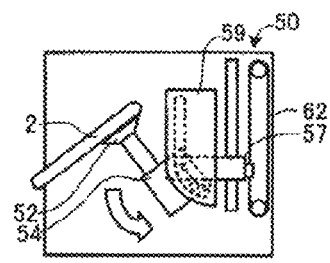
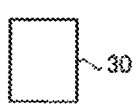
FIG.24G
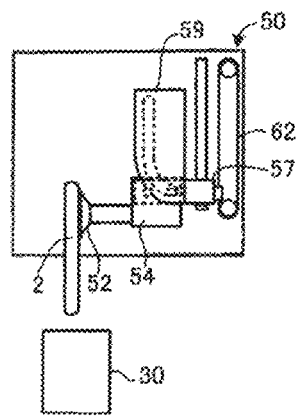
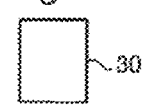

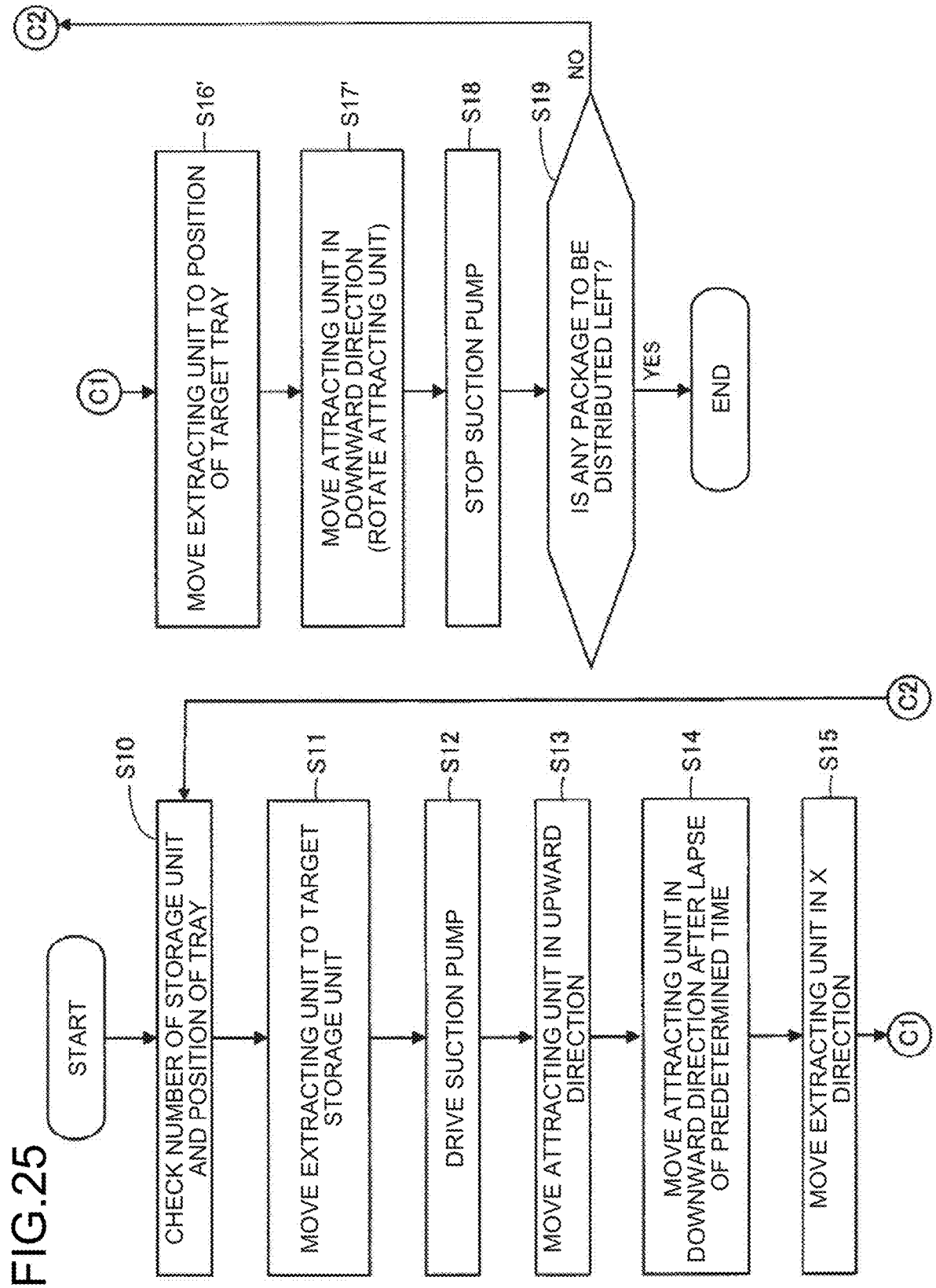

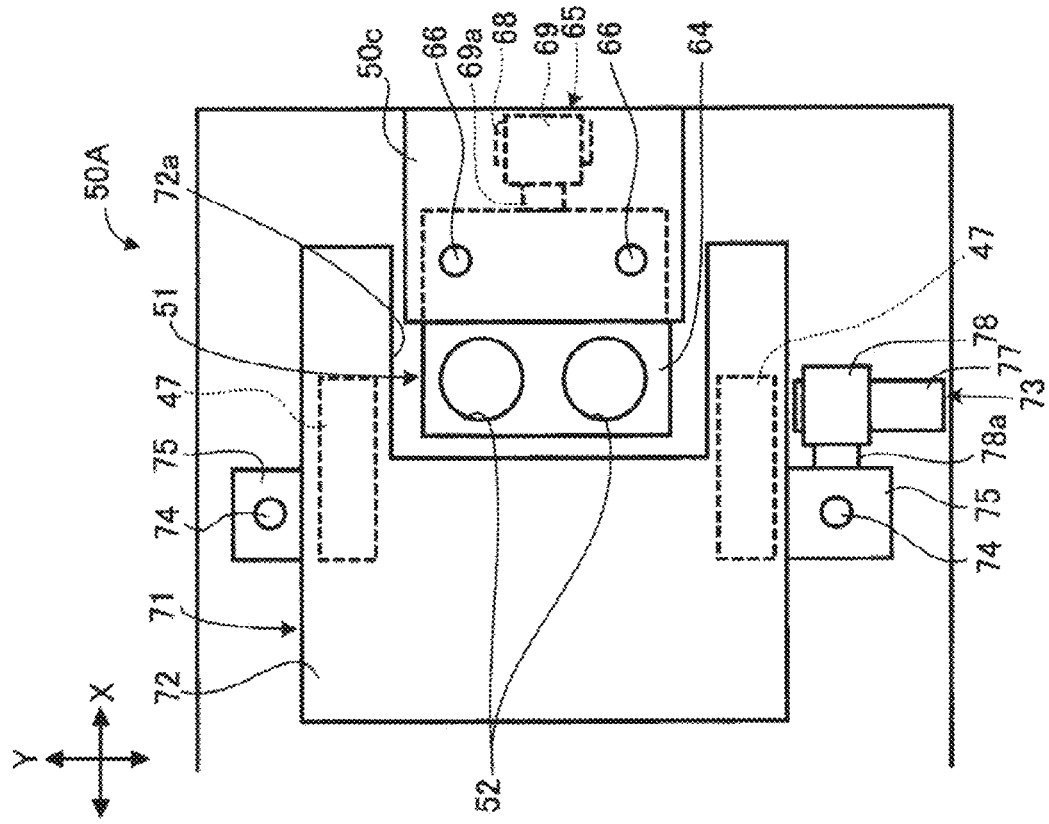
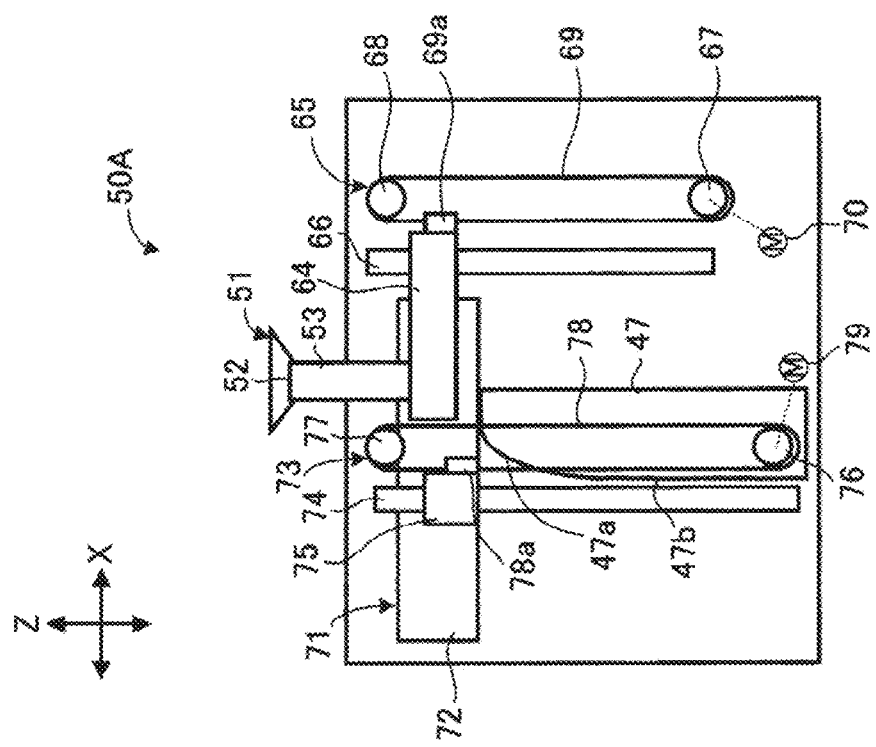

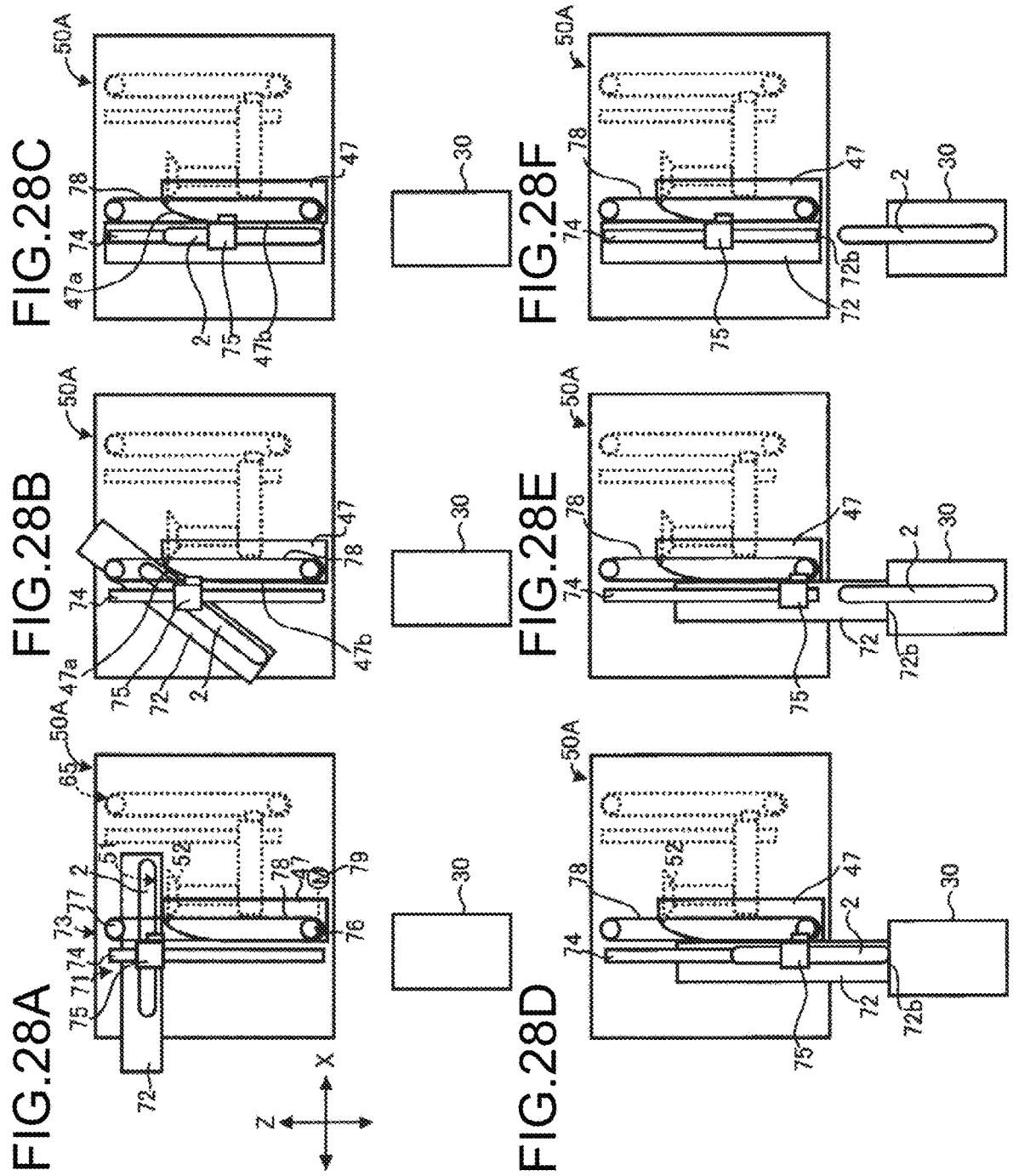

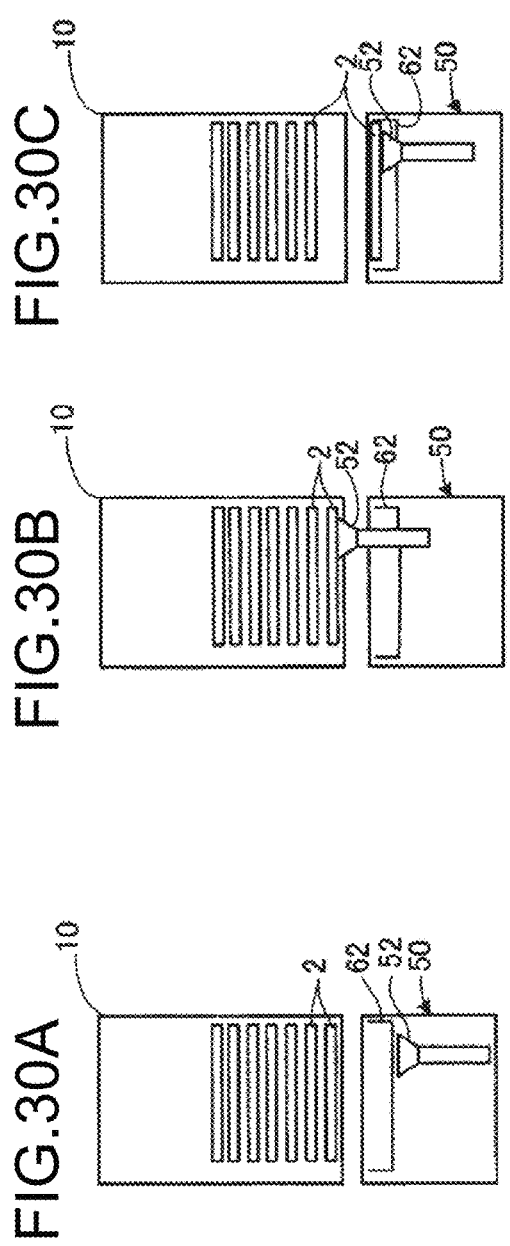
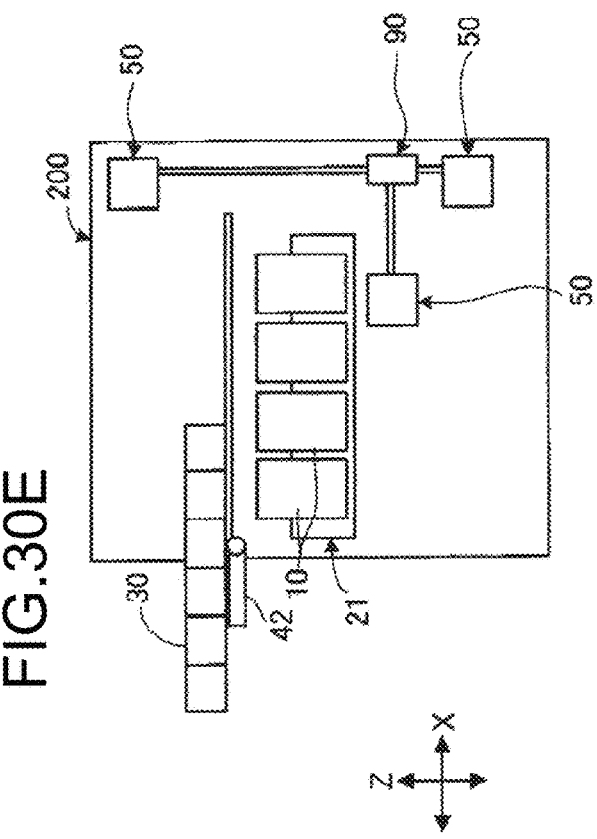
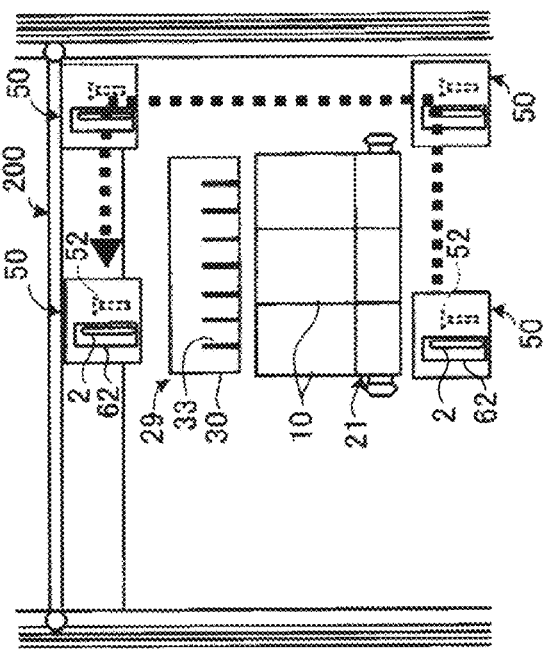

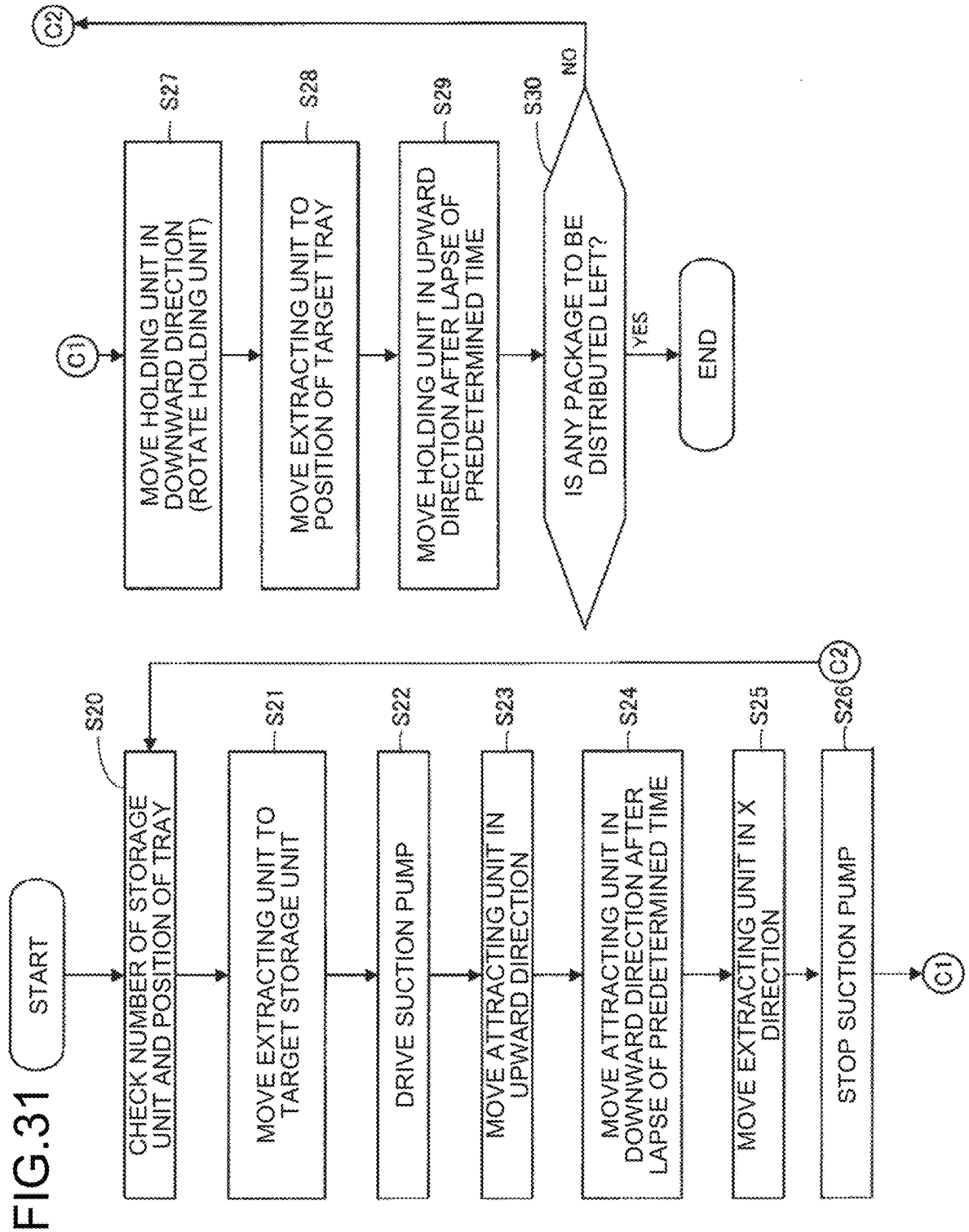

MEDICATION SUPPORT APPARATUS

CROSS-REFERENCE TO RELATED APPLICATIONS

The present application claims priority under 35 U.S.C. § 119 to Japanese Patent Application. No. 2020-190568, filed on Nov. 16, 2020 and Japanese Patent Application No. 2020-198593, filed on Nov. 30, 2020. The contents of which are incorporated herein by reference in their entirety.

BACKGROUND OF THE INVENTION

1. Field of the Invention

The present invention relates to a medication support apparatus.

2. Description of the Related Art

A medication support apparatus that extracts, with use of an attracting device, a package of medicines (one-dose package), in which medicines are packed, from a housing unit (storage unit) that stores therein the package, sends the package to a receiving tray, and provides the medicines to a medicated person or a medication assistant by discharging the package from an opening (outlet) of a main body casing has been known (for example, see Japanese Unexamined Patent Application Publication No. 2017-192455).

In the medication support apparatus described in Japanese Unexamined Patent Application Publication No. 2017-192455, it is possible to provide a one-dose package to be taken to the medication assistant or the like at regular times.

However, the opening is arranged in an upper portion of the storage unit of the medication support apparatus and the attracting device extracts the one-dose package from an upper side of the storage unit, so that it is necessary to provide a lifter that lifts up the one-dose packages such that one-dose packages that are left in the storage unit can easily be extracted. Therefore, there is a problem in that a structure of the apparatus becomes complicated.

SUMMARY OF THE INVENTION

According to an aspect of the present invention, a medication support apparatus includes a storage unit, an extracting unit, a transfer unit, and a medicine distributing unit. The storage unit is configured to store, in a stacked manner, one-dose packages in each of which medicines are packed. The extracting unit is configured to extract a specific one-dose package from the storage unit. The transfer unit is configured to transfer the one-dose package extracted by the extracting unit. One-dose package transferred by the transfer unit is configured to be arranged on the medicine distributing unit. The extracting unit is configured to be located under the storage unit when the one-dose package is extracted from the storage unit.

BRIEF DESCRIPTION OF THE DRAWINGS

FIG. 1A is a front view of an entire medication support apparatus according to a first embodiment of the present invention;
FIG. 1B is a side view of FIG. 1A;
FIG. 4A is a bottom view of a storage unit;
FIG. 4B is a vertical cross-sectional view of FIG. 4A;
FIG. 5A is a bottom view of a storage unit according to a first example;
FIG. 5B is a vertical cross-sectional view of the storage unit in FIG. 5A;
FIG. 6A is a bottom view of a storage unit according to a second example;
FIG. 6B is a vertical cross-sectional view of the storage unit in FIG. 6A;
FIG. 7A is a bottom view of a storage unit according to a third example;
FIG. 7B is a vertical cross-sectional view of FIG. 7A;
FIG. 8A is a bottom view of a storage unit according to a fourth example;
FIG. 8B is a vertical cross-sectional view of FIG. 8A;
FIG. 10A is a bottom view of a storage unit according to a sixth example;
FIG. 10B is a vertical cross-sectional view of FIG. 10A;
FIG. 17A is a front view illustrating a configuration of an extracting unit;
FIG. 17B is a plan view of FIG. 17A.

FIG. 22A is a diagram for explaining the flow of entire main operation of the medication support apparatus in FIG. 1A;

FIG. 22B is a diagram for explaining the flow of the entire main operation of the medication support apparatus in FIG. 1A;

FIG. 22C is a diagram for explaining the flow of the entire main operation of the medication support apparatus in FIG. 1A;

FIG. 22D is a diagram for explaining the flow of the entire main operation of the medication support apparatus in FIG. 1A;

FIG. 22E is a diagram for explaining the flow of the entire main operation of the medication support apparatus in FIG. 1A;

FIG. 22F is a diagram for explaining the flow of the entire main operation of the medication support apparatus in FIG. 1A;

FIG. 22G is a diagram for explaining the flow of the entire main operation of the medication support apparatus in FIG. 1A;

FIG. 22H is a diagram for explaining the flow of the entire main operation of the medication support apparatus in FIG. 1A;

FIG. 24A is an operation transition diagram for explaining a timing at which a posture of an attracting unit of the extracting unit according to the first embodiment is changed;

FIG. 24B is an operation transition diagram for explaining a timing at which the posture of the attracting unit of the extracting unit according to the first embodiment is changed;

FIG. 24C is an operation transition diagram for explaining a timing at which the posture of the attracting unit of the extracting unit according to the first embodiment is changed;

FIG. 24D is an operation transition diagram for explaining a timing at which the posture of the attracting unit of the extracting unit according to the first embodiment is changed;

FIG. 24E is an operation transition diagram for explaining a timing at which the posture of the attracting unit of the extracting unit according to the first embodiment is changed;

FIG. 24F is an operation transition diagram for explaining a timing at which the posture of the attracting unit of the extracting unit according to the first embodiment is changed;

FIG. 24G is an operation transition diagram for explaining a timing at which the posture of the attracting unit of the extracting unit according to the first embodiment is changed;

FIG. 25 is a flowchart illustrating the flow of operation that is performed by the extracting unit according to the first embodiment in accordance with FIG. 24A to FIG. 24G;

FIG. 26A is a front view illustrating a configuration of an extracting unit according to a second embodiment;

FIG. 26B is a plan view of FIG. 26A;

FIG. 27A is a front view illustrating operation of the extracting unit according to the second embodiment;

FIG. 27B is a front view illustrating operation of the extracting unit according to the second embodiment;

FIG. 27C is a front view illustrating operation of the extracting unit according to the second embodiment;

FIG. 27D is a front view illustrating operation of the extracting unit according to the second embodiment;

FIG. 27E is a front view illustrating operation of the extracting unit according to the second embodiment;

FIG. 28A is a front view illustrating operation of the extracting unit according to the second embodiment, which is continued from the operation in FIG. 27A to FIG. 27E;

FIG. 28B is a front view illustrating operation of the extracting unit according to the second embodiment, which is continued from the operation in FIG. 27A to FIG. 27E;

FIG. 28C is a front view illustrating operation of the extracting unit according to the second embodiment, which is continued from the operation in FIG. 27A to FIG. 27E;

FIG. 28D is a front view illustrating operation of the extracting unit according to the second embodiment, which is continued from the operation in FIG. 27A to FIG. 27E;

FIG. 28E is a front view illustrating operation of the extracting unit according to the second embodiment, which is continued from the operation in FIG. 27A to FIG. 27E;

FIG. 28F is a front view illustrating operation of the extracting unit according to the second embodiment, which is continued from the operation in FIG. 27A to FIG. 27E;

FIG. 30A is a diagram for explaining the flow of entire main operation of the medication support apparatus according to the second embodiment;

FIG. 30B is a diagram for explaining the flow of the entire main operation of the medication support apparatus according to the second embodiment;

FIG. 30C is a diagram for explaining the flow of the entire main operation of the medication support apparatus according to the second embodiment;

FIG. 30D is a diagram for explaining the flow of the entire main operation of the medication support apparatus according to the second embodiment;

FIG. 30E is a diagram for explaining the flow of the entire main operation of the medication support apparatus according to the second embodiment;

FIG. 31 is a flowchart for explaining a timing at which a posture of an attracting unit of the extracting unit according to the second embodiment is changed.

The accompanying drawings are intended to depict exemplary embodiments of the present invention and should not be interpreted to limit the scope thereof. Identical or similar reference numerals designate identical or similar components throughout the various drawings.

DESCRIPTION OF THE EMBODIMENTS

Figure 2A:
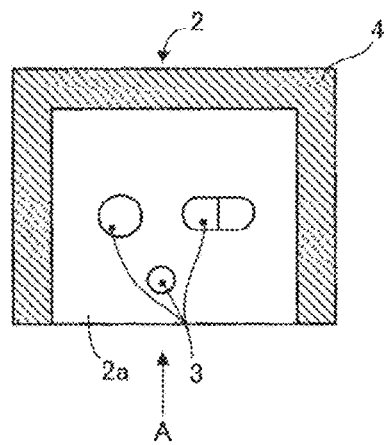
FIG. 2A is a plan view illustrating a general configuration of a single one-dose package.

The terminology used herein is for the purpose of describing particular embodiments only and is not intended to be limiting of the present invention.

As used herein, the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

An embodiment of the present invention will be described in detail below with reference to the drawings.

An embodiment has an object to provide an apparatus that has a simple structure and that reduces time and effort for a medicated person or a medication assistant who assists medication to perform medication.

Embodiments of the present invention including examples will be described in detail below with reference to the drawings. In each of the embodiments and the examples, structural elements (members and components) and the like that have the same functions, shapes, and the like are denoted by the same reference symbols after being explained once and explanation of the same structural elements is not repeated as long as there is no likelihood of confusion.

First Embodiment

An entire main configuration of a medication support apparatus according to a first embodiment of the present invention will be described below with reference to FIG. 1A and FIG. 1B. FIG. 1A is a front view schematically illustrating an entire main configuration of a medication support apparatus according to one embodiment of the present invention, and FIG. 1B is a side view schematically illustrating a lateral configuration of FIG. 1A.

As illustrated in FIG. 1A and FIG. 1B, a medication support apparatus 200 according to one embodiment of the present invention includes storage units 10, medicine distribution trays 30, an extracting unit 50, a transfer unit 90, a first gateway portion 41, second gateway portions 42, third gateway portions 43, and a fourth gateway portion 44.

In FIG. 1A and FIG. 1B, a left-right direction or a lateral direction (width direction) of the medication support apparatus 200 is referred to as an X direction, a front-back direction or a depth direction is referred to as a Y direction, an up-down direction or a longitudinal direction (vertical direction) is referred to as a Z direction.

Each of the storage units 10 functions as a storage means for storing a one-dose package (hereinafter, may also be simply referred to as a "package"), in which medicines are packed, in a stacked manner. The storage units 10 are arranged at a plurality of positions in each of an uppermost portion and a lower portion inside a main-body frame 199 that is an apparatus main body of the medication support apparatus 200. Here, "storing in the stacked manner" means that packages are stored in an approximately horizontal state or a flatly laid out state.

Each of the medicine distribution trays 30 functions as a medicine distribution means or a medicine distribution board on which a specific package that is transferred by the transfer unit 90 is placed. As illustrated in FIG. 1A, the four medicine distribution trays 30 are arranged between the storage units 10 in the uppermost portion and the lower portion. Hereinafter, portions in which the medicine distribution trays 30 are set (portions in which packages are delivered such that medicines are automatically distributed to the medicine distribution trays 30) will be referred to as medicine distribution Portions 29.

The extracting unit 50 functions as an extracting means for extracting specific packages from the storage units 10.

The transfer unit 90 functions as a transfer means for transferring the packages that are extracted by the extracting unit 50 from the storage units 10.

Each of the first gateway portion 41 and the fourth gateway portion 44 functions as a gateway means for the storage means to allow the storage units 10 to enter and exit from the main-body frame 199. When the storage units 10 are inserted and set in the main-body frame 199, operation is performed through the first gateway portion 41 and the fourth gateway portion 44. Open-close doors of the first gateway portion 41 and the fourth gateway portion 44 are opened, drawn units 21 on which the storage units 10 are set are drawn in a forward direction, and the storage units 10 are detached and attached.

Each of the second gateway portions 42 and the third gateway portions 43 functions as a gateway means for the medicine distribution means to allow the medicine distribution trays 30 to enter and exit from the main-body frame 199. The second gateway portions 42 and the third gateway portions 43 are arranged such that packages can be extracted immediately after the packages are arranged (hereinafter, also referred to as "set" or "inserted") on the medicine distribution trays 30.

In the medication support apparatus 200, the four medicine distribution trays 30 are arranged as described above, and, for example, the medicine distribution trays are arranged for respective medication timings, such as morning, daytime, evening, and before bedtime.

The second gateway portions 42 and the third gateway portions 43 for the medicine distribution trays are arranged for the respective medicine distribution trays, so that even when medicine distribution operation is performed on a certain medicine distribution tray, it is possible to extract a different medicine distribution tray.

Meanwhile, the drawn units 21 for the storage units 10 illustrated in FIG. 1A and FIG. 1F are arranged at two positions of two stages on the upper and the lower sides sandwiching the four medicine distribution trays 30 therebetween, but embodiments are not limited to this example, and the drawn units may collectively arranged on the upper side or the lower side. Furthermore, it may be possible to achieve the same effects by arranging the storage units 10 on three stages, depending on the number of persons in a nursing home.

Figure 2B:
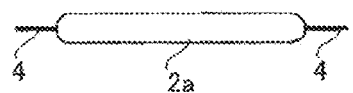
FIG. 2B is a side view of the one-dose package when viewed in a direction of arrow A in FIG. 2A.
Figure 2C:
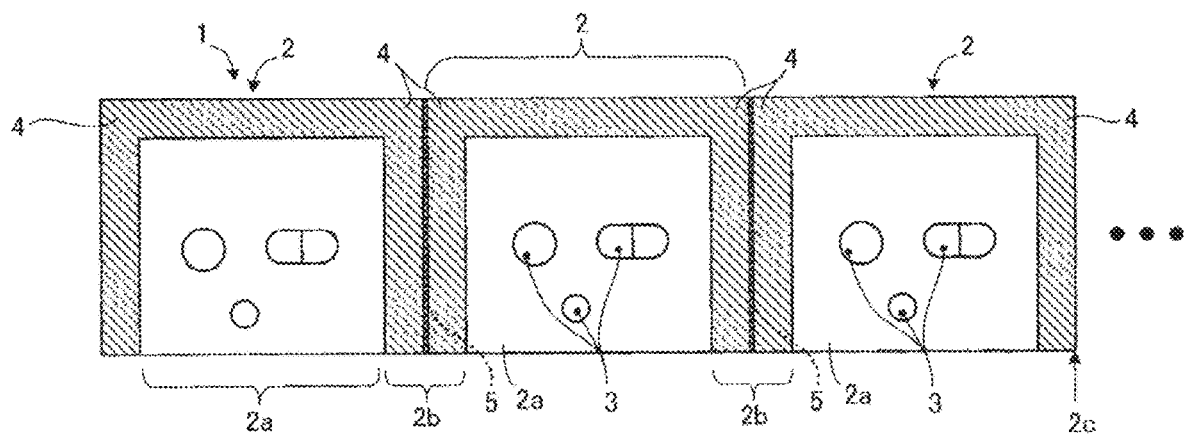
FIG. 2C is a diagram illustrating a general configuration of a package continuum.

An overview of a single one-dose package as an objective of the present invention will be described below with reference to FIGS. 2A to 2C. FIG. 2A is a plan view illustrating a general configuration of a single one-dose package, FIG. 2B is a side view of the one-dose package when viewed in a direction of arrow A in FIG. 2A, and FIG. 2C is a diagram illustrating a general configuration of a package continuum. Meanwhile, in FIG. 2B, illustration of the medicines are omitted and relatively schematic illustration is provided.

As illustrated in FIG. 2A, a single one-dose package 2 is made with, for example, a resin film, and is formed by packing medicines 3, such as a capsule and a pill, in a small bag. The one-dose package 2 includes a bag portion 2a that covers the medicines 3, and a crimp portion 4 in which three sides indicated by hatching are crimped or welded. A side on the bag portion 2a side is generally half folded, the medicines 3 are sandwiched between folded portions, and the crimp portion 4 serves as a spill preventive portion that prevents the medicines 3 from being spilled from the bag portion 2a. The single one-dose package 2 is generally generated for each dose of medicines for a medicated person.

As illustrated in FIG. 2C, the one-dose packages 2 are generated (divided and packed) by a medicine dividing and packing machine that is installed in a pharmacy or the like. Dividing and packing paper (dividing and packing sheet) used for dividing and packing is a rolled long sheet that has a crease and that is rolled in an overlapping manner, and the medicines 3 to be taken are sandwiched between sheets. Three sides other than the crease around the medicines 3 are sealed and divided by the crimp portion 4 repeatedly for a plurality of doses, and a continuous sheet for a certain number of medications is formed. The one-dose packages in the continuous sheet will be referred to as a "package continuum". A package continuum 1 illustrated in FIG. 2C includes the plurality of one-dose packages 2 (in the example illustrated in the figure, for three doses) are continued in a belt-like manner. In general, the package continuum 1 is a typical form that is provided and sold to a user (including a person who actually takes medicines in one-dose packages and an assistant or a supporter who assists or supports medication) in a pharmacy or the like, or staff (which is a concept including a pharmacist, a nurse, a caregiver, and a medication assistant) in various nursing homes and medical facilities. For the sake of simplification of explanation, in the following description, it is assumed that medicines in the same form (a capsule, a pill, or the like) are enclosed in a single package, but it is of course possible to enclose medicines in different forms in a single package depending on usage, a purpose, or the like of a user.

The one-dose package 2 has a rectangular shape in a planer view in the examples illustrated in FIG. 2A to FIG. 2C, and, a packaging method of crimping and sealing the three sides as in the examples is generally called a three-side seal packaging, and almost all medicine dividing and packing machines on the market perform packaging by using this method.

The crimp portion 4 has a belt-like shape with a width of about 10 millimeters (mm) to 15 mm, and has higher rigidity than the bag portion 2a that is a transparent or semi-transparent film portion in which the medicines 3 can be viewed. In a central portion between the crimp portions 4 of the successively adjacent one-dose packages 2 from an upstream side to a downstream side of the plurality of one-dose packages 2 in the package continuum 1, a boundary portion 2b with a perforation 5 is formed. A user or the like who can freely use his/her hands tears the perforation 5 with his/her finger or cuts a portion around the perforation 5 with scissors, a special cutter, or the like to obtain the single one-dose package 2.

Figure 3:
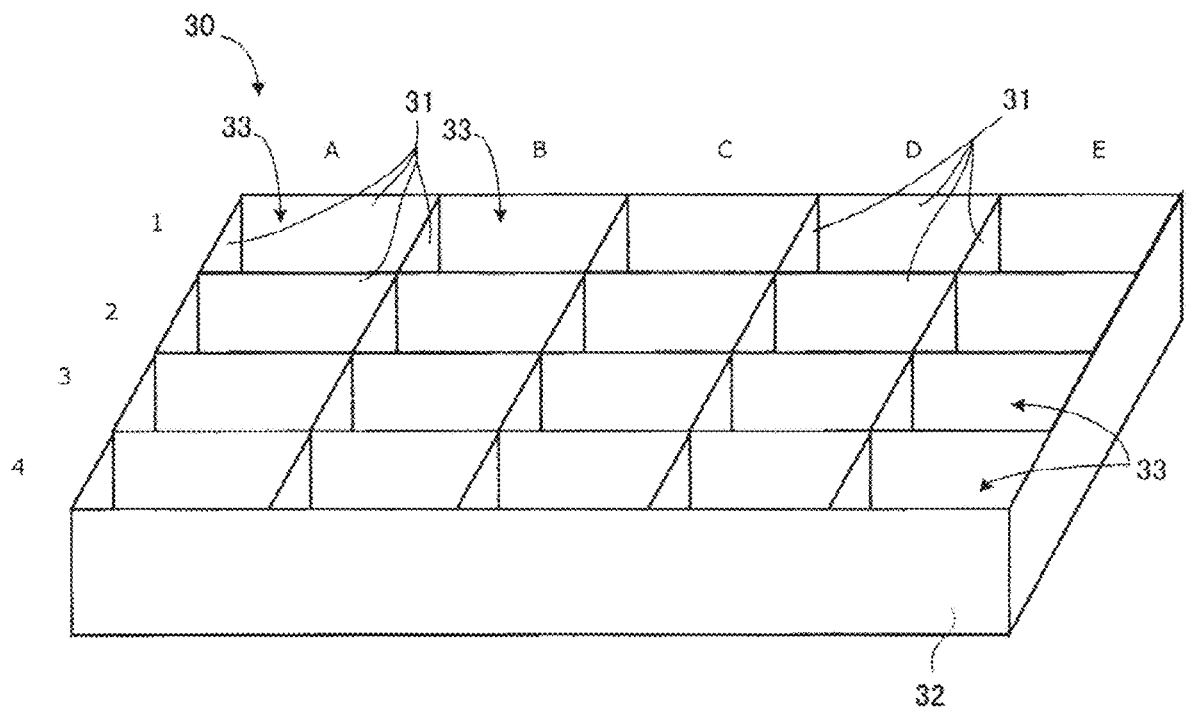
FIG. 3 is an external perspective view illustrating a configuration of a medicine distribution tray.

One example of the medicine distribution tray will be described below with reference to FIG. 3. FIG. 3 is an external perspective view illustrating a configuration of the medicine distribution tray.

As illustrated in FIG. 3, the medicine distribution tray 30 includes partition walls 31 that are partition members as a plurality of partitions for arranging specific packages, and is partitioned by the four standing partition walls 31. In the example illustrated in the figure, the medicine distribution tray 30 includes a total of 20 sections 33 that are divided by the plurality of partition walls 31. In other words, the medicine distribution tray 30 is configured to arrange a specific package in the predetermined (specific) section 33 that is divided by the plurality of partitions.

The sections 33 at the 20 positions in the medicine distribution tray 30 are represented as elements of a matrix formed of five columns A, B, C, D, and E in the longitudinal direction (line spacing direction) and four rows 1, 2, 3, and 4 in the lateral direction (character feed direction). With this configuration, each of the sections 33 at the 20 positions in the medicine distribution tray 30 can be uniquely positioned by each of the elements (hereinafter, also referred to as block numbers) of the matrix of five columns and four rows. Furthermore, the medicine distribution tray 30 includes a bottom wall 32 on which the arranged packages (not illustrated) are placed. In this manner, the medicine distribution tray 30 is configured such that, by the plurality of (four) partition walls 31 and the common bottom wall 32, a specific package (not illustrated) arranged in the specific section 33 is not mixed with packages (not illustrated) in the other sections 33 and such that the specific package is reliably arranged inside the specific section 33 without falling from the bottom wall 32.

The medicine distribution tray 30 includes the total of 20 sections 30 that are divided by the plurality of partition walls 31, and a set or insertion position of a package to be taken is determined for each of medicated persons. In other words, the plurality of sections 33 in the medicine distribution tray 30 may be assigned to different medicated persons for the same medication timing. Furthermore, if a specific medicated person does not take a medicine at a specific medication timing, it is possible to prevent a package from being arranged for the specific medicated person at the specific medication timing.

According to the medicine distribution tray 30 illustrated in FIG. 3, by determining each of the sections for each of medicated persons, it is possible to allow staff or the like who assists medication using the medicine distribution tray 30 in a nursing home or the like to take a package in the same section (block number) at each time, so that it is possible to prevent a medication error. In other words, the sections are not changed day by day, so that it is possible to reduce operation of staff in a nursing home, a welfare institution, or the like.

Embodiments are not limited to the medicine distribution tray 30 as described above, and the plurality of sections 33 in the medicine distribution tray 30 may be assigned for each of medication timings for each of medicated persons. Specifically, the plurality or sections 33 may be assigned for each of medication timings, such as in the morning, in the daytime, in the evening, and before bedtime, at which the packages 2 are taken and for each of medicated persons. With the medicine distribution tray 30 in the example as described above, it is possible to manage the medicine distribution tray 30 for each of floors or each of rooms in which a plurality of medicated persons reside, and distribute, in advance, the packages 2 for a certain day (or for several days) to the medicine distribution tray 30.

According to the example as described above, by assigning each of the sections to each of medication timings, such as morning, daytime, evening, and before bedtime, it is possible to prevent mistakes about medication timings for each of medicated persons. Various examples may be made by combinations of medicated persons and medication times in addition to the configuration example of the medicine distribution tray 30 as described above, but various examples go beyond the disclosure of the present invention, and therefore, explanation is confined to the above-described example.

One example of the storage unit will be described below with reference to FIG. 4A and FIG. 4B. FIG. 4A is a bottom view of the storage unit, and FIG. 4B is a vertical cross-sectional view of FIG. 4A. Meanwhile, in the vertical cross-sectional view in FIG. 4B, for the sake of simplification of the figure, portions of the crimp portions 4 of the packages 2 stored in the storage unit 10 are purposely omitted and the packages 2 are illustrated in a schematically and exaggeratedly enlarged manner. Furthermore, for the same purpose, hatching on cross sections of the support units (a left support unit 12, a right support unit 13, and the like) is also omitted.

The storage unit 10 mainly includes a case portion 11, a cap portion 14, a package extraction opening 17, a movable plate 16, a package posture retaining unit 15, and the left support unit 12 and the right support unit 13 serving as support units.

The case portion 11 has a function to store therein the plurality of packages 2. The case portion 11 is integrally or separately formed by using resin, for example.

The cap portion 14 has a function to allow the packages 2 to be taken in and out.

The package extraction opening 17 is formed in a lower portion or a bottom portion of the case portion 11, is an opening for extracting the packages in the storage unit 10, and has a function to allow passage of the packages 2 that are extracted from the storage unit 10 by the extracting unit 50 (see FIG. 1A or the like, a detailed configuration and operation thereof will be described later).

The movable plate 16 has a function to prevent the packages 2 from falling over, and to move the package 2 in the lowermost portion to the vicinity of the package extraction opening 17 after the first package among the maximum number of packages 2 that can be stored in the case portion 11 is extracted.

The package posture retaining unit 15 has a function to retain postures of the packages 2.

The left support unit 12 and the right support unit 13 have functions to support or hold the packages 2 inside the case portion 11.

In this example, an extraction portion 20 for the package 2 to be extracted from the storage unit 10 by the extracting unit 50 (see FIG. 1A or the like) is located in a lower portion or a bottom portion inside the storage unit 10. In other words, the extraction portion 20 includes the left support unit 12 and the right support unit 13, which serve as support units or support members that support a plurality of portions of the package 2 to be extracted from the storage unit 10, and includes the package extraction opening 17.

In this example, the left support unit 12 has a movable flap mechanism, and makes it possible to smoothly extract the package 2 that is to be extracted by the extracting unit 50. The left support unit 12 is arranged, in an openable and closable manner, in an end portion of a left bottom wall of the package extraction opening 17 that is opened on a bottom wall of the case portion 11. The left support unit 12 is arranged so as to be opened and closed by swinging around a rotary shaft 12a that is arranged on the end portion of the left bottom wall of the package extraction opening 17.

The left support unit 12 and the right support unit 13 are made of, for example, resin, metal, or the like.

In other words, the left support unit 12 is configured to allow passage of the package 2 when the extracting unit 50 extracts the package 2 from the storage unit 10. In contrast, the left support unit 12 is configured to restrict passage of the package 2 and keep storing the plurality of packages 2 in the case portion when the package 2 is not extracted from the storage unit 10.

Specifically, a torsion coil spring with biasing force in a predetermined range is attached between the rotary shaft 12a of the left support unit 12 and the end portion of the left bottom wall. The biasing force is set such that the left support unit 12 allows passage of the package 2 when the extracting unit 50 extracts the package 2 from the storage unit 10 and such that the maximum number of packages 2 stored in the case portion 11 and the movable plate 16 are kept stored when the package 2 is not extracted from the storage unit 10.

The right support unit 13 is arranged on an end portion of a right bottom wall of the package extraction opening 17. The right support unit 13 is formed by an elastic member that is elastically deformable, and makes it possible to smoothly extract the package 2 that is to be extracted by the extracting unit 50, in cooperation with the left support unit 12. As the elastic member, a plate material made of elastically deformable resin, metal, or the like is used.

As described above, in the lower portion of the storage unit 10, the package extraction opening 17 for extracting the package 2 and each of the left support unit 12 and the right support unit 13 that support the package 2 in the storage unit 10 and that are openable and closable by the operation of extracting the package 2 from the storage unit 10 by the extracting unit 50, as will be described in detail later in relation to a configuration and operation of the extracting unit 50 to be described later.

A projection 12b that has a projecting shape and that overlaps with the package 2 in a planar view is formed in an approximately central portion of the left support unit 12 in the the Y direction. The left support unit 12 supports the package 2 only by the projection 12b that is a partially formed region.

In the storage unit 10 illustrated in the figure, positions at which the package 2 stored in the storage unit 10 is attracted by attraction pads 52 (hereinafter, also referred to as "attraction pad positions") as illustrated in FIG. 17, FIGS. 18A to 18F, etc. to be described later are indicated by circles in chain double-dashed lines.

To prevent the package 2 in the storage unit 10 from falling from the package extraction opening 17, the left support unit 12 having a flap mechanism and the right support unit 13 made with an elastic member support the package 2 in the storage unit 10. Furthermore, as will be described in detail later in relation to the configuration and the operation of the extracting unit 50, a positional relationship in which, when the package 2 in the lowermost Portion in the storage unit 10 is extracted by being attracted by the attraction pads 52, the package 2 is attracted by the attraction pads 52 at the two attraction pad positions across the projection 12b in the Y direction is achieved. In other words, when the package 2 in the lowermost portion is extracted from the storage unit 10 by the attraction pads 52, the two attraction pads 52 pass by near both ends of the projection 12b of the left support unit 12 and then attract and hold the package 2.

In the example illustrated in FIG. 4A, by arranging the attraction pad positions in the two portions near the both ends of the projection 12b of the left support unit 12 in the Y direction, it is passible to prevent occurrence of a defect in which attraction by the attraction pads 52 is disabled, and it is possible to extract the package 2 while minimizing deformation. In other words, the package 2 is attracted by the attraction pads 52 at the both sides of the projection 12b in the Y direction, so that the film of the package 2 is stretched and can resist deformation. With this configuration, it is possible to reliably support or hold the one-dose package in the storage unit, and at the same time, it is possible to smoothly extract the one-dose package.

The package posture retaining unit 15 is made of sponge rubber with appropriate elasticity. The movable plate 16 is made of, for example, resin, metal, or the like. The package posture retaining unit 15 and the movable plate 16 accurately retain postures of the plurality of packages 2 stored in the case portion 11 (as illustrated in FIG. 4B, retain the postures of the packages 2 orderly and approximately horizontally along the Z direction).

To implement the function as described above, the movable plate 16 is set so as to move downward in the Z direction inside the case portion 11 by own weight to thereby reliably move at least the single package 2 that is left in the case portion 11 to the vicinity of the package extraction opening 17.

As illustrated in FIG. 4B, a long gutter 11a that has a predetermined width in the X direction and that extends in the Z direction is formed on a side wall of the case portion 11, A shaft 16a with a flange is arranged on one end portion of the movable plate 16 so as to protrude from the long gutter 11a. The shaft 16a is guided in the Z direction along the long gutter 11a, so that the movable plate 16 is able to retain the postures of the packages 2 orderly and approximately horizontally along the Z direction. As illustrated in FIG. 4A, the packages 2 in the storage unit 10 are stored in an approximately horizontal state in a stacked manner.

The packages 2 are set in the case portion 11 sequentially and in an upward direction from the package extraction opening 17 on the left support unit 12 and the right support unit 13 side.

A timing of replenishing the storage unit 10 with the packages 2 may be set to, for example, a medical examination timing (normally every two weeks) for a medicated person (resident) in a nursing home or the like or a timing at which no package 2 is left in the storage unit 10. If the package 2 is left in the storage unit 10 at the time of replenishment, replenishment is performed following behind the remaining package 2.

The setting of the package 2 and the replenishment With the package 2 with respect to the storage unit 10 as described above are performed by staff or the like in a nursing home or the like, but need not always be performed in the above-described manner if a configuration in which the storage unit is formed as a cartridge and is automated is adopted.

The cap portion 14 allows staff or the like in a nursing home or the like to take in and out the packages 2 stored in the storage unit 10, and, as illustrated in FIG. 4B, is formed so as to be elongated over the case portion 11 in the Z direction and have a predetermined opening width.

As illustrated in FIG. 4B, the plurality of packages 2 are stored in the storage unit 10, and, as a type of the packages 2, the packages are classified for each of medication timings, such as packages to be taken in the morning by a person A for 14 days. Therefore, if the person A takes medicines in the daytime, in the evening, and before bedtime in addition to the morning time, a total of four storage units are needed.

Embodiments are not limited to the example as described above; for example, it may be possible to use the single storage unit 10 that is set for each of medicated persons (persons), and the packages may be arranged in order of packages to be taken in the morning, in the daytime, in the evening, and before bedtime on a first day, packages to be taken in the morning, in the daytime, in the evening, and before bedtime on a second day, . . . in an upward direction from the package extraction opening 17 that is a package extraction direction of the storage unit 10.

The extraction portion 20 of the storage unit 10 illustrated in FIGS. 4A and 4B is one example, and it may be possible to adopt a combination of the left support unit and the right support unit, or it may be possible to adopt a support unit including a single elastic member. Details of configurations and operation of other examples go beyond the disclosure of the present invention, and therefore, explanation thereof is omitted.

First Example

A storage unit according to a first example will be described below with reference to FIG. 5A and FIG. 5B. FIG. 5A is a bottom view of the storage unit according to the first example, and FIG. 5B is a vertical cross-sectional view of the storage unit in FIG. 5A. Meanwhile, in the vertical cross-sectional view in FIG. 5B, for the sake of simplification of the figure, portions of the crimp portions 4 of the packages 2 stored in the storage unit 10 are purposely omitted and the packages 2 are illustrated in a schematically and exaggeratedly enlarged manner (the same applies to vertical cross-sectional views in other examples to be described below). Furthermore, for the same purpose, hatching on cross sections of the support units (the left support unit 12, the right support unit 13, and the like) is also omitted.

The storage unit 10 mainly includes the case portion 11, the cap portion 14, the package extraction opening 17, the movable plate 16, the package posture retaining unit 15, and the left support unit 12 and the right support unit 13 serving as the support unit.

The case portion 11 has a function to store therein the plurality of packages 2. The case portion 11 is integrally or separately formed by using resin, for example.

The cap portion 14 has a function to allow the packages 2 to be taken in and out.

The package extraction opening 17 has a function to allow passage of the packages 2 that are extracted from the storage unit 10 by the extracting unit 50 (see FIG. 1A or the like, a detailed configuration and operation thereof will be described later).

The movable plate 16 has a function to prevent the packages 2 from falling over, and to move the package 2 in the lowermost portion to the vicinity of the package extraction opening 17 after the first package among the maximum number of the packages 2 that can be stored in the case portion 11 is extracted.

The package posture retaining unit 15 has a function to retain the postures of the packages 2.

The left support unit 12 and the right support unit 13 have functions to support or hold the packages 2 inside the case portion 11.

A main feature of the present invention is that the extraction portion 20 for the package 2 to be extracted from the storage unit 10 by the extracting unit 50 (see FIG. 1A or the like) is located in a lower portion or a bottom portion inside the storage unit 10. In other words, the extraction portion 20 is arranged in the lower portion inside the storage unit 10, includes the left support unit 12 and the right support unit 13, which serve as support units or support members that support a plurality of portions of the package 2 to be extracted from the storage unit 10, and includes the package extraction opening 17.

In this example, the left support unit 12 has a movable flap mechanism, and makes it possible to smoothly extract the package 2 that is to be extracted by the extracting unit 50. The left support unit 12 is arranged, in an openable and closable manner, in the end portion of the left bottom wall of the package extraction opening 17 that is opened on the bottom wall of the case portion 11. The left support unit 12 is arranged so as to be opened and closed by swinging around the rotary shaft 12a that is arranged on the end portion of the left bottom wall of the package extraction opening 17.

The left support unit 12 and the right support unit 13 are made of, for example, resin, metal, or the like.

In other words, the left support unit 12 is configured to allow passage of the package 2 when the extracting unit 50 extracts the package 2 from the storage unit 10. In contrast, the left support unit 12 is configured to restrict passage of the package 2 and keep storing the plurality of packages 2 in the case portion when the package 2 is not extracted from the storage unit 10.

Specifically, a torsion coil spring with a biasing force in a predetermined range is attached between the rotary shaft 12a of the left support unit 12 and the end portion of the left bottom wall. The biasing force is set such that the left support unit 12 allows passage of the package 2 when the extracting unit 50 extracts the package 2 from the storage unit 10 and such that the maximum number of packages 2 stored in the case portion 11 and the movable plate 16 are kept stored when the package 2 is not extracted from the storage unit 10.

The right support unit 13 is arranged on the end portion of the right bottom wall of the package extraction opening 17 in an immobile manner. The right support unit 13 may be formed integrally with the case portion 11.

The projection 12b that has a projecting shape and that overlaps with the package 2 in a planar view is formed in an approximately central portion of the left support unit 12 in the the Y direction. The left support unit 12 supports the package 2 only by the projection 12b that is a partially formed region. This will be described in detail later in relation to the attraction pad positions in the detailed configuration and the operation of the extracting unit 50.

The package posture retaining unit 15 is made of sponge rubber with appropriate elasticity. The movable plate 16 is made of, for example, resin, metal, or the like. The package posture retaining unit 15 and the movable plate 16 accurately retain the postures of the plurality of packages 2 stored in the case portion 11 (as illustrated in FIG. 5B, retain the postures of the packages 2 orderly and approximately horizontally along the Z direction).

To implement the function as described above, the movable plate 16 as set so as to move downward in the Z direction inside the case portion 11 by own weight to thereby reliably move at least the single package 2 that is left in the case portion 11 to the vicinity of the package extraction opening 17.

As illustrated in FIG. 5B, the long gutter 11a that has a predetermined width in the X direction and that extends in the Z direction is formed on the side wall of the case portion 11. The shaft 16a with a flange is arranged on one end portion of the movable plate 16 so as to protrude from the long gutter 11a. The shaft 16a is guided in the Z direction along the long gutter 11a, so that the movable plate 16 is able to retain the postures of the packages 2 orderly and approximately horizontally along the Z direction.

The packages 2 are set in the case portion 11 sequentially and in an upward direction from the package extraction opening 17 on the left support unit 12 and the right support unit 13 side.

A timing of replenishing the storage unit 10 with the packages 2 may be set to, for example, a medical examination timing (normally every two weeks) for a medicated person (resident) in a nursing home or the like or a timing at which no package 2 is left in the storage unit 10. If the package 2 is left in the storage unit 10 at the time of replenishment, replenishment is performed in sequence from the back of the remaining package 2.

The setting of the package 2 and the replenishment with the package 2 with respect to the storage unit 10 as described above are performed by staff or the like in a nursing home or the like, but need not always be performed in the above-described manner if a configuration in which the storage unit is formed as a cartridge and is automated is adopted.

The cap portion 14 allows staff or the like in a nursing home or the like to take in and out the packages 2 stored in the storage unit 10, and, as illustrated in FIG. 5B, is formed so as to be elongated over the case portion 11 in the Z direction and have a predetermined opening width.

As illustrated in FIG. 5B, the plurality of packages 2 are stored in the storage unit 10, and, as a type of the packages 2, the packages are classified for each of medication timings, such as packages to be taken in the morning by a person A for 14 days. Therefore, if the person A takes medicines in the daytime, in the evening, and before bedtime in addition to the morning time, a total of four storage units are needed.

Embodiments are not limited to the example as described above; for example, it may be possible to use the single storage unit 10 that is set for each of medicated persons (persons), and the packages may be arranged in order of packages to be taken in the morning, in the daytime, in the evening, and before bedtime on a first day, packages to be taken in the morning, in the daytime, in the evening, and before bedtime on a second day, . . . in an upward direction from the package extraction opening 17 that is a package extraction direction of the storage unit 10.

In the first example as described above, in the flap mechanism that allows the left support unit 12 to move (swing, open, and close), a simple structure using the biasing force of the torsion coil spring is adopted; however, it may be possible to adopt a flat spring or an electric motor depending on usage or purposes.

Second Example

A storage unit according to a second example will be described below with reference to FIG. 6A and FIG. 6B. FIG. 6A is a bottom view of the storage unit according to the second example, and FIG. 6B is a vertical cross-sectional view of FIG. 6A.

A storage unit 10 of the second example illustrated in FIGS. 6A and 6B is different from the storage unit 10 of the first example illustrated in FIG. 5A and FIG. 5B only in that the right support unit 13 has a flap mechanism similarly to the left support unit 12 to make it possible to smoothly extract the package 2 that is extracted by the extracting unit 50. The right support unit 13 is arranged, in an openable and closable manner, in the end portion of the right bottom wall of the package extraction opening 17 that is opened on the bottom wall of the case portion 11. The right support unit 13 is arranged so as to be opened and closed by swinging around a rotary shaft 13a that is arranged on the end portion of the right bottom wall of the package extraction opening 17.

In other words, similarly to the left support unit 12, the right support unit 13 is configured to allow passage of the package 2 when the extracting unit 50 extracts the package 2 from the storage unit 10. In contrast, the right support unit 13 is configured to restrict passage of the package 2 and keep storing the plurality of packages 2 in the case portion when the package 2 is not extracted from the storage unit 10.

Specifically, a torsion coil spring with a biasing force in a predetermined range is attached between the rotary shaft 13a of the right support unit 13 and the end portion of the right bottom wall. The biasing force is Set such that, in cooperation with the left support unit 12, the right support unit 13 allows passage of the package 2 when the extracting unit 50 extracts the package 2 from the storage unit 10 and such that the maximum number of packages 2 stored in the case portion 11 and the movable plate 16 are kept stored when the package 2 is not extracted from the storage unit 10.

According to the first and the second examples, firstly, the extraction portion in the storage unit includes the support units that support the one-dose package at a plurality of positions, so that it is possible to store the one-dose package in the storage unit, and it is possible to simultaneously realize easy extraction of the one-dose package and prevention of falling of the one-dose package.

Secondly, the single storage unit includes the plurality of support units, and at least one of the support units is movable, so that it is possible to smoothly extract the one-dose package.

Third Example

A storage unit according to a third example will be described below with reference to FIG. 7A and FIG. 7B. FIG. 7A is a bottom view of the storage unit according to the third example, and FIG. 7B is a vertical cross-sectional view of FIG. 7A.

A storage unit 10 of the third example illustrated in FIG. 7A and FIG. 7B is different from the storage unit 10 of the first example illustrated in FIG. 5A and FIG. 5B only in that the support unit includes a left support unit 12A that is formed by an elastic member that is elastically deformable, instead of the left support unit 12 that is movable using a flap mechanism.

As the elastic member, for example, a resin plate member that is elastically deformable, a metal plate member that is made of stainless steel, aluminum, etc., and that is elastically deformable, or the like may be used.

According to the third example, firstly, the extraction portion in the storage unit includes the support units that support the one-dose package at a plurality of positions, so that it is possible to store the one-dose package in the storage unit, and it is possible to simultaneously realize easy extraction of the one-dose package and prevention of falling of the one-does package.

Secondly, even without using the left support unit that is movable using a flap mechanism, it is possible to smoothly extract the one-dose package because of elastic deformation of the left support unit, so that it is possible to simplify the structure.

Fourth Example

A storage unit according to a fourth example will be described with reference to FIG. 8A and FIG. 8B. FIG. 8A is a bottom view of the storage unit according to the fourth example, and FIG. 8B is a vertical cross-sectional view of FIG. 8A.

A storage unit 10 of the fourth example illustrated in FIG. 8A and FIG. 8B is different from the storage unit 10 of the first example illustrated in FIG. 5A and FIG. 5B only in that the support unit includes a right support unit 13A that is formed by an elastic member that is elastically deformable, instead of the right support unit 13 that is an immobile member.

As the elastic member, a plate material made with elastically deformable resin, metal, or the like may be used, similarly to the third example.

According to the fourth example, firstly, the extraction portion in the storage unit includes the support units that support the one-dose package at a plurality of positions, so that it is possible to store the one-dose package in the storage unit, and it is possible to simultaneously realize easy extraction of the one-dose package and prevention of falling of the one-does package.

Secondly, it is possible to smoothly extract the one-dose package because of elastic deformation of the right support unit, so that it is possible to simplify the structure.

Another example in which both of the left support unit and the right support unit as the plurality of support units are formed by elastic members may be adopted, in addition to the first to the fourth examples as described above.

In the first to the fourth examples as described above, aspects in which the storage unit includes the plurality of support units have been described; however, it may be possible to provide a single support unit as described in a fifth example and a sixth example below.

Fifth Example

A storage unit according to a fifth example will be described with reference to FIG. 9A and FIG. 9B. FIG. 9A is a bottom view of the storage unit according to the fifth example, and FIG. 9B is a vertical cross-sectional view of FIG. 9A.

Figure 9B:
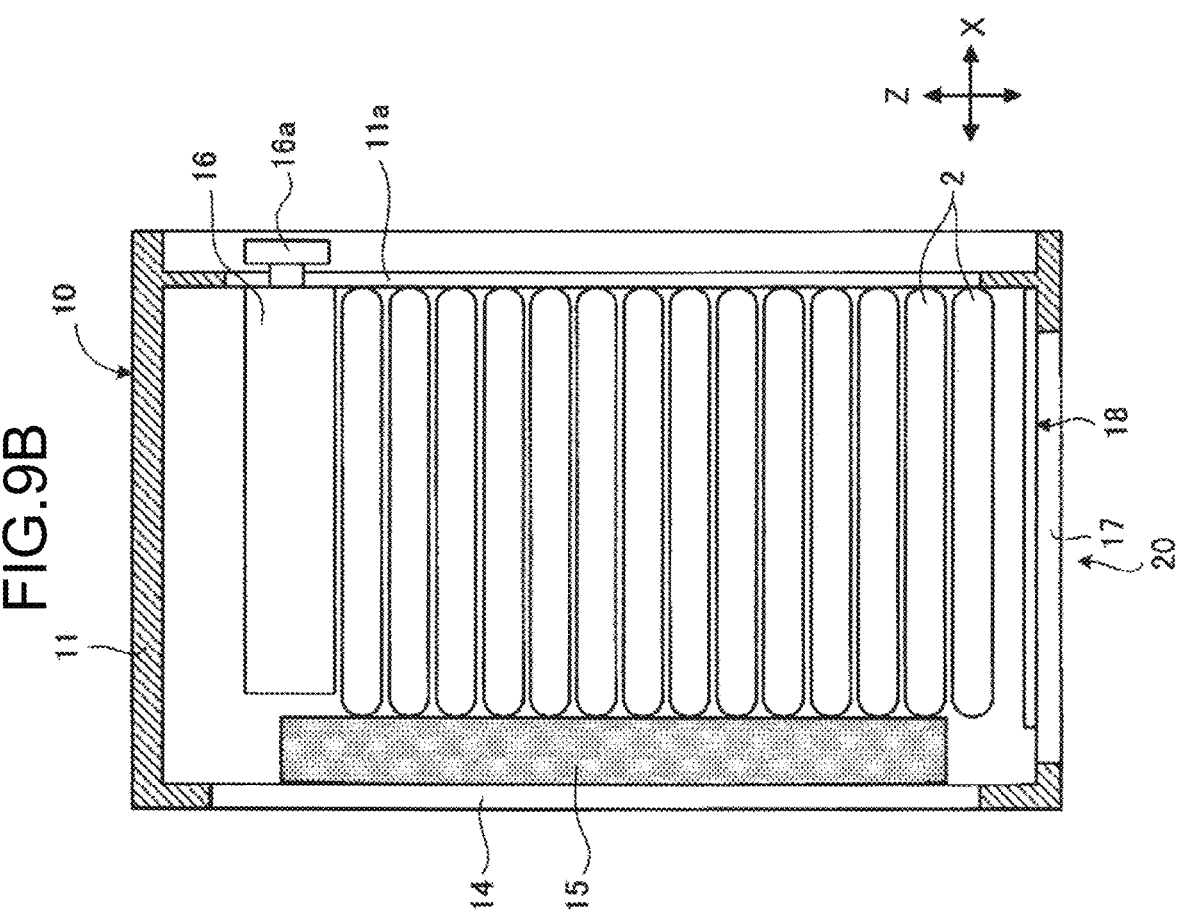
FIG. 9B is a vertical cross-sectional view of FIG. 9A.
Figure 9A:
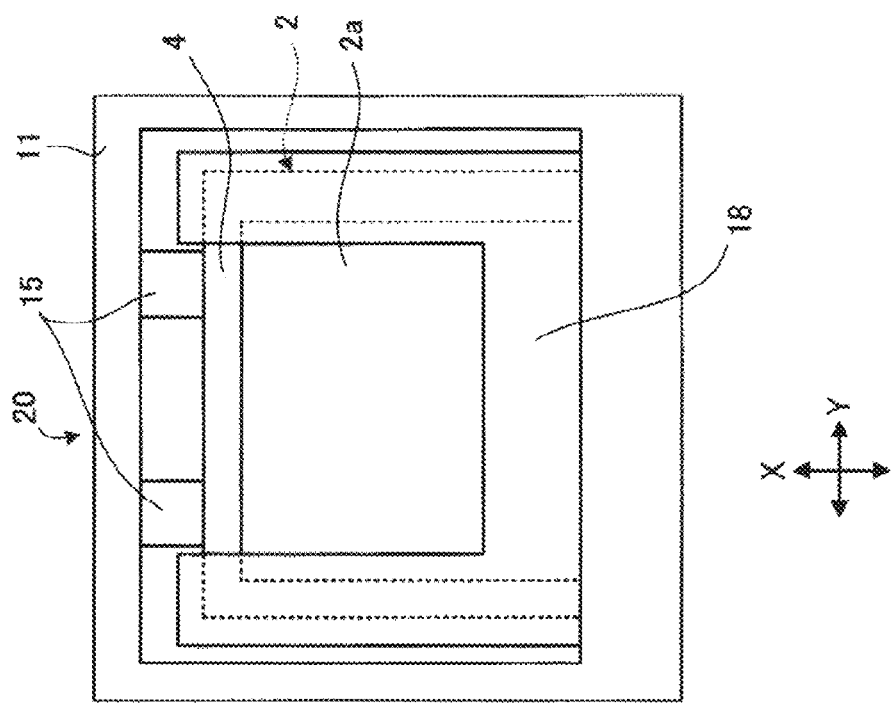
FIG. 9A is a bottom view of a storage unit according to a fifth example.

A storage unit 10 of the fifth example illustrated in FIG. 9A and FIG. 9B is different from the storage unit 10 of the first example illustrated in FIG. 5A and FIG. 5B only in that the storage unit includes a single support unit 18 instead of the left support unit 12 and the right support unit 13. As the single support unit 18, it is preferable to use an elastic member to smoothly extract the package 2.

The support unit 18 is configured to be elastically deformed and allow passage of the package 2 when the extracting unit 50 extracts the package 2 from the storage unit 10. In contrast, the support unit 18 is configured to be elastically recovered, restrict passage of the package 2, and keep storing the plurality of packages 2 in the case portion 11 when the package 2 is not extracted from the storage unit 10. A range of an elastic force of the support unit 18, a specific material of the support unit 18, and the like are specifically set by taking into account the above-described configurations.

According to the fifth example, firstly, the extraction portion in the storage unit includes the support unit that supports the one-dose package at a plurality of positions, so that it is possible to store the one-dose package in the storage unit, and it is possible to simultaneously realize easy extraction of the one-dose package and prevention of falling of the one-does package.

Secondly, it is possible to smoothly extract the one-dose package because of elastic deformation of the support unit, so that it is possible to simplify the structure.

Sixth Example

A storage unit according to a sixth example will be described below with reference to FIG. 10A and FIG. 10B. FIG. 10A is a bottom view of the storage unit according to the sixth example, and FIG. 10B is a vertical cross-sectional view of FIG. 10A.

A storage unit 10 of the sixth example illustrated in FIG. 10A and FIG. 10B is different from the storage unit 10 of the first example illustrated in FIG. 5A and FIG. 5B only in that the storage unit includes a single support unit 19 that is movable using a flab mechanism, instead of the left support unit 12 and the right support unit 13.

The support unit 19 is arranged so as to be opened and closed by swinging around a rotary shaft 19a that is arranged on the end portion of the right bottom wall of the package extraction opening 17, similarly to the second example illustrated in FIG. 6A and FIG. 6B.

The support unit 19 is configured to allow passage of the package 2 when the extracting unit 50 extracts the package 2 from the storage unit 10. In contrast, the support unit 19 is configured to restrict passage of the package 2 and keep storing the plurality of packages 2 in the case portion 11 when the package 2 is not extracted from the storage unit 10.

Specifically, a torsion coil spring with a biasing force in a predetermined range is attached between the rotary shaft 19a of the support unit 19 and the end portion of the right bottom wall. The biasing force is set such that the support unit 19 allows passage of the package 2 when the extracting unit 50 extracts the package 2 from the storage unit 10 and such that the maximum number of packages 2 stored in the case portion 11 and the movable plate 16 are kept stored when the package 2 is not extracted from the storage unit 10.

According to the sixth example, firstly, the extraction portion in the storage unit includes the support unit that supports the one-dose package at a plurality of positions, so that it is possible to store the one-dose package in the storage unit, and it is possible to simultaneously realize easy extraction of the one-dose package and prevention of falling of the one-does package.

Secondly, it is possible to smoothly extract the one-dose package.

Figure 11:
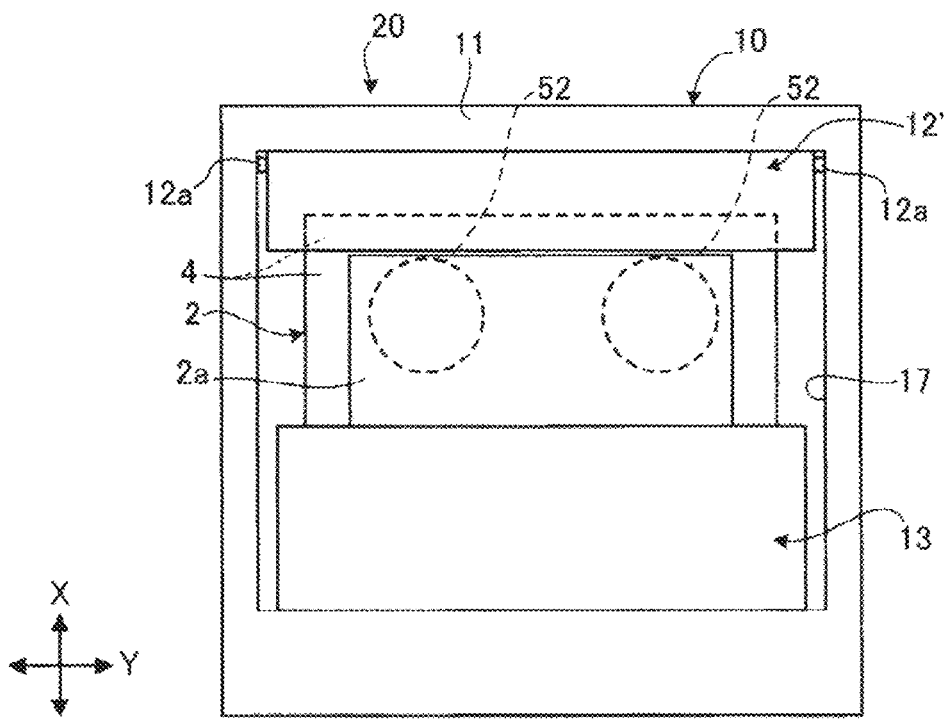
FIG. 11 is a diagram illustrating another example different from the first to the sixth examples, and is a bottom view illustrating attraction pad positions.

In a storage unit 10 according to an example illustrated in FIG. 11, a left support unit 12', which has a flap mechanism and supports the package 2, and the right support unit 13 support the package 2 in the lowermost portion in the storage unit 10 and prevent the package 2 from falling. The left support unit 12' is different from the example illustrated in FIGS. 4A and 4B in that the left support unit 12' does not include a projection, and is the same as the example illustrated in FIGS. 4A and 4B in that two portions on both ends of the left support unit 12' in the Y direction are adopted as the attraction pad positions.

Figure 12A:
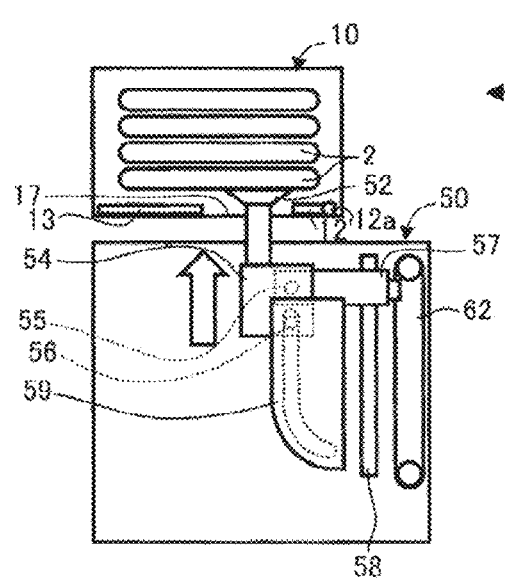
FIG. 12A is a diagram for explaining a defect that occurs when a package is attracted and extracted from a storage unit in the example illustrated in FIG. 11.
Figure 12B:
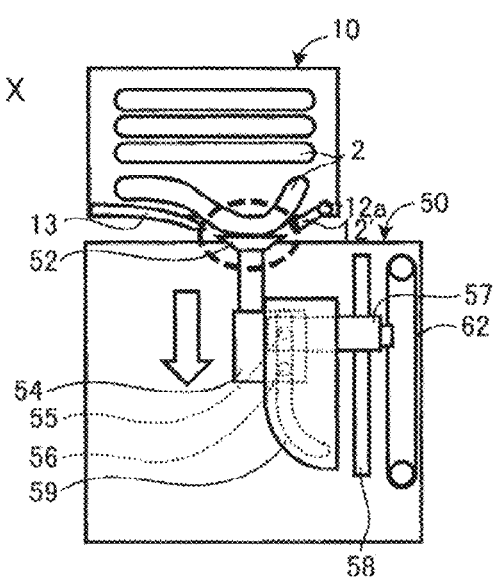
FIG. 12B is a diagram for explaining a defect that occurs when the package is attracted and extracted from the storage unit in the example illustrated in FIG. 11.

As illustrated in FIG. 11, when two portions on both ends of the left support unit 12', which does not have the projection, in the Y direction are adopted as the attraction pad positions, and the package 2 in the storage unit 10 in the lowermost portion is extracted by being attracted by the attraction pads 52, a defect as illustrated in FIG. 12A to FIG. 12B is likely to occur because the package 2 is made with a film material and is easily deformable as described above. Specifically, when the package 2 that is attracted by the attraction pads 52 at the two positions on the near side of the plane of the drawings and on the far side of the plane of the drawings in the Y direction in FIG. 12A and FIG. 12B pushes and rotates the left support unit 12', a leading end portion of the package 2 turns and a gap is generated between the attraction pads 52 and the package (in a portion indicated by a dashed line circle in FIG. 11), so that sucking air may leak, and attraction by the attraction pads 52 may be released.

To cope with this, in the example illustrated in FIG. 11, for example, it may be possible to extract the package from the storage unit 10 by adopting, as a suction pump that generates a suction force on the attraction pads 52, a suction pump that has a strong suction force by which the defect as illustrated in FIG. 12B does not occur. In this case, the attraction pad positions at which the package 2 is attracted are arranged at the two portions on the both ends of the left support unit 12' in the Y direction, and the package 2 on the both ends of the left support unit 12' in the Y direction is attracted by the strong suction force of the suction pump, so that the film of the package 2 is stretched and can resist deformation. With this configuration, it is possible to prevent occurrence of the defect as illustrated in FIG. 12B in which it becomes difficult to extract the packages 2.

Figure 13:
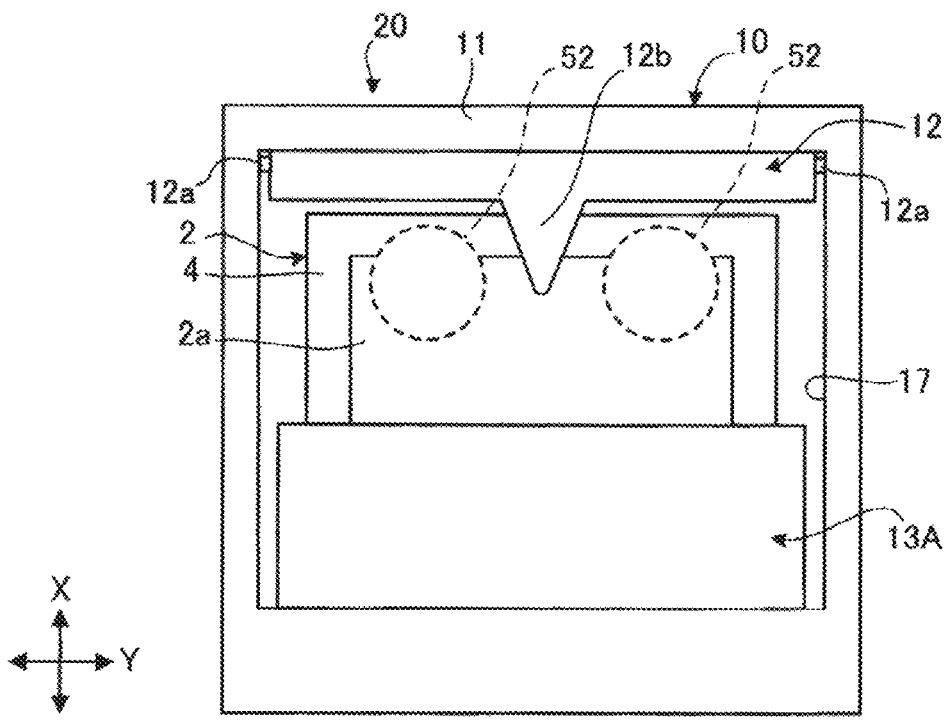
FIG. 13 is a bottom view for explaining another example of a projection of the support unit, which is different from the examples illustrated in FIGS. 4A and 4B, FIG. 11, etc.

Another example of the projection of the support unit will be described below with reference to FIG. 13 and FIG. 14. FIG. 13 is a bottom view for explaining another example of the projection of the support unit, which is different from the example illustrated in FIGS. 4A and 4B, and FIG. 14 is a bottom view for explaining still another example of the projection of the support unit, which is different from the examples illustrated in FIGS. 4A and 4B and FIG. 13.

Figure 14:
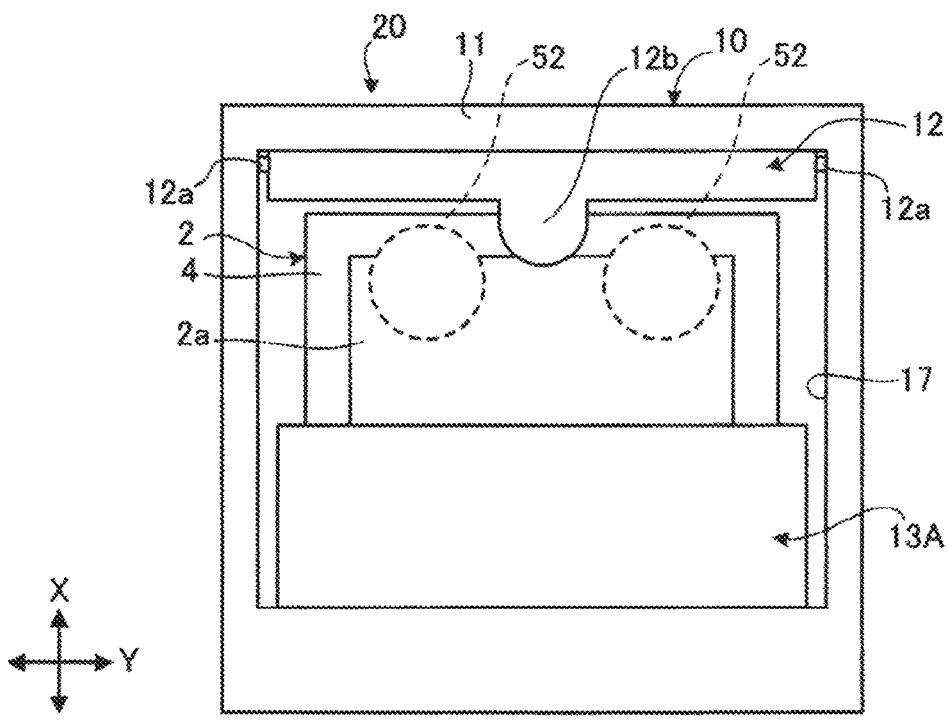
FIG. 14 is a bottom view for explaining still another example of the projection of the support unit, which is different from the examples illustrated in FIGS. 4A and 4B, FIG. 11, etc.

In FIGS. 4A and 4B, the projection 12b of the left support unit 12 has a quadrangular shape, but embodiments are not limited to this example, and may have a triangular shape as illustrated in FIG. 13 or a semicircular shape as illustrated in FIG. 14, in each of which the same effect as described above with reference to FIGS. 4A and 4B can be achieved. In other words, it is sufficient that the projecting shape of the support unit has a certain shape that is partly caught on the one-dose package, in other words, a certain shape that partly overlaps with the one-dose package.

Meanwhile, it is of course possible to adopt the examples of the projection of the support unit as described above to the first to the forth examples illustrated in FIG. 5A to FIG. 8B.

Figure 15:
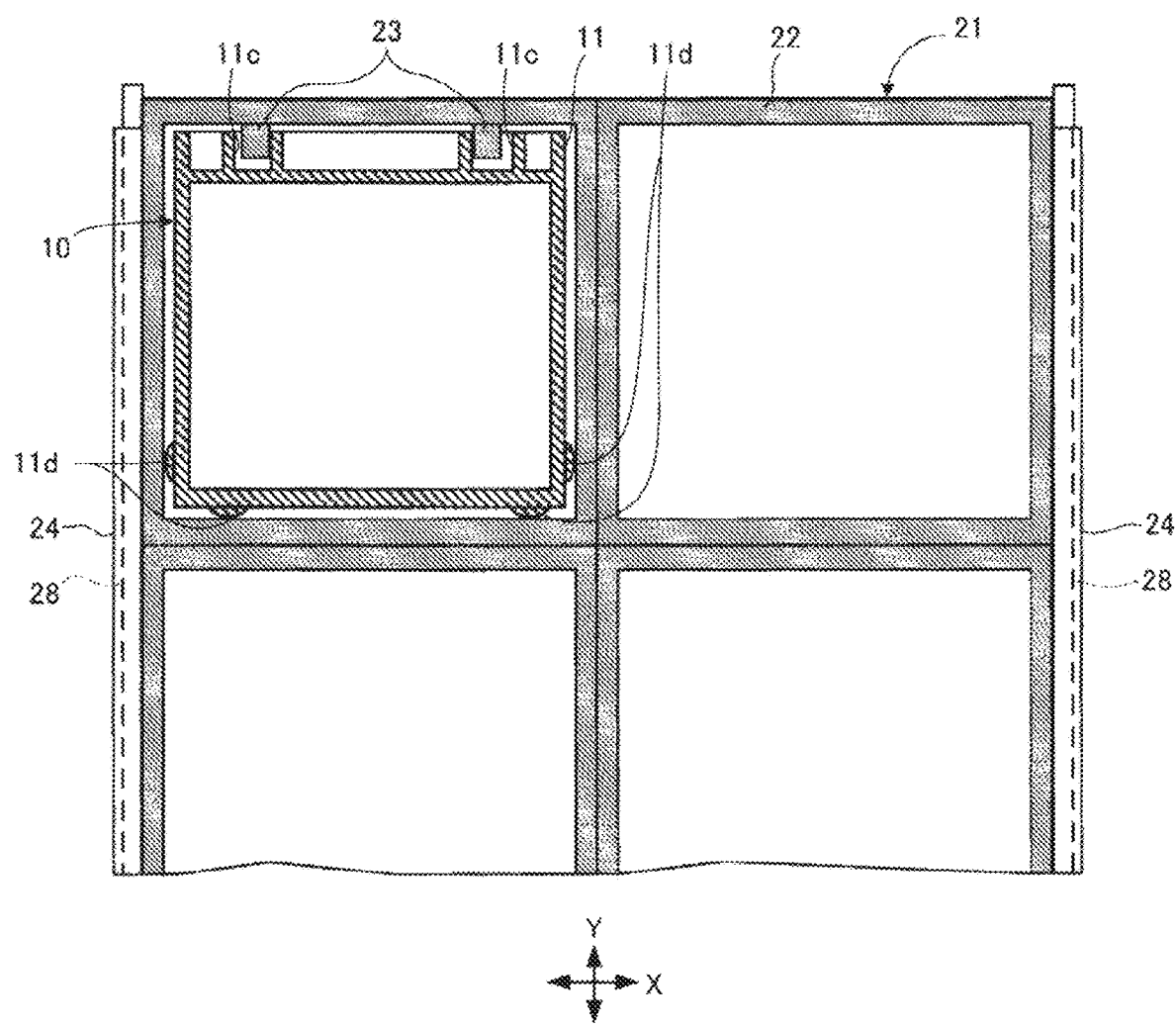
FIG. 15 is a planar cross-sectional view of a main part including an attachment/detachment mechanism that is for the storage unit and that is arranged in a drawn unit.

An attachment/detachment mechanism, which is for the storage unit and which is arranged in the drawn unit, and operation will be described below with reference to FIG. 15 and FIG. 16. FIG. 15 is a planar cross-sectional view of a main part including an attachment/detachment mechanism that is for the storage unit and that is arranged in the drawn unit.

As illustrated in FIG. 15, the drawn unit 21 is configured such that the plurality of storage units 10 are detachably attached thereto. The storage units 10 that are configured in a detachably attachable manner are general referred to as "cartridges". A slide rail 24 is arranged on each of right and left external wall surfaces of a case portion 22 of the drawn unit 21, and each of the slide rails 24 is able to slide with a main body rail 28 that is arranged on the main-body frame 199 (see FIG. 1A). With this configuration, the drawn unit 21 can be detached and attached by being drawn from the main-body frame 199 (see FIG. 1A) via engagement between the slide rails 24 and the main body rails 28.

Furthermore, as illustrated in FIG. 15, the storage unit 10 is attached and detached to and from the drawn units 21 via engagement and disengagement of a pair of projections 23, which are formed on an inner wall surface of the case portion 22 of the drawn unit 21 so as to protrude inward, and a pair of recesses 11c, which are formed on an outer wall of the case portion 11 of the storage unit 10, and via engagement and disengagement of four semispherical protrusions 11d, which are formed on the inner wall surface of the case portion 22, and the outer wall of the case portion 11. With the attachment/detachment mechanism of the drawn unit 21 as described above, it is possible to more easily perform attachment/detachment operation on the plurality of storage units 10 with good operability.

In the example as described above, attachment and detachment are realized via fitting and engagement of a recess and a projection, but embodiments are not limited to this example, and it is possible to achieve the same effect as described above by adopting a configuration in which an elastic material is arranged in a gap between the inner wall surface of the case portion 22 and the outer wall surface of the case portion 11, a configuration using a magnetic force, or a snap-fit structure.

Figure 16:
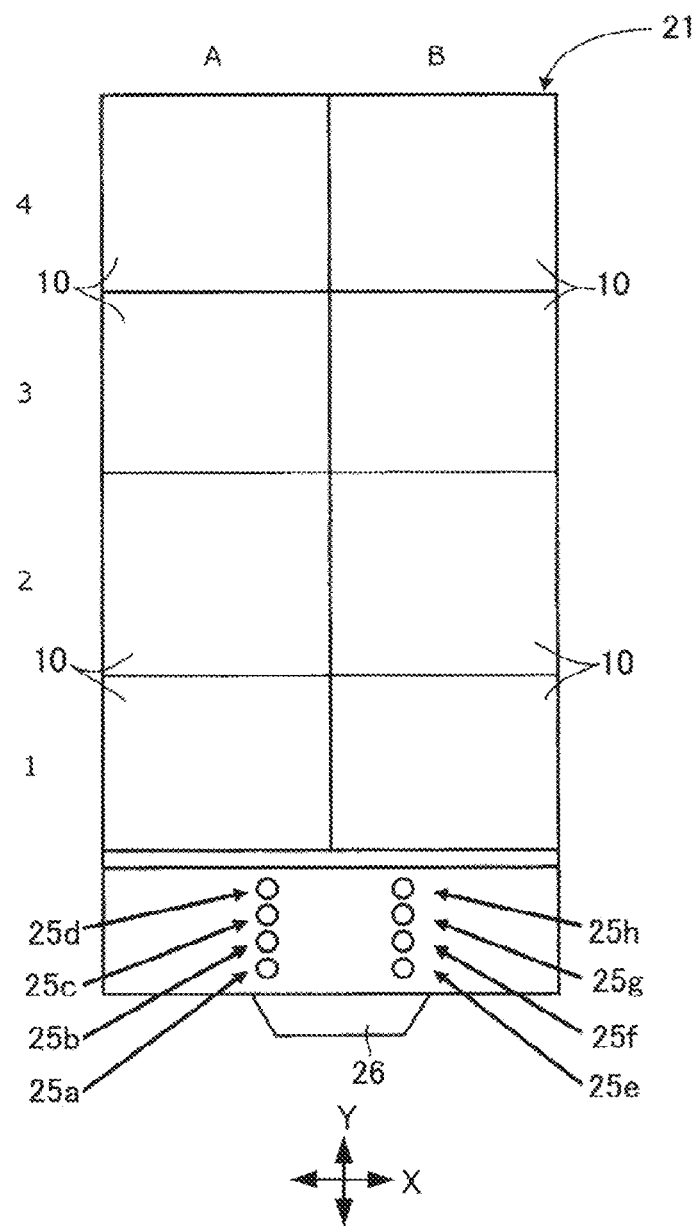
FIG. 16 is a plan view for explaining a configuration that is arranged is the drawn unit to identify the storage unit.

As an example is illustrated in FIG. 16, the drawn unit 21 includes, in the vicinity of a handle 26 to be held by hand at the time of attachment/detachment operation, guide display units, such as light emitting diodes (LEDs) 25a to 25h, for clarifying setting positions of the plurality of storage units 10. With this configuration, it is possible to recognize, at a glance, a position at which the target storage unit 10 is present in the drawn unit 21. In this figure, the LED 25a is used for detecting presence or absence of the storage unit 10 that is attached and detached with respect to A1 (indicating a portion or a section that is uniquely determined by a column and a row) in the drawn unit 21. Similarly, the LED 25b is used for detecting presence or absence of the storage unit 10 that is attached and detached with respect to a portion A2 in the drawn unit 21, the LED 25c is for a portion A3 in the drawn unit 21, the LED 25d is for a portion A4 in the drawn unit 21, the LED 25e is for a portion B1 in the drawn unit 21, the LED 25f is for a portion B2 in the drawn unit 21, the LED 25g is for a portion B3 in the drawn unit 21, and the LED 25h is for a portion B4 in the drawn unit 21.

Meanwhile, with use of the guide display units, such as the LEDs 25a to 25h, staff or the like as an operator who attaches or detaches the storage unit 10 may make a mistake, so that it may be possible to adopt a method of electronically identifying presence or absence of the storage unit 1—by a sensor, a switch, or the like, for example.

Furthermore, it is preferable to provide a number, a barcode, a QR (registered trademark) code, a non-contact IC tag, or the in the storage unit so as to be able to identify each of the storage units, and store information on association among a person, a medicine, and the storage unit in a system. Moreover, after setting, in the apparatus main body, the drawn unit in which the storage units are attached, each of the storage units is identified by the apparatus main body. With this configuration, the apparatus is able to pick up a target package without a mistake.

A configuration and operation of the extracting unit will be described below with reference to FIG. 17A, FIG. 17B, and FIGS. 18A to 18F. FIG. 17A is a front view illustrating the configuration of the extracting unit, FIG. 17B is a plan view of FIG. 17A, and FIGS. 18A to 18F are front views illustrating processes of operation of the extracting unit.

As illustrated in FIG. 17A and FIG. 17B, the extracting unit 50 includes an attracting unit 51 that extracts the package 2 from the storage unit 10 and holds the package 2. The attracting unit 51 includes an air suction pump 48 (illustrated only in a block diagram of FIG. 21 to be described later), and attracts the package 2 by being negatively pressurized by the suction pump 48.

The suction pump 48 may be arranged on the extracting unit 50, or may be arranged on a different portion in the apparatus. If the suction pump is arranged inside the apparatus, the suction pump is connected via a connection member, such as an air tube.

The attracting unit 51 further includes the attraction pads 52 that communicate with the suction pump and attract the package 2, and attracting ducts 53 that are connected to the attraction pads 52. The attraction pad 52 functions as an attracting means or an attracting member that attracts and extracts the package 2 in the storage unit 10.

Upper ends as one ends of the attraction pads 52 in FIG. 17A are arranged so as to attract the package 2 as described above. Lower ends as the other ends of the attraction pads 52 in FIG. 17A are fixedly mounted on upper ends as one ends of the attracting ducts 53 in FIG. 17A. Lower ends as the other ends of the attracting ducts 53 in FIG. 17A are fixedly mounted on a rotary base member 54. The attraction pads 52 and the attracting ducts 53 are arranged as pairs in the Y direction.

The extracting unit 50 further includes a posture changing means that changes a posture of the package 2 extracted from the storage unit 10 to an approximately vertical state. The posture changing means in the extracting unit 50 includes, as main structural members, the rotary base member 54 that is connected to a fixing member 57 via a rotary shaft 55, guide members 59 in which guide gutters 59a having specific shapes are formed, a guide shaft 56 that is always fitted in the guide gutters 59a of the guide members 59 and guides the rotary base member 54, and an attracting unit vertical moving unit.

The rotary base member 54 is connected to the fixing member 57 via the rotary shaft 55. The rotary base member 54 may be arranged so as to be rotatable (in other words, swingable) in a predetermined angular range around the rotary shaft 55 that is fixed to the rotary base member 54, or may be arranged so as to be swingable around the rotary shaft 55 that is fixed to the fixing member 57. In other words, in FIGS. 17A and 17B, a distance between a center of the rotary shaft 55 and a center of guide rods 58 in the X direction is always maintained constant when the fixing member 57 moves in the up-down direction Z along the guide rods 58.

The attracting unit vertical moving unit includes the guide rods 58 that guide the fixing member 57 in the Z direction and that are arranged as a pair in the Y direction, an endless belt 62 that is wound around a drive pulley 60 and a driven pulley 61, and an attracting unit vertical movement motor 63 that is connected to the drive pulley 60 via a drive transmission member, such as a gear or a belt. The attracting unit vertical movement motor 63 serves as a driving means or a drive source of the attracting unit vertical moving unit.

The fixing member 57 is connected and fixed to the belt 62 by a belt holding unit 62a that is fixed to a right end portion of the fixing member 57.

The guide rods 58 are arranged so as to be elongated along the Z direction and as a pair in the Y direction, and the lower end portions of the guide rods are fixed on a bottom frame 50b of an extraction frame 50a that is arranged on the extracting unit 50.

Guided holes 57a to be inserted in the guide rods 58 are formed on a right end portion of the fixing member 57.

Each of the drive pulley 60 and the driven pulley 61 includes a pulley shaft (not illustrated) that is rotatably supported on an immobile member on the extraction frame 50a. The attracting unit vertical movement motor 63 is fixed to an immobile member on the extraction frame 50a of the extracting unit 50. The attracting unit vertical movement motor 63 serves as a control target driving member of the attracting unit vertical moving unit (see FIG. 21 to be described later).

When the fixing member 57 moves up and down with operation of the attracting unit vertical movement motor 63, the fixing member 57 moves in the Z direction along each of the guide rods 58, so that it is possible to maintain the posture of the fixing member 57 on the KY plane in an approximately horizontal state.

Meanwhile, the attracting unit vertical moving unit is not limited to an up-down reciprocating movement mechanism using belt driving as described above, but may be a reciprocating straight movement mechanism using a rack and pinion or the like.

The guide members 59 are arranged as a pair on both ends of the attracting unit 51 in the Y direction across the rotary base, member 54, and lower end portions of the guide members 59 are fixed to the bottom frame 50b.

The guide shaft 56 is arranged so as to protrude on both end portions of the rotary base member 54 in the Y direction, is always fitted in the guide gutters 59a of the guide members 59, and guide the rotary base member 54. As illustrated in FIG. 17A, the guide shaft 56 is arranged below the rotary shaft 55 of the rotary base member 54 in the Z direction, at a constant distance from the rotary shaft 55.

When the fixing member 57 moves in the Z direction with operation of the attracting unit vertical movement motor 63, the posture of the fixing member 57 on the XY plane is maintained in the approximately horizontal state and the guide shaft 56 of the rotary base member 54 moves in the Z direction along the guide gutters 59a having the specific shapes, so that it is possible to rotate the posture of the attraction pad 52 by about 90 degrees (a state in which the attracting unit 51 is rotated by about 90 degrees is indicated by a bold dashed line in FIG. 17A).

Here, the approximately horizontal state includes a horizontal state and a state within a range of a predetermined angular tolerance with respect to the horizontal state, where the angular tolerance is an acceptable tolerance to achieve the effects of the present invention.

Each of the guide gutters 59a having the specific shapes includes a first guide gutter portion that is extended in the Z direction, that has a relatively long length, and that maintains the postures of the attraction pads 52 as indicated by a solid line in FIG. 17A via the rotary base member 54 in the approximately horizontal state with the guide of the guide shaft 56, and a second guide gutter portion that is communicably connected to the first guide gutter portion, that is formed so as to gradually form a moderate circular arc in a right downward direction, and that rotates the postures of the rotary base member 54 and the attraction pads 52 by about 90 degrees.

Operation of the extracting unit 50 will be described below with reference to FIGS. 18A to 18F. Meanwhile, for the sake of simplification of explanation and easy understanding, in this example, it is assumed that, by the operation of the transfer unit 90 illustrated in FIG. 1A, the extracting unit 50 is located between the storage units 10 on the drawn unit 21 that is arranged in the uppermost portion of the main-body frame 199 in FIG. 1A and the medicine distribution tray 30 that is arranged just below the drawn unit 21. Furthermore, it is assumed that the storage unit 10 as illustrated in FIGS. 4A and 4B is used.

Figure 18A:
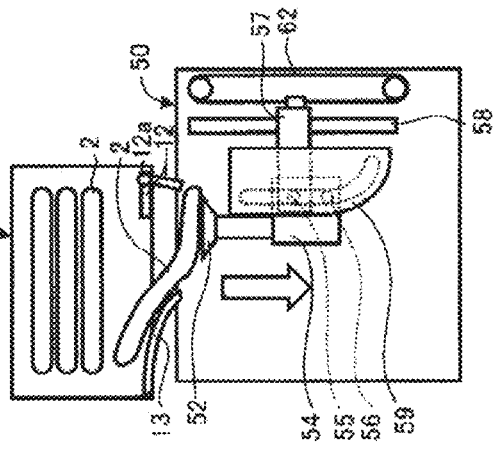
FIG. 18A is a front view illustrating a process of operation of the extracting unit.
Figure 18B:
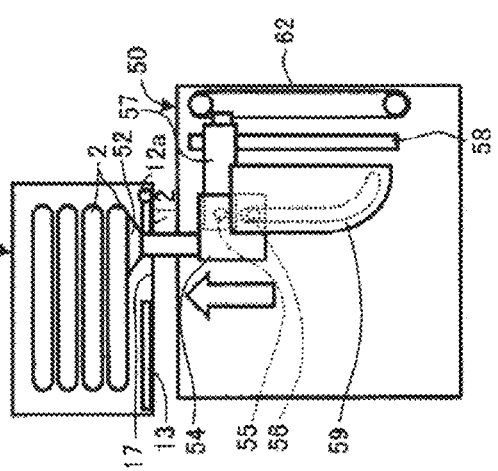
FIG. 18B is a front view illustrating the process of operation of the extracting unit.

As illustrated in FIG. 18A, by the operation of the transfer unit 90 illustrated in FIG. 1A, the extracting unit 50 moves under the storage unit 10 and enters a movement stopped state. In this case, the attracting unit vertical movement motor 63 of the attracting unit vertical moving unit is stopped, and the attraction pads 52 are located below an extracting unit top surface position (indicating a top surface position of the extraction frame 50a of the extracting unit 50 having a casing shape). Thereafter, as illustrated in FIG. 18B, with the operation of the attracting unit vertical movement motor 63, the attraction pads 52 move in an upward direction, are inserted through the package extraction opening 17 between the left support unit 12 having the flap mechanism and the right support unit 13 as the elastic member, come into contact with the package 2 located in the lowermost portion of the storage unit 10, and simultaneously attract the package 2. At this time, the suction pump is driven in advance and attraction operation is enabled.

Figure 18C:
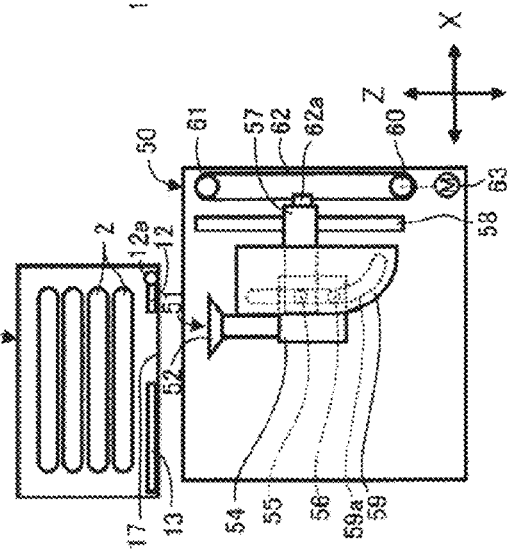
FIG. 18C is a front view illustrating the process of operation of the extracting unit.

Subsequently, as illustrated in FIG. 18C, with reverse operation of the attracting unit vertical movement motor 63, the attraction pads 52 move in a downward direction while attracting the package 2, and a leading end side (indicating a side that is attracted by the attraction pads 52; the same applies in the descriptions below) as one end side of the package 2 is extracted from the storage unit 10. Meanwhile, the left support unit 12 on the right side of the package extraction opening 17 in the storage unit 10 in the drawing is in a flapped state due to the biasing force of the torsion coil spring (not illustrated) in the predetermined range as described above, and therefore is opened and closed by drawing operation of the attraction pads 52. Furthermore, the right support unit 13 is made with an elastic member with an appropriate elastic force in the predetermined range, so that a trailing end side as the other end side of the package 2 (indicating a side that is not attracted by the attraction pads 52; the same applies in the descriptions below) is opened and closed while being elastically deformed by the drawing operation of the attraction pads 52.

Figure 18D:
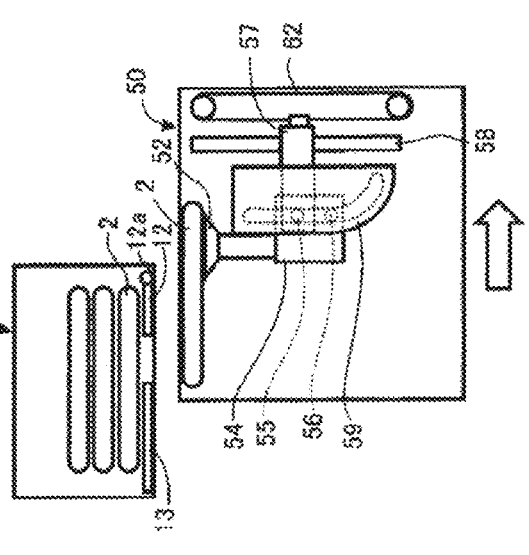
FIG. 18D is a front view illustrating the process of operation of the extracting unit.
Figure 18E:
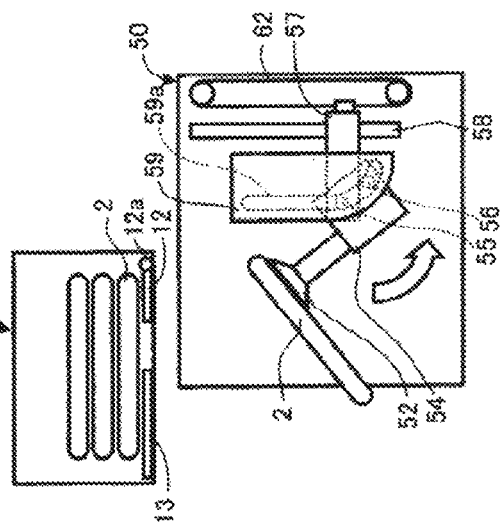
FIG. 18E is a front view illustrating the process of operation of the extracting unit.
Figure 18F:
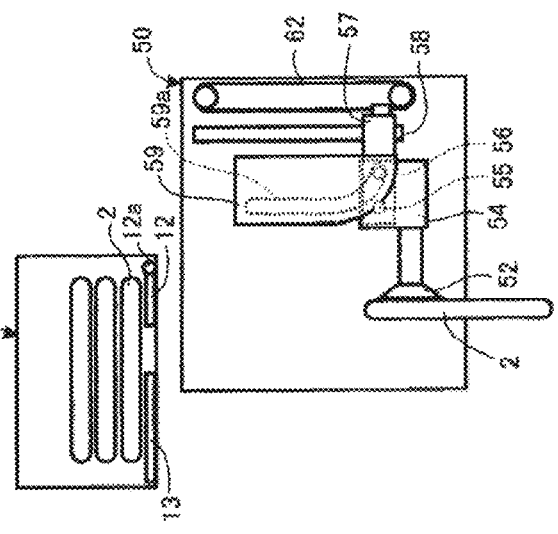
FIG. 18F is a front view illustrating the process of operation of the extracting unit.

Subsequently, as illustrated in FIG. 18D, with the operation of the transfer unit 90 (see FIG. 1A), the extracting unit 50 is moved in the X direction that is the lateral direction, and the trailing end side of the package 2 is drawn or extracted from the storage unit 10. Immediately after the operation as described above, as illustrated in FIG. 18E and FIG. 18F, the posture of the package 2 that is attracted and held by the attraction pads 52 is rotated by approximately 90 degrees from the approximately horizontal state to an approximately perpendicular state (hereinafter, also referred to as an approximately vertical state) with respect to the approximately horizontal state, along with the operation of the attracting unit vertical movement motor 63. The rotation operation at this time is realised by allowing the rotary shaft 55 arranged in the rotary base member 54 to move along the guide gutters 59a of the guide members 59, so that it is possible to change the posture of the package 2 from the approximately horizontal state to the approximately vertical state. As a drive source at this time, a series of operation performed by the single attracting unit vertical movement motor 63 is applicable.

Here, the approximately vertical state or perpendicular state includes a vertical state or a perpendicular state and includes a state within a range of a predetermined angular tolerance with respect to the vertical state or the perpendicular state, where the angular tolerance is an acceptable tolerance to achieve the effects of the present invention.

As described above, in the process of extracting the package 2 from the storage unit 10, the extracting unit 50 extracts the leading end side as one end side of the package downward from the storage unit 10, and the transfer unit 90 moves the extracting unit 50 such that the trailing end side as the other end side of the package 2 is extracted from the storage unit 10 while the leading end side of the package 2 is extracted downward from the storage unit 10.

Then, the moving direction of the extracting unit 50 moved by the transfer unit 90 is set to the X direction that is the lateral direction in which a supported state of the trailing end side of the package 2 by the right support unit 13 is released and the trailing end side is extracted from the package extraction opening 17.

As illustrated in FIG. 18C, the left support unit 12 and the right support unit 13 are opened and closed by the drawing operation of the attraction pads 52, so that it is not necessary to separately provide a drive source for opening and closing operation, and it is possible to reliably extract the package 2 from the storage unit 10, simplify the apparatus, and save power.

As described above, in the first embodiment, when the package 2 is extracted from the storage unit 10, the extracting unit 50 is located or arranged under of the storage unit 10, and the package 2 is extracted in the downward direction of the storage unit 10. In this manner, by extracting the package 2 from the lower side oar the storage unit 10, the next package 2 automatically moves in a downward direction (direction toward the package extraction opening 17) by weights of the package 2 remaining in the storage unit 10 and the movable plate 16, so that it is possible to allow the extracting unit 50 to perform the same operation with a simple structure independent of an amount of the packages 2 remaining in the storage unit 10.

Figure 19A:
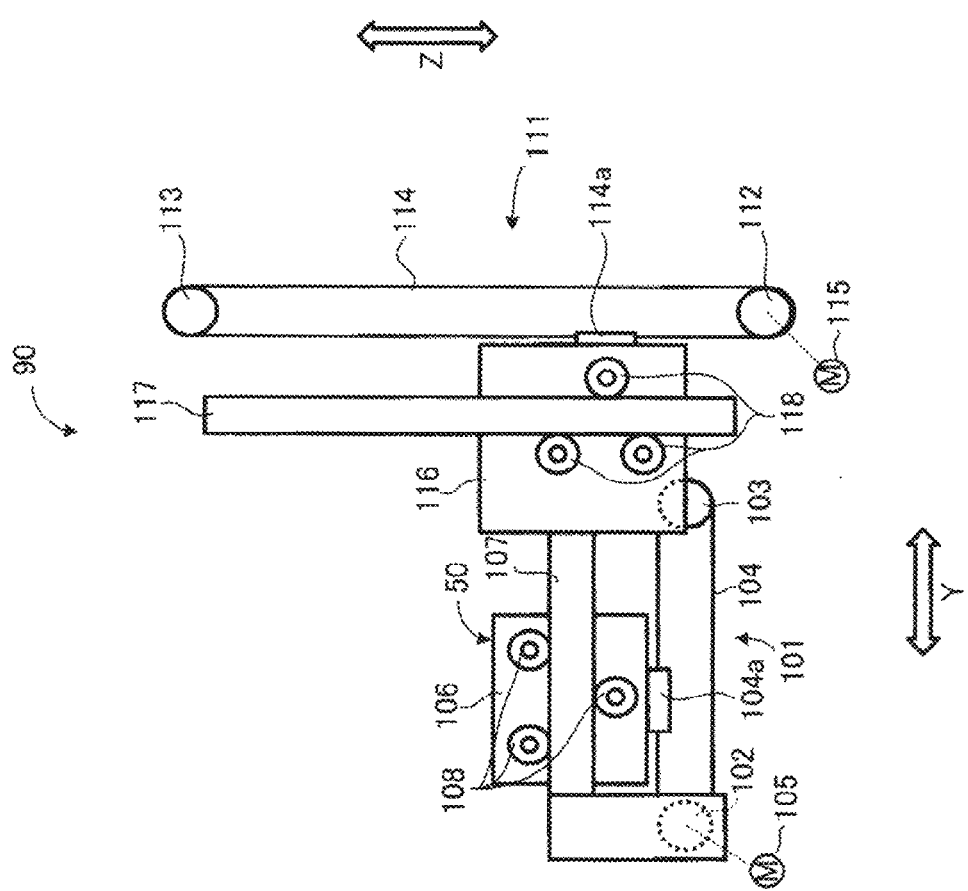
FIG. 19A is a front view illustrating a main configuration of a transfer unit.
Figure 19B:
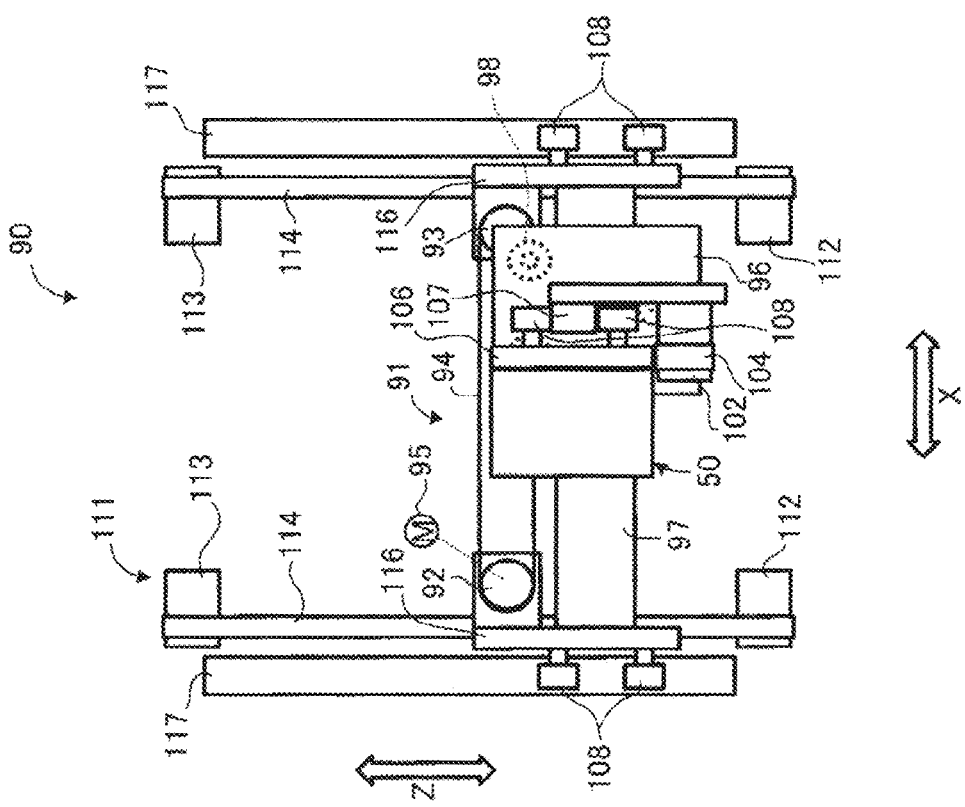
FIG. 19B is a side view of FIG. 19A.

A configuration and operation of the transfer unit 90 will be described below with reference to FIGS. 19A and 19B. FIG. 19A is a front view illustrating a main configuration of the transfer unit, and FIG. 19B is a side view of FIG. 19A.

As in the configuration of the medication support apparatus 200 in FIG. 1A, the storage units 10 are arranged on planes in the upper portion and the lower portion in the Z direction across the medicine distribution trays 30, and the medicine distribution trays 30 are arranged above the storage units 10 located in the lowermost portion; therefore, the extracting unit 50 is configured to move in the three directions, i.e., the X direction, the Y direction, and the Z direction. In this manner, the transfer unit 90 is configured to move the extracting unit 50 in the X direction, the Y direction, and the Z direction in order to deliver the packages that are extracted by the extracting unit 50 from the storage units 10 to the medicine distribution trays 30.

An X-direction transfer unit 91 moves the extracting unit 50 in the X direction, a Y-direction transfer unit 101 moves the extracting unit 50 in the Y direction, and a Z-direction transfer unit 111 moves the extracting unit 50 in the Z direction, all of which have similar configurations.

The X-direction transfer unit 91 includes an X adapter 96 that is mounted on the extracting unit 50, an X guide member 97 that guides the extracting unit 50 in the X direction via the X adapter 96, an endless belt 94 that is wound around a drive pulley 92 and a driven pulley 93, and an X-direction transfer motor 95 that is connected to the drive pulley 92 via a driving force transmission member, such as a gear or a belt.

Three rollers 98 (two of the three are located behind the extracting unit 50 and not illustrated) are mounted on the X adapter 96 such that the rollers can roll in a state of sandwiching the X guide member 97. Furthermore, the X adapter 96 is connected and fixed to the endless belt 94 via a belt holding unit (not illustrated).

With the configuration of the X-direction transfer unit 91 as described above, when the X-direction transfer motor 95 is driven, a driving force is transmitted to the endless belt 94 via the driving force transmission member and the drive pulley 92, so that the endless belt 94 moves in a rotating manner and the extracting unit 50 moves in the X direction together with the X adapter 96 along the X guide member 97.

The Y-direction transfer unit 101 includes a Y adapter 106 that is mounted on the extracting unit 50, a Y guide member 107 that guides the extracting unit 50 in the Y direction via the Y adapter 106, an endless belt 104 that is wound around a drive pulley 102 and a driven pulley 103, and a Y-direction transfer motor 105 that is connected to the drive pulley 102 via a driving force transmission member, such as a gear or a belt.

Three rollers 108 are mounted on the Y adapter 106 such that the rollers can roll in a state of sandwiching the Y guide member 107. Furthermore, the adapter 106 is connected and fixed to the endless belt 104 via a belt holding unit 104a.

With the configuration of the Y-direction transfer unit 101 as described above, when the Y-direction transfer motor 105 is driven, a driving force is transmitted to the endless belt 104 via the driving force transmission member and the drive pulley 102, so that the endless belt 104 moves in a rotating manner and the extracting unit 50 moves in the Y direction together with the Y adapter 106 along the Y guide member 107.

The Z-direction transfer unit 111 includes a pair of Z adapters 116 that are arranged on both end portions of the X guide member 97 in the X direction, a pair of Z guide members 117 that guide the extracting unit 50 in the Z direction via the X guide member 97 and the pair of Z adapters 116, endless belts 114 that are extended around drive pulleys 112 and driven pulleys 113, and a Z-direction transfer motor 115 that is connected to the drive pulleys 112 via a driving force transmission member, such as a gear or a belt.

In the Z-direction transfer unit 111, the drive pulleys 112, the driven pulleys 113, and the endless belts 114 are arranged on the both sides in the X direction, but the Z-direction transfer motor 115 is arranged on only one of the drive pulleys 112.

Three rollers 118 are mounted on each of the Z adapters 116 such that the rollers can roll in a state of sandwiching the Z guide member 117. Furthermore, each of the Z adapters 116 is connected and fixed to each of the endless belts 114 via each of belt holding units 114a.

With the configuration of the Z-direction transfer unit 111 as described above, when the Z-direction transfer motor 115 is driven, a driving force is transmitted to the endless belts 114 via the driving force transmission member and the drive pulleys 112, so that the endless belts 114 move in a rotating manner and the extracting unit 50 moves in the Z direction together with the X guide member 97 and the Z adapters 116 along the Z guide member 117.

In FIGS. 19A and 19B, the extracting unit 50 is configured to move in direction of three axes, i.e., the X-axis, the Y-axis, and the Z-axis; however, for example, in a configuration in which the storage units 10 are arranged on over and the medicine distribution trays 30 are arranged under the extracting unit 50 sandwiched therebetween, it is satisfactory for the extracting unit 50 to move only in the X direction and the Y direction, so that it is possible to reduce one moving shaft.

Figure 20:
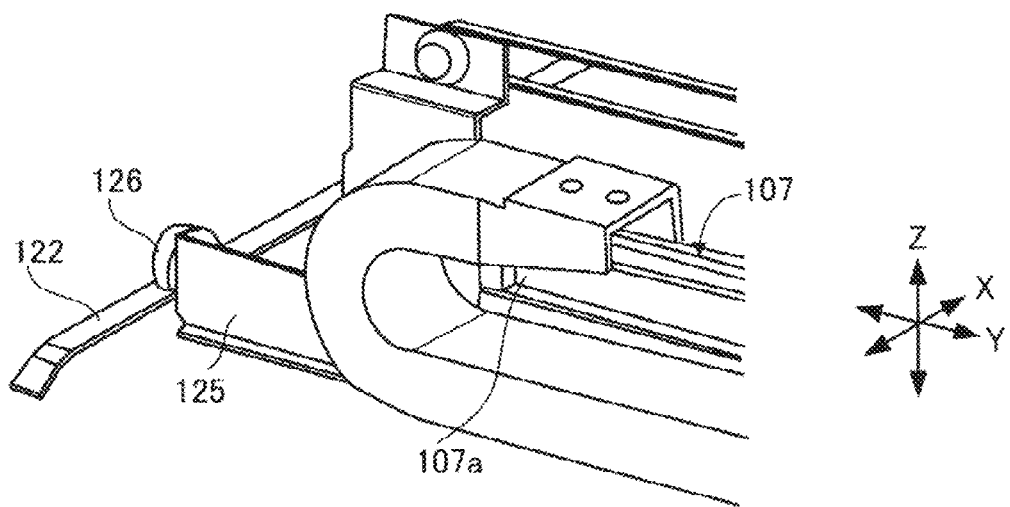
FIG. 20 is a perspective view of a main part illustrating a configuration example for holding an end of a Y guide unit in the transfer unit.

In the configuration of the transfer unit 90 illustrated in FIGS. 19A and 19B, a leading end of the Y guide member 107 in the Y direction is not held. Therefore, as illustrated in FIG. 20, to hold a leading end portion 107a of the Y guide member 107, it may be possible to arrange a roller 126 in a leading end portion of a bracket member 125 on which the leading end portion 107a of the Y guide member 107 is mounted and supported, and arrange the roller 126 such that the roller 126 can roll on a receiving portion 122 that is arranged on the main-body frame 199 side.

With this configuration, it is possible to prevent the leading end portion 107a side of the Y guide member 107 from bending by own weight. Accordingly, it is possible to reduce variation in arrangement distances between the extracting unit 50 and the storage units 10 or the medicine distribution trays 30, so that it is possible to stably extract the packages 2 and insert or put the packages 2 in the medicine distribution trays 30.

Figure 21:
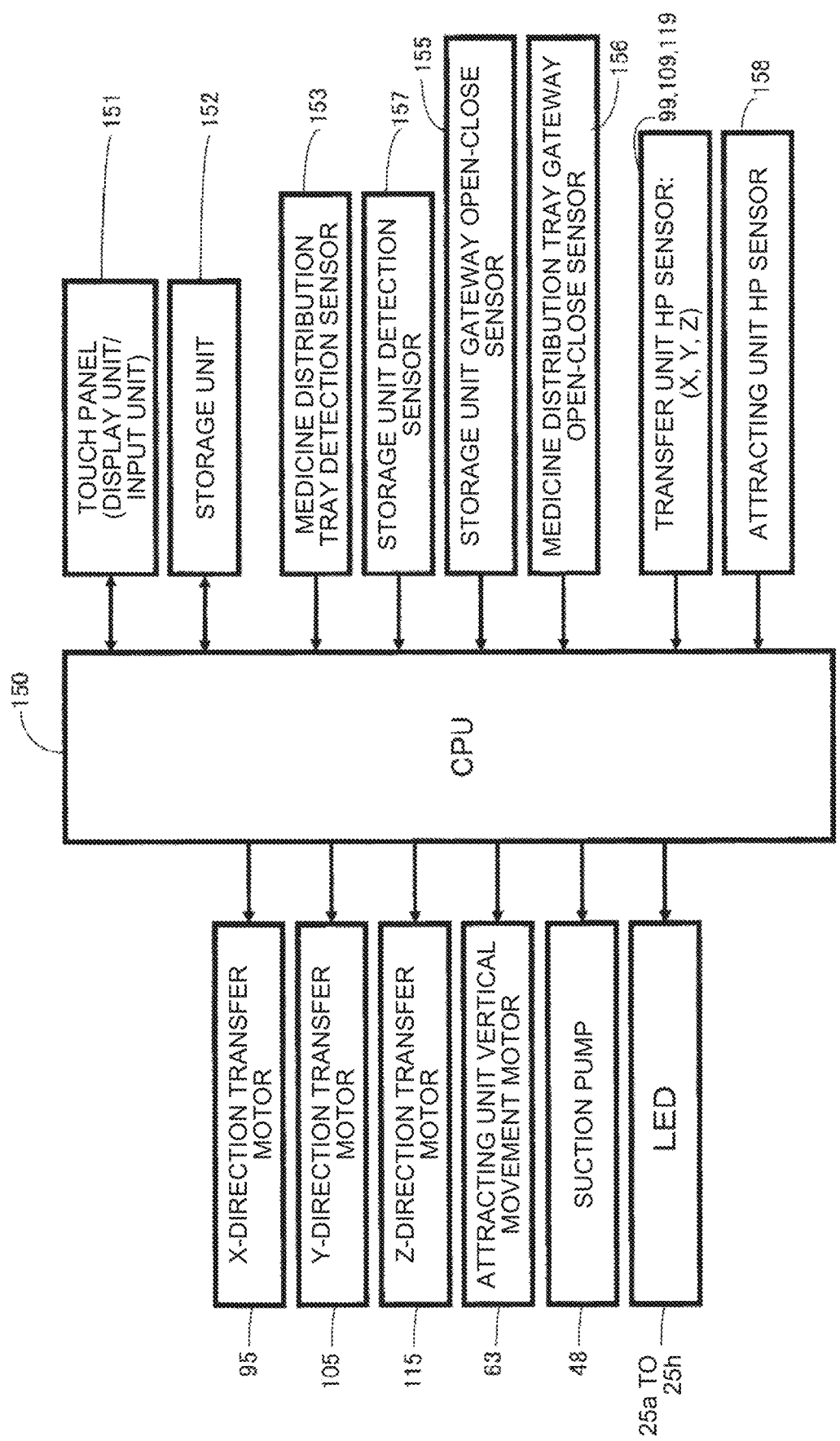
FIG. 21 is a control block diagram illustrating a main control configuration of the medication support apparatus according to the first embodiment.

A control configuration of the medication support apparatus 200 according to the present invention will be described below with reference to FIG. 21. FIG. 21 is a control block diagram illustrating a main control configuration of the medication support apparatus according to the first embodiment.

As illustrated in FIG. 21, the medication support apparatus 200 includes a central processing unit (CPU) that functions as a control unit 150 serving as a control means for controlling operation of each of the units of the medication support apparatus 200. The CPU includes a built-in storage unit, a built-in timer unit, and the like. The CPU gives a notification to staff or the like and an instruction on operation of the apparatus at a timing synchronized with a program in accordance with various kinds of input from a sensor and the like (to be described later).

The CPU may include a timer (time measurement) function, in addition to an arithmetic function and a control function. A storage unit 152 includes a read only memory (ROM), a random access memory (RAM), an external memory, and the like. The ROM stores therein, in advance, a program (for example, a program, such as a control flowchart, to be described later) that can be read by the CPU as described above, various kinds of data, and the like. Examples of the data include relationship data between the sections 33, which are are included in the medicine distribution tray 30 and which are assigned to each of medicated persons, and the packages 2, relationship data between the sections 33, which are included in the medicine distribution tray 30 and which are assigned to each of the medication times, and the packages 2, and relationship data between the sections 33, which are included in the medicine distribution tray 30 and which are assigned in sequential order of medication, and the packages 2.

A touch panel 151 as a user interface is electrically connected to an input-output port of the CPU. The touch panel 151 is not specifically limited, and may be configured by a combination of an input unit and a display unit, such as a keyboard and an LED display unit, as separate bodies.

A medicine distribution tray detection sensor 153 that detects types of the medicine distribution trays 30 and presence or absence of the medicine distribution trays 30 and a storage unit detection sensor 157 that detects presence or absence of the storage units 10 are electrically connected to the input-output port of the CPU.

Furthermore, a transfer unit home position (hereinafter, abbreviated as "HP") sensor 99 that detects an HP of the X-direction transfer unit 91 in the extracting unit 50, a transfer unit HP sensor 109 that detects an HP of the Y-direction transfer unit 101 in the extracting unit 50, and a transfer unit HP sensor 119 that detects an HP of the Z-direction transfer unit 111 in the extracting unit 50 are electrically connected to the input-output port of the CPU.

Moreover, an attracting unit HP sensor 158 that detects an HP of the attracting unit 51 (in particular, the attraction pads 52) in the extracting unit 50 is electrically connected to the input-output unit of the CPU.

The LEDs 25a to 25h of the drawn unit 21, the suction pump 48, the attracting unit vertical movement motor 63, the X-direction transfer motor 95 of the X-direction transfer unit 91, the Y-direction transfer motor 105 of the Y-direction transfer unit 101, and the Z-direction transfer motor 115 of the Z-direction transfer unit 111 are electrically connected to an output port of the CPU.

A notification unit may be electrically connected to the output port of the CPU. The notification unit gives a notice of a state of the apparatus and each of the units as described above by light of an LED or the like, sound including voice, or vibration. A speaker, a light, or the like is provided to give a notice of medication timings even when staff or the like is away from the apparatus.

If input information from the touch panel 151 and various signals from various sensors are input to the CPU, the CPU outputs a command signal as described below. Specifically, the CPU outputs a command signal that is an instruction for controlling an audio device or an optical device of a display device (including the notification unit as described above) of the touch panel 151, the LEDs 25a to 25h, the suction pump 48, the attracting unit vertical movement motor 63, the X-direction transfer motor 95, the Y-direction transfer motor 105, and the Z-direction transfer motor 115.

The CPU has a function to execute control operation explained and illustrated in a control flowchart as will be described below.

A flow of entire main operation of the medication support apparatus will be described below with reference to FIG. 22A to FIG. 22H. The operation is executed in accordance with a control command of the CPU of the control unit 150.

As illustrated in FIG. 22A to FIG. 22F, the specific operation as described above with reference to FIG. 18A to FIG. 18F is performed. An operation state illustrated FIG. 22F indicates a state in which the postures of the attraction pads 52 that are attracting and holding the package 2 extracted from the storage unit 10 are rotated by about 90 degrees. As illustrated in FIG. 22G, the extracted package 2 is held by the attraction pads 52 of the extracting unit 50 in the same posture as in FIG. 22F.

Furthermore, as illustrated in FIG. 22G, the extracting unit 50 including the attraction pads 52 that are holding the package 2 is transferred by the transfer unit 90 on a route indicated by a dashed line to the medicine distribution portion 29 in which the medicine distribution tray 30 is set. When the extracting unit 50 is transferred to approximately above the medicine distribution tray 30 in the medicine distribution portion 29, drive of the suction pump 48 is stopped. Accordingly, the attraction and holding of the package 2 by the attraction pads 52 are released, and the package 2 is inserted in the predetermined section 33 at a predetermined position in the medicine distribution tray 30.

The operation as described above is repeated a plurality of number of times to insert the necessary packages 2 to the predetermined sections 33 in the medicine distribution tray 30, and thereafter, as illustrated in FIG. 22H, the medicine distribution tray 30 is extracted from, for example, the second gateway portion 42 to the outside of the apparatus and received by a medication assistant, such as staff in a nursing home or the like.

The flow of operation of the extracting unit in the entire main operation illustrated in FIG. 22A to FIG. 22H will be further described below with reference to FIG. 23.

Figure 23:
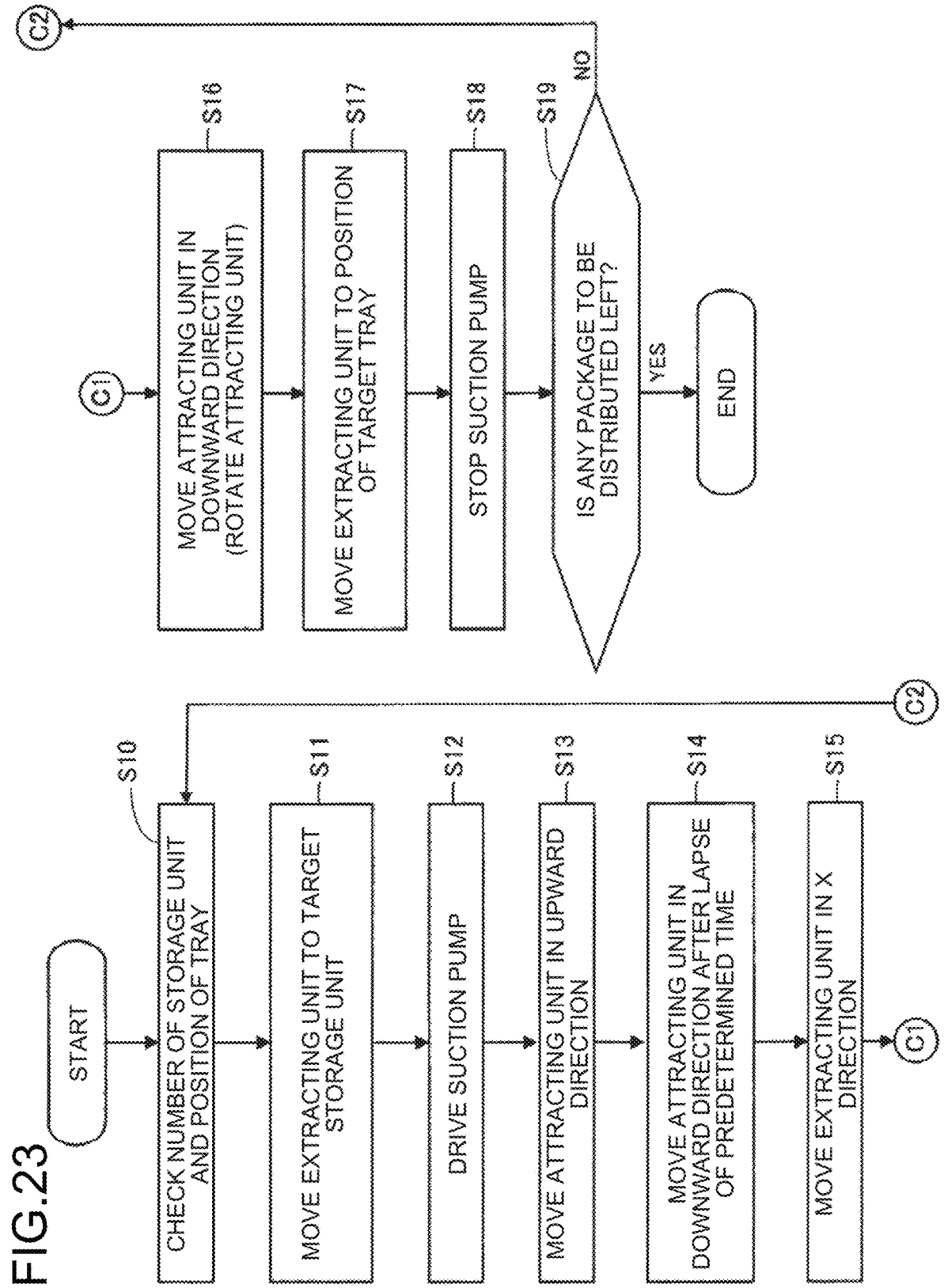
FIG. 23 is a flowchart for explaining the flow of operation of the extracting unit according to the first embodiment.

FIG. 23 is a flowchart for explaining the flow of the operation performed by the extracting unit.

At Step S10 in FIG. 23, the number assigned to the target storage unit 10, which stores therein the package 2 to be distributed, and a position of the target medicine distribution tray 30 to which the package 2 is delivered are checked.

Subsequently, the extracting unit 50 is moved to the target storage unit 10 by the transfer operation of the transfer unit 90 (Step S11). Then, the attracting unit vertical movement motor 63 is driven while the suction pump 48 is driven, and the attracting unit 51 is moved in the upward direction (Step S12 to Step S13). After a lapse of a predetermined time since the attraction pads 52 has attracted and held the package 2 in the storage unit 10 in the lowermost portion, the attracting unit vertical movement motor 63 is driven in a reverse direction to move the attracting unit 51 in the downward direction (Step S14). Thereafter, the extracting unit 50 is moved in the X direction to completely extract the package 2 from the storage unit 10, the attracting unit vertical movement motor 63 is further driven in the reverse direction to move the attracting unit 51 in the downward direction, so that the attracting unit 51 is rotated by about 90 degrees and the posture of the package 2 is changed from an approximately parallel state to the approximately vertical state (Step S15 to Step S16).

Subsequently, the extracting unit 50 is moved to the position of the target medicine distribution tray 30 by the transfer operation of the transfer unit 90. When the extracting unit 50 is moved to the position of the target medicine distribution tray 30, the suction pump 48 is stopped and the package 2 is separated from the attraction pads 52 (Step S17 to Step S18). Then, it is confirmed whether the different package 2 to be distributed is left, and if the different package 2 to be distributed is not left, the flow of a series of operation is terminated (Step S19).

In contrast, at Step S19, if the different package 2 to be distributed is left, the process returns to Step S10 and the same operation as described above is repeated.

In the first embodiment, the posture of the package 2 is changed from the approximately horizontal state to the approximately vertical state at a timing immediately after the package 2 to be extracted is extracted outside the storage unit 10.

With the configuration and the operation as described above, it is possible to provide an apparatus with a small size in which a width in the lateral direction is reduced when there is no enough space in the lateral direction of the extracting means.

A modification of the timing of the flow of the operation performed by the extracting unit will be described below with reference to FIG. 24A to FIG. 24G and FIG. 25. FIG. 24A to FIG. 24G are operation transition diagrams for explaining a timing at which the posture of the attracting unit of the extracting unit according to the first embodiment is changed, and FIG. 25 is a flowchart illustrating the flow of operation that is performed by the extracting unit of the first embodiment in accordance with FIG. 24A to FIG. 24G.

As illustrated in FIG. 24A to FIG. 24D the specific operation as described above with reference to FIG. 18A to FIG. 18F is performed (see Step S10 to Step S15 in FIG. 25). An operation state illustrated in FIG. 24D indicates, similarly to FIG. 18D, the postures of the attraction pads 52 that are attracting and holding, in the extracting unit 50, the extracted package 2 in the approximately horizontal state after the trailing end side of the package 2 is completely extracted from the storage unit 10 by moving the extracting unit 50 in the X direction by the transfer unit 90.

Subsequently, in the flow of operation between FIG. 24D and FIG. 24E, as described by a note in the figure, the extracting unit 50 that is attracting and holding the package 2 in the approximately horizontal state is transferred to the position of the target medicine distribution tray 30 by the transfer operation of the transfer unit 90 (Step S16' in FIG. 25).

As illustrated in FIG. 24E, when the extracting unit 50 is transferred to the position of the target medicine distribution tray 30, the attracting unit vertical movement motor 63 is driven and the attracting unit 51 is moved in the downward direction as illustrated in FIG. 24F and FIG. 24G, to thereby rotate the attraction pads 52 of the attracting unit 51 by about 90 degrees. Accordingly, the posture of the package 2 that is attracted and held by the attraction pads 52 in the approximately horizontal state is rotated by about 90 degrees and changed to the approximately vertical state (Step S17' in FIG. 25). Then, it is confirmed whether the different package 2 to be distributed is left, and if the different package 2 to be distributed is not left, the flow of a series of operation is terminated (Step S19).

In contrast, at Step S19, if the different package 2 to be distributed is left, the process returns to Step S10 and the same operation as described above is repeated.

In the modification of the first embodiment as described above, the posture of the package 2 is changed from the approximately horizontal state to the approximately vertical state at a timing after the package 2 is transferred to the medicine distribution tray 30 by the transfer unit 90 and before start of operation of storing and arranging or distributing the package 2 in the medicine distribution tray 30.

According to the modification as described above, it is possible to transfer the one-dose package in a stable state, and it is possible to provide a medication support apparatus with a small size in which a height of the extracting means is reduced when there is no enough space in the longitudinal direction.

As described above, in the first embodiment, when the package 2 is extracted from the storage unit 10, the extracting unit 50 is located under the storage unit 10, and the package 2 is extracted in the downward direction of the storage unit 10. With this configuration, by extracting the package 2 from the lower side of the storage unit 10, the next package 2 automatically moves in the downward direction (direction toward the package extraction opening 17) by weights of the package 2 remaining in the storage unit 10 and the movable plate 16, so that it is possible to allow the extracting unit 50 to perform the same operation with a simple structure independent of an amount of the packages 2 remaining in the storage unit 10.

Second Embodiment

A configuration and operation of an extracting unit as an extracting means according to a second embodiment, which is different from the extracting means of the first embodiment, will be described below with reference to FIG. 26A too FIG. 28F. FIG. 26A is a front view illustrating the configuration of the extracting unit according to the second embodiment, FIG. 26B is a plan view of FIG. 26A, and FIG. 27A to FIG. 27E and FIG. 28A to FIG. 28F are front views illustrating operation of the extracting unit according to the second embodiment.

As illustrated in FIG. 26A and FIG. 26B, an extracting unit 50A as the extracting means according to the second embodiment is different from the extracting unit 50 of the first embodiment illustrated in FIGS. 17A and 17B mainly in that the extracting unit newly includes a holding unit 71. The holding unit 71 includes a holding tray 72 as a holding means or a holding member that holds the package 2 extracted by the attracting unit 51.

A configuration of the extracting unit 50A of the second embodiment will be described below mainly in terms of a difference from the extracting unit 50 of the first embodiment.

In other words, the extracting unit 50A of the second embodiment includes the attracting unit 51 that extracts the package 2 from the storage unit 10, and the holding unit 71 including the holding tray 72 for holding the extracted package 2. The attracting unit 51 includes the air suction pump 48 similarly to the first embodiment (see FIG. 29), and attracts the package 2 by being negatively pressurized by the suction pump 48.

The suction pump may be arranged on the extracting unit 50, or may be arranged on a different portion in the apparatus. If the suction pump is arranged inside the apparatus, the suction pump is connected via a connection member, such as an air tube.

The attracting unit 51 further includes the attraction pads 52 that are arranged as a pair in the Y direction, that communicate with the suction pump, and that attract the package 2, the attracting ducts 53 that are connected to the attraction pads 52, a duct connection member 64 that is connected to the attracting ducts 53, and an attracting unit vertical moving unit 65 that moves an integrated body including the attraction pads 52, the attracting ducts 53, and the duct connection member 64 in the Z direction.

The attracting unit vertical moving unit 65 includes guide rods 66 that guide the duct connection member 64 in the Z direction and that are arranged as a pair in the Y direction, an endless belt 69 that is wound around a drive pulley 67 and a driven pulley 68, and an attracting unit vertical movement motor 70 that is connected to the drive pulley 67 via a drive transmission member, such as a gear or a belt. The duct connection member 64 is connected and fixed to the belt 69 by a belt holding unit 69a. The guide rods 66 are fixed to a guide rod holding member 50c that is fixed to an extraction frame of the extracting unit 50. The attracting unit vertical movement motor 70 is fixed to an extraction frame of the extracting unit 50A. The attracting unit vertical movement motor 70 is a control target driving member of the attracting unit vertical moving unit 65 (see FIG. 29 to be described later).

The holding unit 71 includes the holding tray 72 that serves as a receiving tray for temporarily storing the extracted package 2. The holding unit 71 further includes guide rod holding members 75 that are connected to both sides in the Y direction such that a posture of the holding tray 72 can be changed, posture deformation assist members 47 that are arranged as a pair in the Y direction to change the posture of the holding tray 72, and a holding unit vertically moving unit 73 that moves the holding tray 72 in the Z direction.

The holding tray 72 has an approximately casing (box) shape to temporarily hold the extracted package 2, and has a recess shape 72a to avoid interference with the above-described integrated body (the attraction pads 52, the attracting ducts 53, and the duct connection member 64) of the attracting unit 51.

An inclined portion 47a is formed on an upper left portion of each of the posture deformation assist members 47 in the figure.

Meanwhile, the holding member (receiving board) for holding the package 2 extracted by the attracting unit 51 may have a simple box shape like the holding tray 72, or may include a clip portion that is linked to motion of the holding member and that grips the extracted package 2.

The extracting unit 50A further includes a posture changing means for changing the posture of the package 2 extracted from the storage unit 10 to the approximately vertical state. The posture changing means of the extracting unit 50A includes, as main structural members, the posture deformation assist members 47, the holding tray 72, and the holding unit vertically moving unit 73.

The holding unit vertically moving unit 73 includes guide rods 74 that guide the holding tray 72 in the Z direction and that are arranged as a pair in the Y direction, an endless belt 78 that is wound around a drive pulley 76 and a driven pulley 77, and a holding unit vertical movement motor 79 that is connected to the drive pulley 76 via a drive transmission member, such as a gear or a belt. The holding unit vertical movement motor 79 is a control target driving member of the holding unit vertically moving unit 73 (see FIG. 29 to be described later). The guide rod holding members 75 are connected and fixed to the belt 78 by a belt holding unit 78a. The holding unit vertical movement motor 79 is fixed on an extraction frame of the extracting unit 50A.

Meanwhile, each of the attracting unit vertical moving unit 65 and the holding unit vertically moving unit 73 as described above is not limited to an up-down reciprocating movement mechanism using belt driving, but may be a reciprocating straight movement mechanism using a rack and pinion or the like.

Operation of the extracting unit 50A will be described below with reference to FIG. 27A to FIG. 27E and FIG. 28A to FIG. 28F. Meanwhile, for the sake of simplification of explanation and easy understanding, in this example, it is assumed that, by the operation of the transfer unit 90 illustrated in FIG. 1A, the extracting unit 50A is located between the storage units 10 on the drawn unit 21 that is arranged in the uppermost portion of the main-body frame 199 in FIG. 1A and the medicine distribution tray 30 that is arranged just below the drawn unit 21.

Figures 27A, 27B, 27C, 27D, 27E:
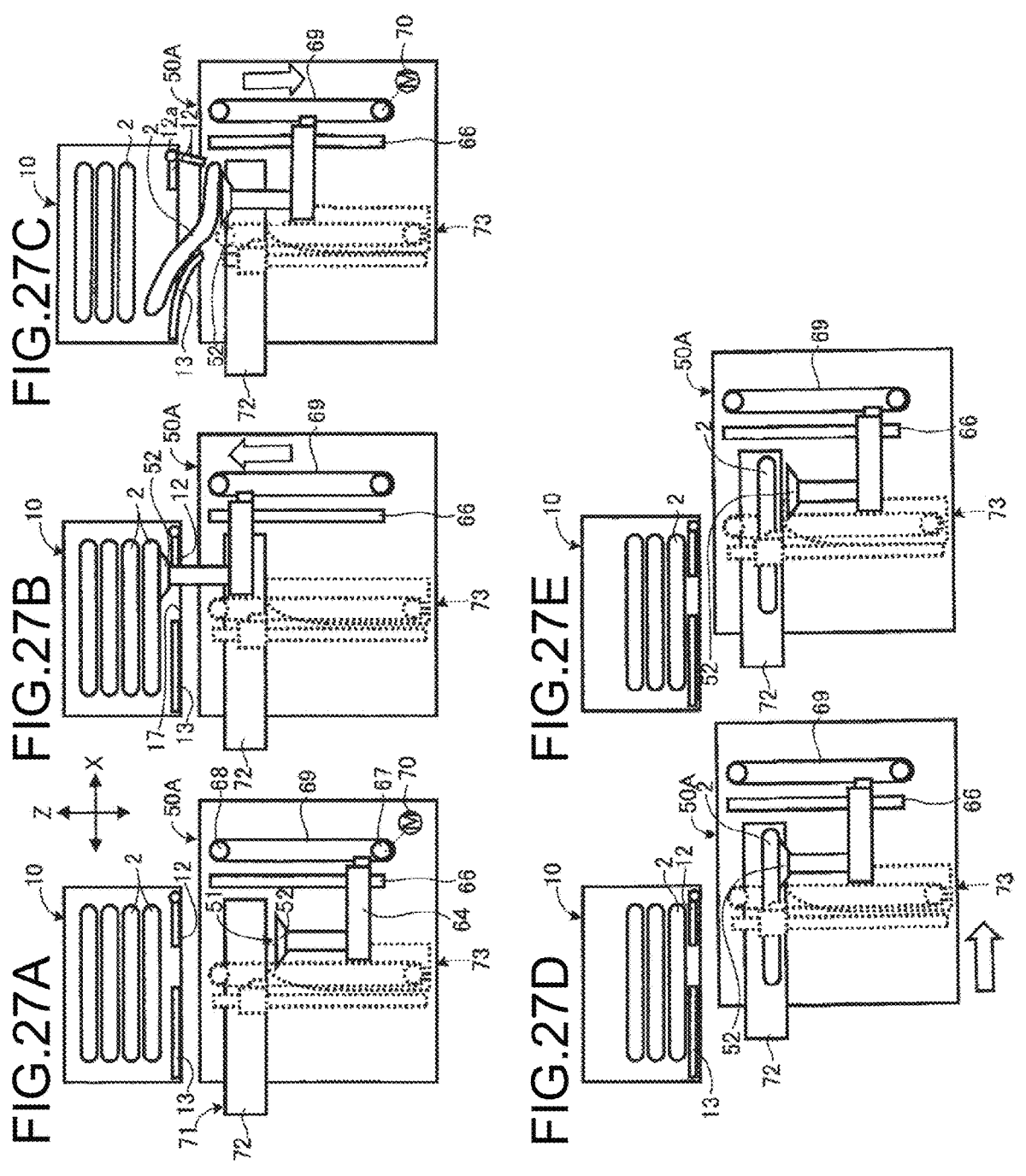

As illustrated in FIG. 27A, by the operation of the transfer unit 90 illustrated in FIG. 1A, the extracting unit 50A moves to a position just below the storage unit 10 and enters a movement stopped state. In this case, the attracting unit vertical movement motor 70 of the attracting unit vertical moving unit 65 is stopped, and the attraction pads 52 are located under and in the vicinity of the holding tray 72 that is in the approximately horizontal state. Thereafter, as illustrated in FIG. 27B, with the operation of the attracting unit vertical movement motor 70, the attraction pads 52 move in the upward direction, are inserted through the package extraction opening 17 between the left support unit 12 and the right support unit 13, come into contact with the package 2 located in the lowermost portion of the storage unit 10, and simultaneously attract the package 2. At this time, the suction pump is driven in advance and attraction operation is enabled.

Subsequently, as illustrated in FIG. 27C, with reverse operation of the attracting unit vertical movement motor 70, the attraction pads 52 move in the downward direction while attracting the package 2, and the package 2 is extracted from the storage unit 10.

As illustrated in FIG. 27C, the left support unit 12 and the right support unit 13 are opened and closed by the drawing operation of the attraction pads 52, so that it is not necessary to separately provide a drive source for opening and closing operation, and it is possible to reliably extract the package 2 from the storage unit 10, simplify the apparatus, and save power.

A characteristic specific operation of extracting the package 2 is performed in the same manner as in the first embodiment. Specifically, as illustrated in FIG. 27D, the extracting unit 50A is moved in the X direction that is the lateral direction by the operation of the transfer unit 90, and the trailing end side of the package 2 is completely extracted from the storage unit 10. In this case, in the process of extracting the package 2 from the storage unit 10, the extracting unit 50A extracts the leading end side of the package downward from the storage unit 10, and the transfer unit 90 moves the extracting unit 50A such that the trailing end side of the package 2 is extracted from the storage unit 10 while the leading end side of the package 2 is extracted downward from the storage unit 10.

Then, the moving direction of the extracting unit 50A moved by the transfer unit 90 is set to the X direction that is the lateral direction in which a supported state of the trailing end side of the package 2 by the right support unit 13 is released and the trailing end side is extracted from the package extraction opening 17.

Subsequently, as illustrated in FIG. 27E, the extracted package 2 is held by the holding tray 72. Thereafter, the attraction pads 52 are moved downward to positions at which the attraction pads do not come into contact with the extracted package 2, in other words, positions under and in the vicinity of the holding tray 72 that is laterally oriented and that is in the horizontal state similarly to the state as illustrated in FIG. 27A (initial positions of the attraction pads 52). At this time, an outer bottom wall surface of the holding tray 72 comes into contact with outer upper wall surfaces of the posture deformation assist members 47.

Subsequently, as illustrated in FIG. 28A, FIG. 28B, and FIG. 28C, operation of changing the posture of the holding tray 72 and inserting the package 2 from the holding tray 72 to the medicine distribution tray 30 is performed. After the operation illustrated in FIG. 28A, only operation by the holding unit 71 is performed while the operation of the attracting unit 51 is stopped (the attraction pads 52 are located at the initial positions as described above); therefore, the attracting unit 51 side is indicated by a dashed line and the holding unit 71 side is indicated by a solid line.

Here, the operation illustrated in FIG. 28A to FIG. 28C, in other words, a mechanism that changes the posture of the holding tray 72 holding the package 2 will be further described below. The holding tray 72 is configured to rotate by 90 degrees such that the posture of the package 2 in the holding tray 72 can be changed from a lateral orientation in the approximately horizontal state to a vertical orientation in the approximately vertical state, and connection portions between the holding tray 72 and the guide rod holding members 75 are connected in a rotatable manner. Further, with rotating movement of the belt 78, the guide rod holding members 75 move downward in the Z direction along the guide rods 74, an outer bottom wall surface of the holding tray 72 accordingly comes into contact with the inclined portions 47a of the posture deformation assist members 47 in a linked manner, and the outer bottom wall surface of the holding tray 72 subsequently comes into contact with vertical portions 47b that are formed on the posture deformation assist members 47. Accordingly, the postures of the holding tray 72 and the package 2 held by the holding tray 72 are changed from the lateral orientations in the approximately horizontal states to the vertical orientations in the approximately vertical states. At this time, a biasing force of a spring (not illustrated) in a clockwise direction in FIG. 28A acts on the holding tray 72 such that the postures of the holding tray 72 and the package 2 held by the holding tray 72 can always be maintained in the lateral orientations.

Subsequently, as illustrated in FIG. 28D to FIG. 28E, the holding tray 72 that is holding the package 2 and that is in the approximately vertical state moves downward in the Z direction along the guide rods 74 via the guide rod holding members 75 with further rotating movement of the belt 78. Then, if the holding tray 72 of the approximately vertical state comes into contact with an upper end portion of the medicine distribution tray 30, a bottom portion 72b of the holding tray 72 is opened in conjunction with the contact operation, so that the package 2 in the holding tray 72 is transferred to the inside of the medicine distribution tray 30. In this manner, the bottom portion 72b of the holding tray 72 in the approximately vertical state is opened and closed in conjunction with the downward movement of the holding tray 72 in the Z direction. This operation may be performed by, for example, a mechanism that includes a projection (not illustrated) on the extracting unit 50A and that is opened by coming into contact with the bottom portion 72b when arriving at a position at which the holding tray 72 in the approximately vertical state is located.

Meanwhile, the above-described projection arranged on the extracting unit 50A need not always be arranged in only the extracting unit 50A. A part of the projection may be arranged on the medicine distribution tray 30, or an intermediate member (not illustrated) that is arranged between the drawn unit 21 (see FIG. 1A, FIG. 16, etc.) and the medicine distribution tray 30 may implement a function of the projection.

Subsequently, as illustrated in FIG. 28F, the holding tray 72 in an empty state after the package 2 that has been held in the holding tray 72 is transferred to the medicine distribution tray 30 moves upward in the Z direction along the guide rods 7 via the guide rod holding members 75, with reverse rotating movement of the belt 78.

As described above, even in the second embodiment, when the package 2 is to be extracted from the storage unit 10, the extracting unit 50A is located under the storage unit 10, and the package 2 is extracted in the downward direction of the storage unit 10. In this manner, by extracting the package 2 from the lower side of the storage unit 10, the next package 2 automatically moves in the downward direction (direction toward the package extraction opening 17) by weights of the package 2 remaining in the storage unit 10 and the movable prate 16, so that it is possible to allow the extracting unit 50 to perform the same operation with a simple structure independent of an amount of the packages 2 remaining in the storage unit 10.

Figure 29:
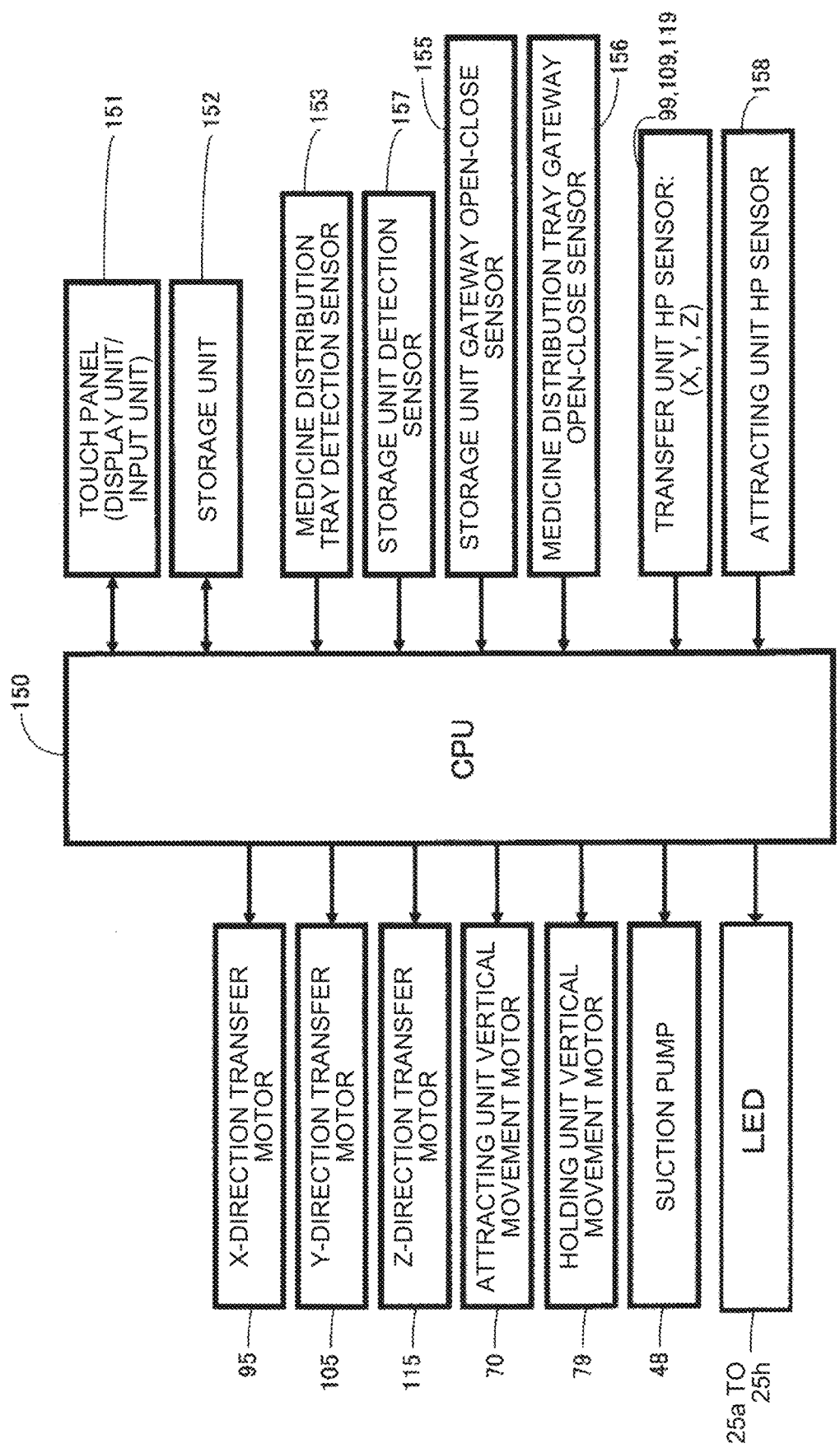
FIG. 29 is a control block diagram illustrating a main control configuration of a medication support apparatus according to the second embodiment.

A control configuration of the medication support apparatus 200 according to the second embodiment will be described below with reference to FIG. 29. FIG. 29 is a control block diagram illustrating a main control configuration of the medication support apparatus according to the second embodiment.

The control configuration of the second embodiment illustrated in FIG. 29 is different form the control configuration of the first embodiment illustrated in FIG. 21 only in that an attracting unit vertical movement motor is used instead of the attracting unit vertical movement motor 63 of the first embodiment and the holding unit vertical movement motor 79 is newly used. Other control configurations are the same between the first and the second embodiments, and therefore, explanation thereof will be omitted.

Entire main operation of the medication support apparatus will be described below with reference to FIG. 30A to FIG. 30E. The operation is executed in accordance with a control command of the CPU of the control unit 150.

As illustrated in FIG. 30A to FIG. 30C, the extracting unit 50A performs operation of extracting the package 2 from the lower side of the storage unit 10. Specific operation is the same as the operation described above with reference to FIG. 27A to FIG. 27C. Then, as illustrated in FIG. 27D, the extracting unit 50A is moved in the X direction that is the lateral direction by the operation of the transfer unit 90, and the trailing end side of the package 2 is completely extracted from the storage unit 10.

The package 2 that is completely extracted from the storage unit 10 is received by the holding tray 72 as illustrated in FIG. 27E, and thereafter, through the posture changing operation of the holding tray 72 similarly to the operation described above with reference to FIG. 28A to FIG. 28C, the package 2 is held by the holding tray 72 of the extracting unit 50A together with the holding tray 72 in the approximately vertical state as illustrated in FIG. 30D. Then, as illustrated in FIG. 30D, the transfer unit 90 transfers the extracting unit 50A in which the package 2 is held by the holding tray 72 to the medicine distribution portion 29 at which the medicine distribution tray 30 is set. When the extracting unit 50A is transferred to a position approximately just below the medicine distribution tray 30 in the medicine distribution portion 29, the package 2 is inserted in the predetermined section 33 as a predetermined position in the medicine distribution tray 30 by the operation described above with reference to FIG. 26D to FIG. 28F.

The operation as described above is repeated a plurality of number of times to insert the necessary packages 2 to the predetermined sections 33 in the medicine distribution tray 30, and thereafter, as illustrated in FIG. 30E, the medicine distribution tray 30 is extracted from, for example, the second gateway portion 42 to the outside of the apparatus and received by a medication assistant, such as staff in a nursing home or the like.

The flow of the operation of the extracting unit illustrated in FIG. 30A to FIG. 30F will be further described below with reference to FIG. 31. FIG. 31 is a flowchart illustrating the flow of the operation performed by the extracting unit.

At Step S20 in FIG. 31, the number assigned to the target storage unit 10, which stores therein the package 2 to be distributed, is checked, and a position of the target medicine distribution tray 30 to which the package 2 is inserted and delivered is also checked.

Subsequently, the extracting unit 50A is moved to the target storage unit 10 by the transfer operation of the transfer unit 90 (Step S21). Then, the attracting unit vertical movement motor 70 is driven while the suction pump 48 is driven, and the attracting unit 51 is moved in the upward direction (Step S22 to Step S23). After a lapse of a predetermined time since the attraction pads 52 has attracted and held the package 2 in the storage unit 10 in the lowermost portion, the attracting unit vertical movement motor 70 is driven in a reverse direction to move the attracting unit 51 in the downward direction. At this time, the extracting unit 50A is moved in the X direction to completely extract the package 2 from the storage unit 10, and the package 2 that is completely extracted from the storage unit 10 is received by the holding tray 72 as illustrated in FIG. 27E, so that the package 2 and the holding tray 72 are held in the approximately horizontal state by the extracting unit 50A. Then, the suction pump 48 is stopped (Step S24 to Step S26).

Subsequently, the holding unit vertical movement motor 79 is driven to move the holding unit 71 in the downward direction (Step S27). At this time, through the posture changing operation by the rotation of the holding tray 72 similarly to the operation described above with reference to FIG. 28A to FIG. 28C, the package 2 and the holding tray 72 are held in the approximately vertical state by the extracting unit 50A as illustrated FIG. 30D.

Subsequently, the extracting unit 50A in which the package 2 and the holding tray 72 are held in the approximately vertical state is moved to the position of the target medicine distribution tray 30 by the transfer operation of the transfer unit 90. When the extracting unit 50A is moved to the position of the target medicine distribution tray 30, the holding unit vertical movement motor 79 is driven to move the holding unit 71 in the downward direction (Step S28 to Step S29).

Subsequently, after a lapse of a predetermined time that is needed to move the holding unit 71 in the downward direction and insert or deliver the package 2 in the holding tray 72 to the predetermined section 33 in the medicine distribution tray 30, the holding unit vertical movement motor 79 is driven in a reverse rotation direction to move the holding unit 71 in the upward direction, so that the holding tray 72 is held in the approximately horizontal state at an initial position (HP) in the extracting unit 50A. (Step S29). Then, it is confirmed whether the different package 2 to be distributed is left, and if the different package 2 to be distributed is not left, the flow of a series of operation is terminated (Step S30).

In contrast, at Step S30, if the different package 2 to be distributed is left, the process returns to Step S20 and the same operation as described above is repeated.

In the example of the second embodiment as described above, as illustrated in FIG. 30A to FIG. 30E and FIG. 31, the posture of the package 2 is changed from the approximately horizontal state to the approximately vertical state a timing immediately after the entire package 2 that is to be extracted is extracted outside the storage unit 10. With this configuration, it is possible to achieve the same effect as the first embodiment, in other words, it is possible to provide an apparatus with a small size in which a width in the lateral direction is reduced when there is no enough space in the lateral direction of the extracting means.

Figure 32:
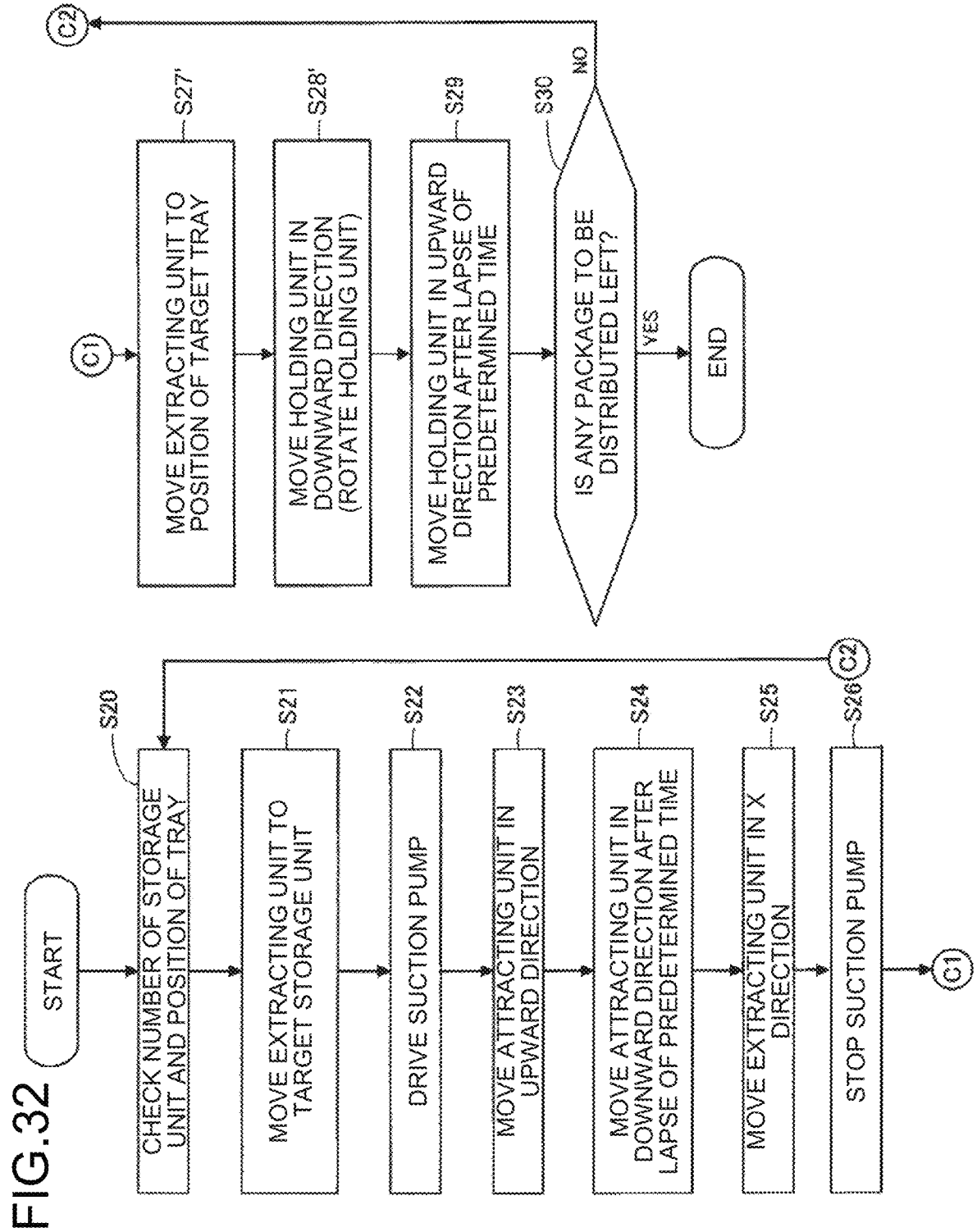
FIG. 32 a flowchart for explaining a timing at which a posture of an attracting unit of an extracting unit according to another example different from the example in FIG. 31 is changed.

Another modification, which is different from the flow of the operation of the extracting unit in FIG. 31, will be described below with reference to FIG. 32. FIG. 32 is a flowchart illustrating a modification of the flow of the operation performed by the extracting unit.

The modification of the flow of the operation of the extracting unit illustrated in FIG. 32 is different from the flow of the operation of the extracting unit illustrated in FIG. 31 only in that the posture of the package 2 is changed from the approximately horizontal state to the approximately vertical state at a timing after the transfer unit 90 has transferred the package 2 to the medicine distribution tray 30 and before operation of arranging the package 2 on the medicine distribution tray 30 is started.

In other words, the flow of operation from Step S20 to Step S26 in FIG. 32 is the same as the flow of the operation of the extracting unit in FIG. 31, and the flow of operation from Step S29 to Step S30 in FIG. 32 is the same as the flow of the operation of the extracting unit in FIG. 31.

The operation in FIG. 32 is different in that "the extracting unit is moved to a position of the target tray" at Step S27', instead of the operation of "moving the holding unit in the downward direction (rotating the holding tray)" at Step S27 in FIG. 31. Furthermore, the operation in FIG. 32 is different in that "the holding unit is moved in the downward direction (the holding tray is rotated)" at Step S28' instead of the operation of "moving the extracting unit to the position of the target tray" at Step S28 in FIG. 31.

In the modification of the second embodiment as described above, as illustrated in FIG. 32, the posture of the package 2 changed from the approximately horizontal state to the approximately vertical state at a timing after the transfer unit 90 has transferred the package 2 to the medicine distribution tray 30 and before the operation of arranging the package 2 on the medicine distribution tray 30 is started. With this configuration, it is possible to achieve the same effects as those of the modification of the first embodiment illustrated in FIGS. 24A to 24G and FIG. 25, in other words, it is possible to transfer the one-dose package in a stable state, and it is possible to provide a medication support apparatus with a small size in which a height of the extracting means is reduced when there is no enough space in the longitudinal direction.

As described above, even in the second embodiment, similarly to the first embodiment, when the package 2 is to be extracted from the storage unit 10, the extracting unit 50A is arranged under the storage unit 10 and the package 2 is extracted in the downward direction of the storage unit 10. In this manner, by extracting the package 2 from the lower side of the storage unit 10, the next package 2 automatically moves in the downward direction (direction toward the package extraction opening 17) by weights of the package 2 remaining in the storage unit 10 and the movable plate 16, so that it is possible to allow the extracting unit 50A to perform the same operation with a simple structure independent of an amount of the packages 2 remaining in the storage unit 10.

In the first embodiment, the second embodiment, etc., the aspects and the effects as described below are substantially described.

Specifically, as a first aspect, a medication support apparatus, such as the medication support apparatus 200, includes a storage means, such as the storage unit 10, that stores therein a one-dose package, such as the package 2, in which medicines, such as medicines 3, are packed; an extracting means, such as the extracting unit 50 or the extracting unit 50A, that extracts the specific one-dose package from the storage means; a transferring means, such as the transfer unit 90, that transfers the one-dose package extracted by the extracting means; and a medicine distributing means, such as the medicine distribution tray 30, on which the one-dose package transferred by the transferring means is arranged, where when the one-dose package is extracted from the storage means, the extracting means is located under the storage means.

With this configuration, according to the first aspect, it is possible to provide a medication support apparatus that has a simple structure and that reduces time and effort for a medicated person or a medication assistant who assists medication, to perform medication.

As a second aspect, in the first aspect, the extracting means extracts one end side of the one-dose package downward from the storage means in a process of extracting the one-dose package from the storage means, and the transferring means moves the extracting means such that the other end side of the one-dose package is extracted from the storage means while the one end side of the one-dose package is extracted downward from the storage means.

With this configuration, according to the second aspect, it is possible to provide a medication support apparatus with a simple structure and with a small size.

As a third aspect, in a first aspect or a second aspect, an opening, such as the package extraction opening 17, for extracting the one-dose package and a support member, such as the left support unit 12 and the right support unit 13, that supports the one-dose package in the storage means and that are openable and closeable by operation of extracting the one-dose package from the storage means by the extracting means are arranged in a lower portion of the storage means, and a moving direction in which the extracting means is moved by the transferring means is set to a lateral direction, such as the X direction, in which the other end side of the one-dose package is extracted from the opening while being released from a state of being supported by the support member.

With this configuration, according to the third aspect, it is possible to provide a medication support apparatus with a small size in which a distance between the storage means and the extracting means facing each other is reduced when the one-dose package is extracted from the storage means.

As a fourth aspect, in any one of the first to the third aspects, the one-dose package in the storage means is stored in a stacked manner in an approximately horizontal state, and the extracting means includes a posture changing means that changes a posture of the extracted one-dose package to an approximately vertical state.

With this configuration, according to the fourth aspect, it is possible to provide a medication support apparatus with a simple structure and with a small size.

As a fifth aspect, in the fourth aspect, the extracting means, such as the extracting unit 50, includes an attracting means, such as the attraction pads 52, that attracts and extracts the one-dose package in the storage means, and the posture of the one-dose package is changed from the approximately horizontal state to the approximately vertical state by rotation operation of the attracting means.

With this configuration, according to the fifth aspect, it is possible to provide a medication support apparatus with a simple configuration and with a small size.

As a sixth aspect, in the fourth aspect, the extracting means, such as the extracting unit 50A, includes an attracting means, such as the attraction pads 52, that attracts and extracts the one-dose package in the storage means, and a holding means, such as the holding tray 72, that holds the one-dose package extracted by the attracting means, where the posture of the one-dose package is changed from the approximately horizontal state to the approximately vertical state by rotation operation of the holding means.

With this configuration, according to the sixth aspect, it is possible to provide a medication support apparatus with a simple structure and with a small size.

As a seventh aspect, in any one of the fourth to the sixth aspects, a timing at which the posture of the one-dose package is changed from the approximately horizontal state to the approximately vertical state is set to be immediately after the entire one-does package to be extracted is extracted outside the storage means.

With this configuration, according to the seventh aspect, it is possible to provide a medication support apparatus with a small size in which a width in the lateral direction is reduce when there is no enough space in the lateral direction of the extracting means.

As an eighth aspect, in any one of the fourth to the sixth aspects, a timing at which the posture of the one-dose package is changed from the approximately horizontal state to the approximately vertical state is set to be after the transferring means has transferred the one-dose package to the medicine distributing means and before operation of arranging the one-dose package on the medicine distributing means is started.

With this configuration, according to the eighth aspect, it is possible to provide a medication support apparatus that is able to transfer the one-dose package in a stable state, and that has a small size in which a height of the extracting means is reduced when there is no enough space in the longitudinal direction.

As a ninth aspect, in the fifth aspect, up-down operation performed by the attracting means when the one package in the storage means is attracted and extracted and the rotation operation are performed by the same driving mechanism.

With this configuration, according to the ninth aspect, it is possible to provide a medication support apparatus with a simple structure and with a small size.

As a tenth aspect, in any one of the fifth, the sixth, and the ninth aspects, the attracting means is an air suction type attraction pad.

With this configuration, according to the tenth aspect, it is possible to provide a medication support apparatus with a simple structure and with a small size.

As an eleventh aspect, in any one of the first to the tenth aspects, the transferring means transfers the one dose package extracted by the extracting means via the extracting means, such as the extracting unit 50 or the extracting unit 50A.

Supplementary explanation on the background technology will be described below. As a technology similar to the present invention, an apparatus disclosed in Japanese Unexamined Patent Application Publication No. 2017-153646 is known. The apparatus includes an opening in a lower portion of a medicine package storage unit and extracts a medicine package from the opening; however, because the medicine is stored in a horizontal direction, a discharge mechanism is needed. Therefore, there is a problem in that a structure is complicated and costs increase.

According to an embodiment, it is possible to provide an apparatus that has a simple structure and that reduces time and effort for a medicated person or a medication assistant who assists medication to perform medication.

The above-described embodiments are illustrative and do not limit the present invention. Thus, numerous additional modifications and variations are possible in light of the above teachings. For example, at least one element of different illustrative and exemplary embodiments herein may be combined with each other or substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of the present invention may be practiced otherwise than as specifically described herein.

The method steps, processes, or operations described herein are not to be construed as necessarily requiring their performance in the particular order discussed or illustrated, unless specifically identified as an order of performance or clearly identified through the context. It is also to be understood that additional or alternative steps may be employed.

What is claimed is:

1. A medication support apparatus comprising:
a storage container configured to store, in a stacked manner, one-dose packages in each of which medicines are packed;
an extracting device configured to extract a specific one-dose package from the storage container;
a transfer device configured to transfer the one-dose package extracted by the extracting device; and
a medicine distributing tray on which the one-dose package transferred by the transfer device is configured to be arranged,
wherein
the extracting device is configured to be located under the storage container prior to extracting the one-dose package from the storage container, and
extract a first end side of the one-dose package downward from the storage container in a process of extracting the one-dose package from the storage container, and
the transfer device is configured to move the extracting device such that a second end side of the one-dose package is extracted from the storage container while the first end side of the one-dose package is extracted downward from the storage container.

2. The medication support apparatus according to claim 1, wherein the transfer device is configured to transfer, via the extracting device, the one-dose package extracted by the extracting device.

3. The medication support apparatus according to claim 1, wherein
an opening for extracting the one-dose package and a support member configured to support the one-dose package in the storage container and capable of being opened and closed by operation of the extracting the one-dose package from the storage container are arranged in a lower portion of the storage container, and
a direction in which the extracting device is moved by the transfer device is set to a lateral direction in which the second end side of the one-dose package is extracted from the opening while being released from a state of being supported by the support member.

4. The medication support apparatus according to claim 1, wherein
the one-dose packages in the storage container are stored in the stacked manner in an approximately horizontal state, and
the extracting device is further configured to change a posture of the extracted one-dose package to an approximately vertical state.

5. The medication support apparatus according to claim 4, wherein
the extracting device is further configured to attract and extract the one-dose package in the storage container, and
change the posture of the one-dose package from the approximately horizontal state to the approximately vertical state using a rotation operation.

6. The medication support apparatus according to claim 4, wherein the extracting device is further configured to:
attract and extract the one-dose package in the storage container; and
hold the extracted one-dose package, and
change the posture of the one-dose package from the approximately horizontal state to the approximately vertical state using a rotation operation.

7. The medication support apparatus according to claim 4, wherein a timing at which the posture of the one-dose package is changed from the approximately horizontal state to the approximately vertical state is set to be immediately after the entire one-dose package to be extracted is extracted outside the storage container.

8. The medication support apparatus according to claim 4, wherein a timing at which the posture of the one-dose package is changed from the approximately horizontal state to the approximately vertical state is set to be after the transfer device has transferred the one-dose package to the medicine distributing tray and before operation of arranging the one-dose package on the medicine distributing tray is started.

9. The medication support apparatus according to claim 5, wherein an up-down operation performed by the extracting device in response to attracting and extracting the one-dose package in the storage container and the rotation operation are performed by a same drive mechanism.

10. The medication support apparatus according to claim 5, wherein the extracting device comprises an air suction type attracting member.

11. A medication support apparatus comprising:
a storage container configured to store, in a stacked manner, one-dose packages in each of which medicines are packed;
an extracting device configured to extract a specific one-dose package from the storage container;
a transfer device configured to transfer the one-dose package extracted by the extracting device; and
a medicine distributing tray on which the one-dose package transferred by the transfer device is configured to be arranged,
wherein
an extraction portion for the one-dose package to be extracted from the storage container by the extracting device is in a lower portion in the storage container, and the extraction portion includes a first support member configured to support the one-dose package at a plurality of positions-,
the extraction portion includes a plurality of support members, the plurality of support members including the first support member, and
at least one of the plurality of support members is movable.

12. The medication support apparatus according to claim 11, wherein at least one of the plurality of support members is an elastic member.

13. The medication support apparatus according to claim 11, wherein at least one of the plurality of support members has a projecting shape overlapping with the one-dose package in a plane view.

14. The medication support apparatus according to claim 13, wherein the extracting device passes by both ends of the projecting shape of the support member.

15. The medication support apparatus according to claim 11, wherein a support member of the plurality of support members, by which the extracting device passes, is movable.

16. The medication support apparatus according to claim 3, wherein the support member includes a rotary shaft.

17. The medication support apparatus according to claim 16, further comprising:
a coil spring connected to the rotary shaft and a bottom wall of the storage container, the coil spring configured to provide a biasing force to the support member.

18. The medication support apparatus according to claim 11, wherein the first support member includes a rotary shaft.

19. The medication support apparatus according to claim 18, further comprising:
a coil spring connected to the rotary shaft and a bottom wall of the storage container, the coil spring configured to provide a biasing force to the support member.

20. A medication support apparatus comprising:
a storage container configured to store, in a stacked manner, one-dose packages in each of which medicines are packed;
an extracting device configured to extract a specific one-dose package from the storage container;
a transfer device configured to transfer the one-dose package extracted by the extracting device; and
a medicine distributing tray on which the one-dose package transferred by the transfer device is configured to be arranged,
wherein
an extraction portion for the one-dose package to be extracted from the storage container by the extracting device is in a lower portion in the storage container, and the extraction portion includes a first support configured to support the one-dose package at a plurality of positions,
the extraction portion includes a plurality of supports, the plurality of supports including the first support, and
at least one of the plurality of supports is an elastic member.

* * * * *